United States Patent
Pandey et al.

(10) Patent No.: US 11,083,793 B2
(45) Date of Patent: Aug. 10, 2021

(54) EPIDERMAL GROWTH FACTOR RECEPTOR (EGFR) TARGETED PHOTOSENSITIZERS

(71) Applicants: Health Research, Inc., Buffalo, NY (US); Photolitec, LLC, East Amherst, NY (US)

(72) Inventors: Ravindra K. Pandey, East Amherst, NY (US); Heinz Baumann, Buffalo, NY (US); Khurshid Guru, East Amherst, NY (US); Ravindra Cheruku, Buffalo, NY (US); Erin Tracy, Buffalo, NY (US); Farukh Durrani, East Amherst, NY (US); Joseph Cacaccio, Buffalo, NY (US); Kevin Siters, East Amherst, NY (US)

(73) Assignees: Health Research, Inc., Buffalo, NY (US); Photolitec, LLC, East Amherst, NY (US)

( * ) Notice: Subject to any disclaimer, the term of this patent is extended or adjusted under 35 U.S.C. 154(b) by 0 days.

(21) Appl. No.: 16/469,574

(22) PCT Filed: Dec. 13, 2017

(86) PCT No.: PCT/US2017/066225
§ 371 (c)(1),
(2) Date: Jun. 13, 2019

(87) PCT Pub. No.: WO2018/112111
PCT Pub. Date: Jun. 21, 2018

(65) Prior Publication Data
US 2020/0078461 A1 Mar. 12, 2020

Related U.S. Application Data

(60) Provisional application No. 62/603,777, filed on Jun. 9, 2017, provisional application No. 62/433,554, filed on Dec. 13, 2016.

(51) Int. Cl.
*A61K 41/00* (2020.01)
*A61P 35/00* (2006.01)
*A61K 49/00* (2006.01)
*C07D 487/22* (2006.01)

(52) U.S. Cl.
CPC ...... *A61K 41/0076* (2013.01); *A61K 49/0036* (2013.01); *A61P 35/00* (2018.01); *C07D 487/22* (2013.01)

(58) Field of Classification Search
None
See application file for complete search history.

(56) References Cited

U.S. PATENT DOCUMENTS

| 5,314,905 A | 5/1994 | Pandey et al. |
| 2010/0256136 A1 | 10/2010 | Pandey et al. |
| 2013/0210756 A1 | 8/2013 | Kim et al. |

FOREIGN PATENT DOCUMENTS

| CN | 103341166 A | 10/2013 |

OTHER PUBLICATIONS

Nyuchev, A. V. et al., Synthesis of Chlorin-(Arylamino) quinazoline Hybrids as Models for Multifunctional Drug Development, Synthesis, Aug. 20, 2015, vol. 47, No. 23, pp. 3717-3726.

Zhang, Y., et al., Synthesis and Evaluation of Novel Erlotinib-NSAID Conjugates as More Comprehensive Anticancer Agents, ACS Medicinal Chemistry Letters, Sep. 8, 2015, vol. 6, pp. 1086-1090.

*Primary Examiner* — Joseph R Kosack
(74) *Attorney, Agent, or Firm* — Hodgson Russ LLP

(57) ABSTRACT

Compounds including a tetrapyrrolic or reduced tetrapyrrolic group/moiety and an epidermal growth factor receptor targeting group are disclosed. For example, a compound includes a tetrapyrrolic or reduced tetrapyrrolic group or moiety, a linker moiety, an epidermal growth factor receptor targeting group, and, optionally, a PET-active functional group. Uses of the compounds, for example, methods of treating a hyperproliferative tissue in an individual, and kits including one or more of the compounds are also provided.

20 Claims, 23 Drawing Sheets

A, UMUC3, UMUC3

EPIDERMAL GROWTH FACTOR RECEPTOR (EGFR) TARGETED PHOTOSENSITIZERS

CROSS REFERENCE TO RELATED APPLICATIONS

This application claims priority to U.S. Provisional Application No. 62/433,554, filed on Dec. 16, 2016, and to U.S. Provisional Application No. 62/603,777, filed on Jun. 9, 2017, the disclosures of which are hereby incorporated herein by reference.

STATEMENT REGARDING FEDERALLY SPONSORED RESEARCH

This invention was made with government support under contract no. CA55791 awarded by the National Institutes of Health. The government has certain rights in the invention.

FIELD OF THE DISCLOSURE

The disclosure generally relates to tetrapyrrolic compounds. More particularly the disclosure relates to tetrapyrrolic compounds that target epidermal growth factor receptor and their use in PDT.

BACKGROUND OF THE DISCLOSURE

Photodynamic therapy (PDT) is a non-invasive cancer treatment modality, and it is an alternative to surgery, chemotherapy and radiotherapy. Since the approval of Photofrin, a hematoporphyrin-based photosensitizer by various health organizations, efforts are underway to develop improved photosensitizers with desired photophysical properties and reduced skin phototoxicity. During the last 20 years, a variety of PDT agents with long wavelength ranging of 660-800 nm have been synthesized in various laboratories with desired photophysical properties and reduced phototoxicity. Though a large number of photosensitizers have been reported, but there has not been much success in improving the tumor selectivity and specificity of these agents because, tumor cells in general have non-specific affinity to porphyrins.

Attempts have been made to direct photosensitizers to known cellular targets by conjugating photosensitizers, where a PDT agent is linked to a known tumor-targeted molecule. The targeting molecules selected for such an approach were: cholesterol, certain chemotherapy agents, monoclonal antibody, carbohydrates and peptides (linear and cyclic). However, there is still a major challenge to develop photosensitizers that can be selectively taken up by the malignant cells.

Epidermal growth factor receptor (EGFR) is a cell surface receptor for members of the epidermal growth factor family of extracellular protein ligands. Mutations that lead to EGFR overexpression (known as upregulation) or over-activity have been associated with a number of cancers, including squamous-cell carcinoma of the bladder, lung (80% of cases), anal cancers, glioblastoma (50%) and epithelial tumors of the head and neck (80-100%). These somatic mutations involving EGFR lead to its constant activation, which produces uncontrolled cell division. Mutations, amplifications or misregulations of EGFR family members are implicated in about 30% of all epithelial cancers.

SUMMARY OF THE DISCLOSURE

In an aspect, the present disclosure describes compounds compromising a photosensitizer (PS) (e.g., a tetrapyrrolic group/moiety or reduced tetrapyrrolic group/moiety, such as, for example, but not limited to, a group/moiety derived from HPPH), a linker moiety, and erlotinib or erlotinib analog groups. Such a compound has the following structure: PS-L-E, where PS is a photosensitizer group or moiety (e.g., a tetrapyrrolic group or moiety, such as, for example, but not limited to, derived from HPPH)), L is a linker moiety, and E is an erlotinib group or moiety or an erlotinib analog group. The compounds are asymmetric compounds. The compounds target EGFR and can have desirable specificity (e.g., tumor specificity and/or cellular specificity) and tumor retention.

In an example, compounds of the present disclosure have the following structure:

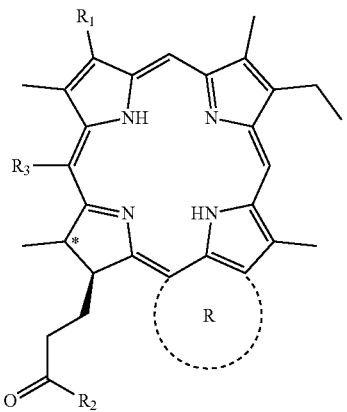

where R is a 5 to 6-member carbocycle or heterocycle (e.g., a heterocycle comprising a nitrogen) with at least one carbonyl or imine, $R_1$ is an linear or branching aliphatic group/moiety (e.g., a vinyl moiety, or alkyl ether), optionally comprising a linker moiety attached to E, $R_2$ is an —OR', —NHR', or —OH, where R' is an aliphatic group/moiety and optionally further comprises a linker moiety attached to E, and $R_3$ is hydrogen or a linker moiety attached to E.

In an example, a compound of the present is disclosure compromises or further comprises a photosensitizer (e.g., a tetrapyrrolic core or reduced tetrapyrrolic core, including but not limited to, derivatives of HPPH), a linker moiety, an erlotinib analog group, and a functional group (e.g., a functional group that is PET active, such as a PET functional group). For example, a compound of the present disclosure is used for PET, fluorescence, and PDT.

In an aspect, the present disclosure provides compositions comprising one or more compound of the present disclosure. The compositions may comprise one or more pharmaceutically acceptable carrier.

In an aspect, the present disclosure provides uses of compounds of the present disclosure. The compounds can be used as imaging agents (e.g., fluorescence imaging agents) or as both imaging and therapeutic agents. In various examples, the present disclosure provides methods that use one or more compounds of the present disclosure. Examples of methods include, but are not limited to, methods of imaging an individual (or a portion thereof) and methods of imaging and treating an individual.

This disclosure provides methods of treating individuals in need of treatment (e.g., for a hyperproliferative disorder, such as, for example, malignancy (e.g., a malignancy disorder)) comprising administering to an individual a compound or composition of the present disclosure, and imaging the individual or a portion thereof and, after staging the disease, proceeding to appropriate therapy (surgical, chemotherapeutic, photodynamic, or standard radiation).

In another aspect, the present disclosure provides kits. In an example, a kit comprises one or more compounds of the present disclosure and/or one or more compositions of the present disclosure and instructions for their use.

BRIEF DESCRIPTION OF THE FIGURES

For a fuller understanding of the nature and objects of the disclosure, reference should be made to the following detailed description taken in conjunction with the accompanying figures.

DETAILED DESCRIPTION OF THE DISCLOSURE

Figure 1:
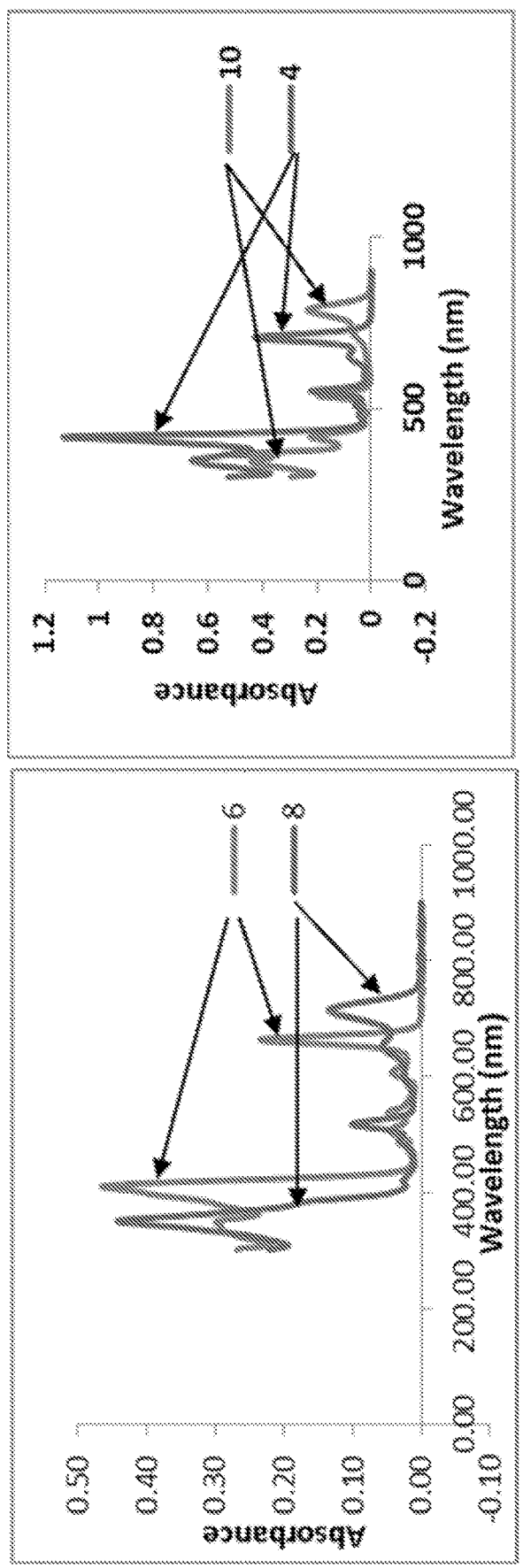
FIG. 1 shows absorption spectra of PS-Erlotinib conjugates in dichloromethane photosensitizers provide an opportunity to treat large and deeply seated tumors (longer the wavelength deeper the tissue penetration of light), and could also limit the number of optical fibers for the PDT treatment, which could make PDT treatment more economical.
Figure 2:
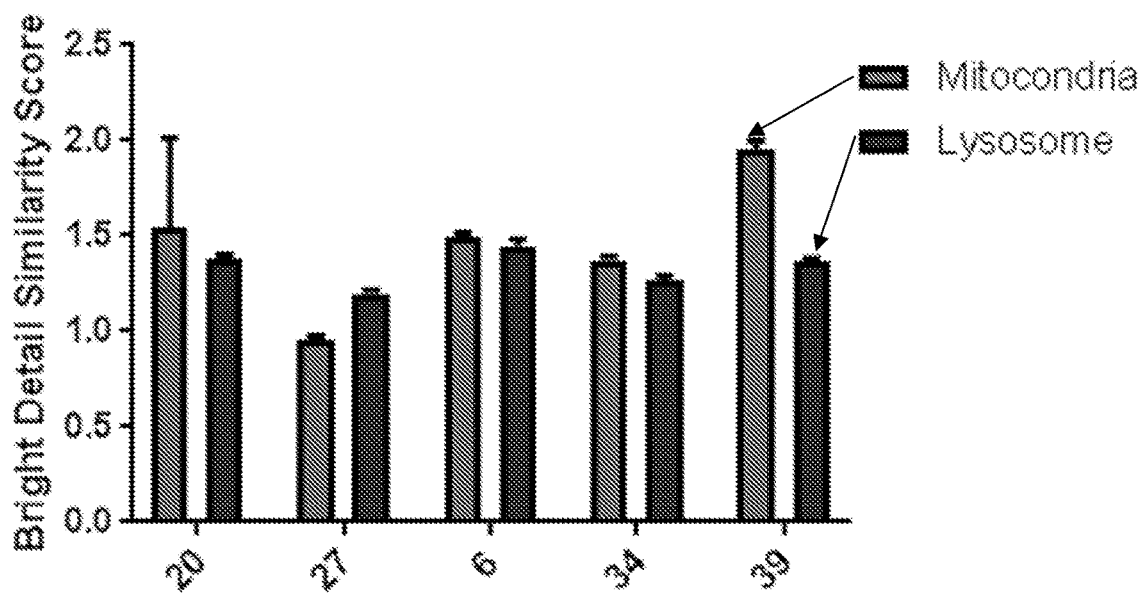
FIG. 2 shows localization of PSs in mitochondria vs. lysosomes in UMUC3 and T24 bladder cancer cell lines.
Figure 2:
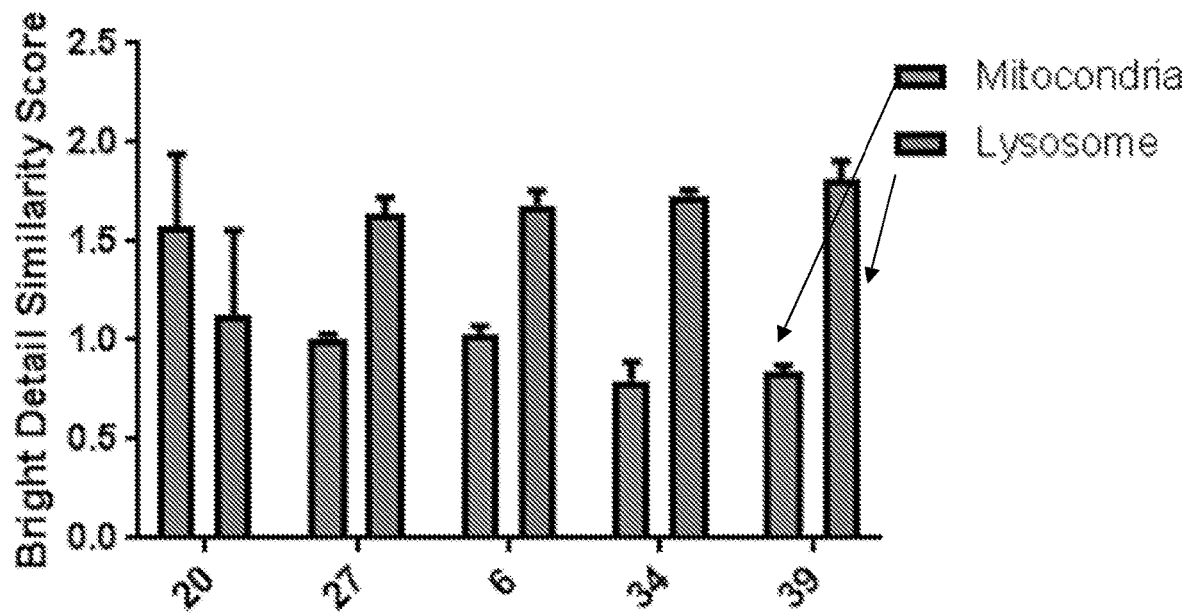

Although claimed subject matter will be described in terms of certain embodiments and examples, other embodiments and examples, including embodiments examples that do not provide all of the benefits and features set forth herein, are also within the scope of this disclosure. Various structural, logical, and process step changes may be made without departing from the scope of the disclosure.

Ranges of values are disclosed herein. The ranges set out a lower limit value and an upper limit value. Unless otherwise stated, the ranges include all values to the magnitude of the smallest value (either lower limit value or upper limit value) and ranges between the values of the stated range.

Units of time can be referred to as follows: hour (h) or (hr), minute (m) or (min), second (s) or (sec).

As used herein, unless otherwise stated, the term "group" refers to a chemical entity that has one terminus that can be covalently bonded to other chemical species. Examples of groups include, but are not limited to:

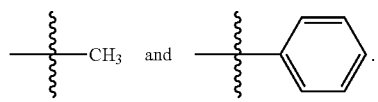

As used herein, unless otherwise stated, the term "moiety" refers to a chemical entity that has two or more termini that can be covalently bonded to other chemical species. Examples of moieties include, but are not limited to:

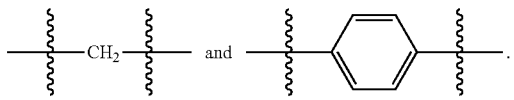

As used herein, unless otherwise indicated, the term "alkyl" refers to branched or unbranched saturated hydrocarbon groups. Examples of alkyl groups include, but are not limited to, methyl groups, ethyl groups, propyl groups, butyl groups, isopropyl groups, tert-butyl groups, and the like. For example, the alkyl group can be a $C_1$ to $C_{12}$, including all integer numbers of carbons and ranges of numbers of carbons therebetween, alkyl group. The alkyl group can be unsubstituted or substituted with one or more substituent. Examples of substituents include, but are not limited to, various substituents such as, for example, halogens (—F, —Cl, —Br, and —I), aliphatic groups (e.g., alkyl groups, alkenyl groups, alkynyl groups), aryl groups, alkoxide groups, carboxylate groups, carboxylic acids, ether groups, and the like, and combinations thereof.

As used herein, unless otherwise indicated, the term "aliphatic" refers to branched or unbranched hydrocarbon groups that, optionally, contain one or more degrees of unsaturation. Degrees of unsaturation include, but are not limited to, alkenyl groups/moieties, alkynyl groups/moieties, and cyclic aliphatic groups/moieties. For example, the aliphatic group can be a $C_1$ to $C_{12}$, including all integer numbers of carbons and ranges of numbers of carbons therebetween, aliphatic group. The aliphatic group can be unsubstituted or substituted with one or more substituent. Examples of substituents include, but are not limited to, various substituents such as, for example, halogens (—F, —Cl, —Br, and —I), additional aliphatic groups (e.g., alkenes, alkynes), aryl groups, alkoxides, carboxylates, carboxylic acids, ether groups, and the like, and combinations thereof.

As used herein, unless otherwise indicated, the term "aryl" refers to $C_5$ to $C_{14}$, including all integer numbers of carbons and ranges of numbers of carbons therebetween, aromatic or partially aromatic carbocyclic groups. The aryl group can comprise polyaryl moieties such as, for example, fused rings or biaryl moieties. The aryl group can be unsubstituted or substituted with one or more substituent. Examples of substituents include, but are not limited to, various substituents such as, for example, halogens (—F, —Cl, —Br, and —I), aliphatic groups (e.g., alkenes, alkynes), aryl groups, alkoxides, carboxylates, carboxylic acids, ether groups, and the like, and combinations thereof. Examples of aryl groups include, but are not limited to, phenyl groups, biaryl groups (e.g., biphenyl groups), and fused ring groups (e.g., naphthyl groups).

As used herein, unless otherwise indicated, the term "photosensitizer" (PS) refers to a photosensitizing group/moiety. In an example, PS is a tetrapyrrolic group/moiety and/or a reduced tetrapyrrolic group/moiety. A non-limiting example is a group/moiety derived from HPPH (2-(1-Hexyloxyethyl)-2-devinyl pyropheophorbide-a) or Photobac (3-(1'-butyloxy)ethyl-3-deacetyl-bacteriopurin-18-N-butylimide methyl ester).

As used herein, unless otherwise indicated, the term "linker" or "linker moiety" refers to a moiety connecting a PS to an E. In an example, the linker or linker moiety is an aliphatic aryl moiety connected to a PS through a carbon-nitrogen bond (e.g., an amide bond) or carbon-carbon bond, and the linker moiety is further connected to an E through an $sp^1$ carbon-$sp^2$ aryl carbon bond or $sp^2$ triazole carbon-$sp^2$ aryl carbon bond. In another example, the linker moiety is an aliphatic group connected to a PS through a carbon-nitrogen bond (e.g., an amide bond), and the linker moiety is further connected to an E through a nitrogen-carbon bond (e.g., an amide bond). In another example, the linker moiety comprises a disulfide bond. In such an example, a PS is connected to the linker moiety via a carbon-nitrogen bond (e.g., an amide bond) or a carbon-sulfur bond (e.g., a thioester bond), and the linker moiety is connect to an E through a nitrogen-carbon bond (e.g., an amide bond) or a sulfur carbon bond (e.g., a thioester bond). In such an example, the linker moiety can be cleaved at the disulfide bond when the compound is in a reducing environment (e.g., the local environment of a tumor). Examples of linkers include, but are not limited to,

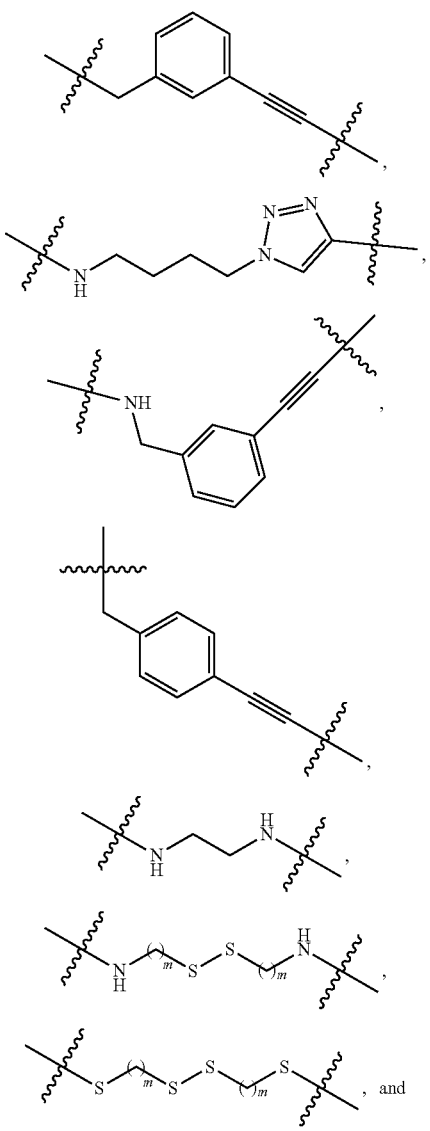

-continued

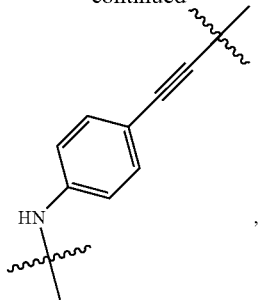

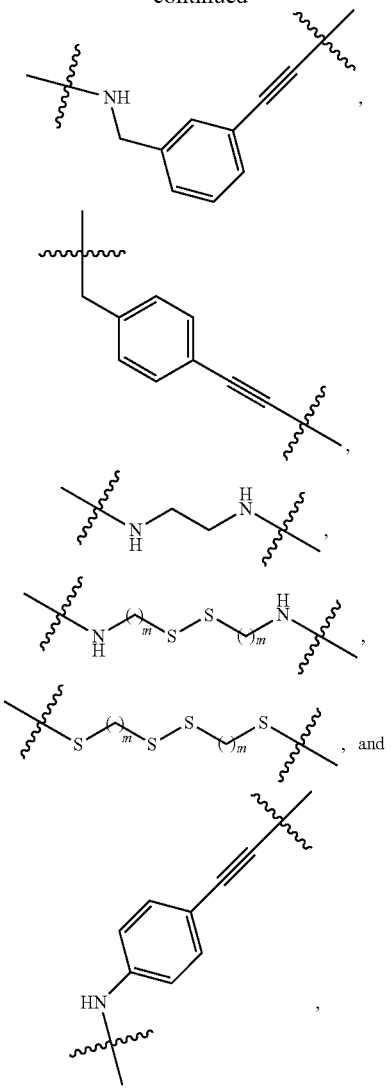

where m is 1, 2, 3, 4, 5, 6, 7, 8, 9, or 10, including all ranges therebetween.

In an aspect, the present disclosure describes compounds compromising a photosensitizer (PS) (e.g., a tetrapyrrolic group/moiety or reduced tetrapyrrolic group/moiety, such as, for example, but not limited to, a group/moiety derived from HPPH), a linker moiety, and erlotinib or erlotinib analog groups. Such a compound has the following structure: PS-L-E, where PS is a photosensitizer group or moiety (e.g., a tetrapyrrolic group or moiety, such as, for example, but not limited to, derived from HPPH)), L is a linker moiety, and E is an erlotinib group or moiety or an erlotinib analog group. The compounds are asymmetric compounds. The compounds target EGFR and can have desirable specificity (e.g., tumor specificity and/or cellular specificity) and tumor retention.

As used herein, unless otherwise indicated, the term "linker" or "linker moiety" refers to a moiety connecting a PS to an E. In an example, the linker or linker moiety is an aliphatic aryl moiety connected to a PS through a carbon-nitrogen bond (e.g., an amide bond) or carbon-carbon bond, and the linker moiety is further connected to an E through an $sp^1$ carbon-$sp^2$ aryl carbon bond or $sp^2$ triazole carbon-$sp^2$ aryl carbon bond. In another example, the linker moiety is an aliphatic group connected to a PS through a carbon-nitrogen bond (e.g., an amide bond), and the linker moiety is further connected to an E through a nitrogen-carbon bond (e.g., an amide bond). In another example, the linker moiety comprises a disulfide bond. In such an example, a PS is connected to the linker moiety via a carbon-nitrogen bond (e.g., an amide bond) or a carbon-sulfur bond (e.g., a thioester bond), and the linker moiety is connect to an E through a nitrogen-carbon bond (e.g., an amide bond) or a sulfur carbon bond (e.g., a thioester bond). In such an example, the linker moiety can be cleaved at the disulfide bond when the compound is in a reducing environment (e.g., the local environment of a tumor). Examples of linkers include, but are not limited to,

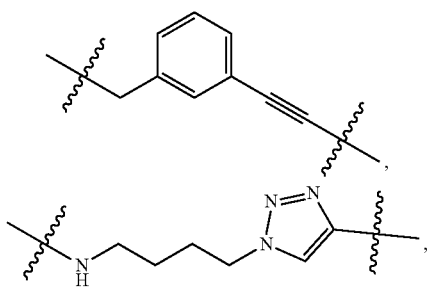

where m is 1, 2, 3, 4, 5, 6, 7, 8, 9, or 10, including all ranges therebetween.

Erlotinib, an inhibitor of the epidermal growth factor receptor (EGFR), has been approved by different health organizations for treating a variety of EGFR-overexpressed cancers (e.g., head & neck, bladder, ovarian, thyroid, lung etc.). In order to potentiate the therapeutic application of erlotinib by enabling the photochemical destruction of erlotinib-target cells, erlotinib was conjugated to photosensitizer derived from chlorophyll-a and bacteriochlorophyll-a (near-infrared agents). The resulting conjugates were tested for the optimal cell-uptake, cell-specificity in 3D culture systems, photodynamic efficacy, photo-induced STAT3 dimerization (a biomarker of photodynamic therapy) and EGFR signal inhibition study in EGFR-positive head and neck and bladder cancers. It was discovered that in contrast to symmetrical PS, an asymmetrical PS (e.g., PSs of the present disclosure, such as chlorin and bacteriochlorin-based PS), the position of the EGFR targeting moiety (EGFR inhibitor), nature of linker(s) joining the two moieties and overall lipophilicity of the molecule make an unexpected difference in EGFR target specificity and retention in tumor.

Non-limiting examples of erlotinib analog groups include:
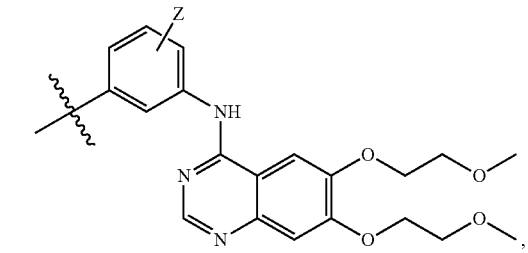
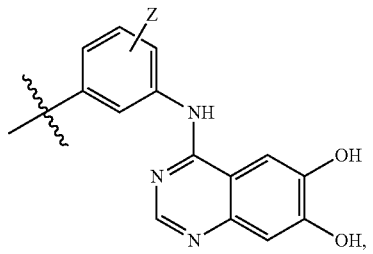
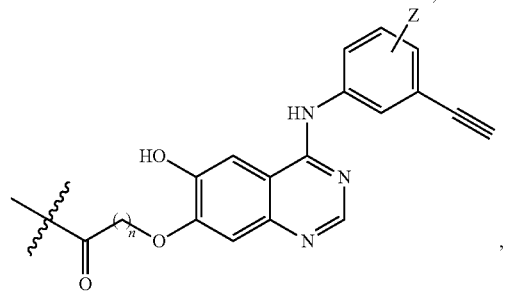
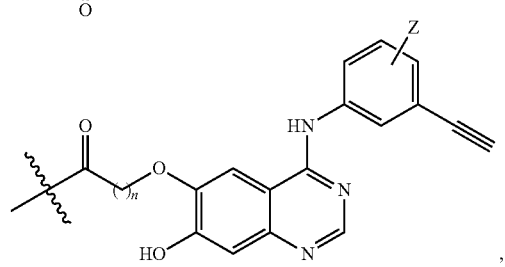
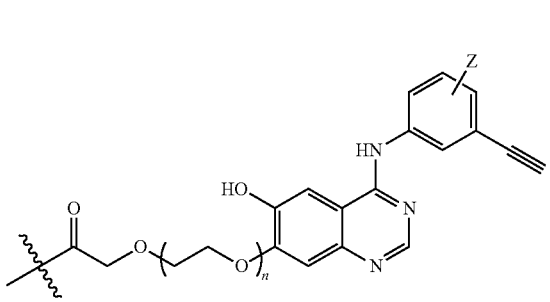
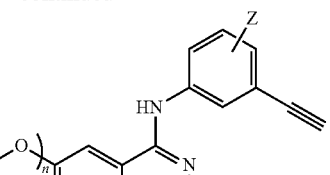
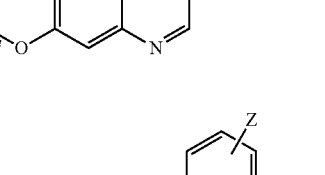
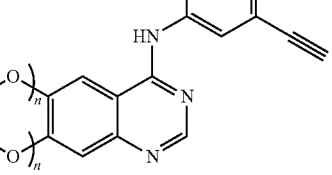
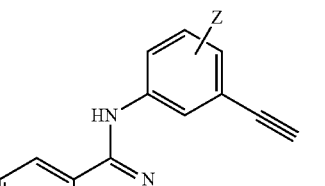
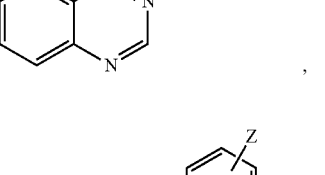
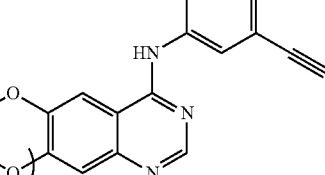
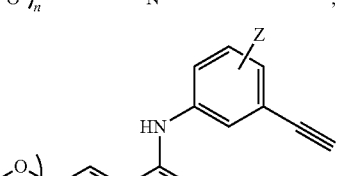
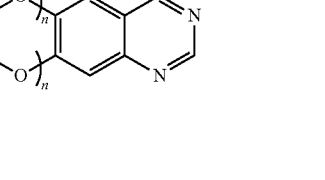
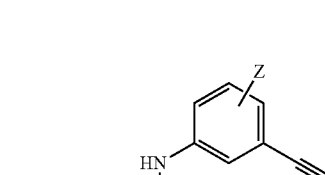
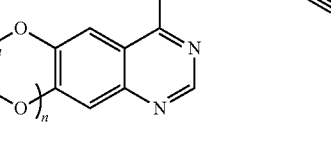

-continued

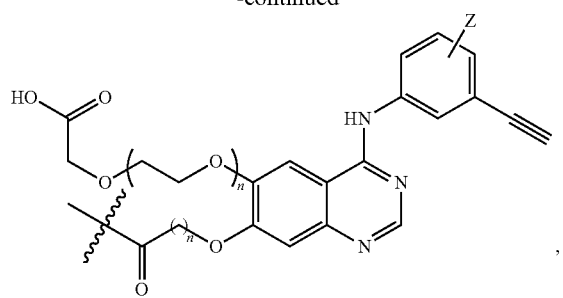
,

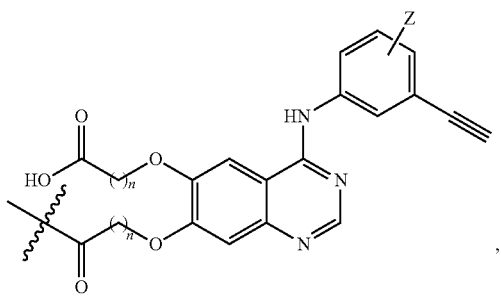
,

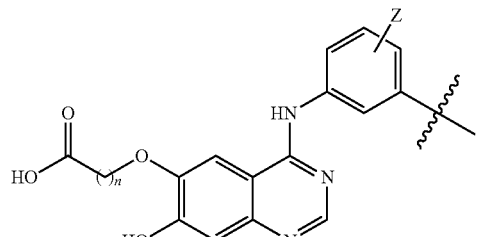
,

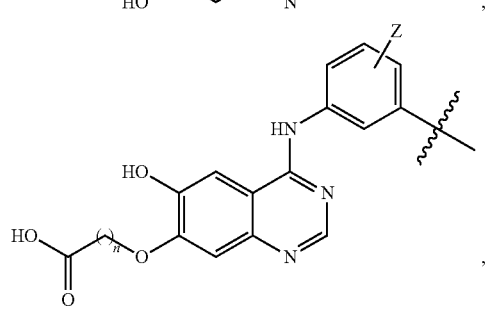
,

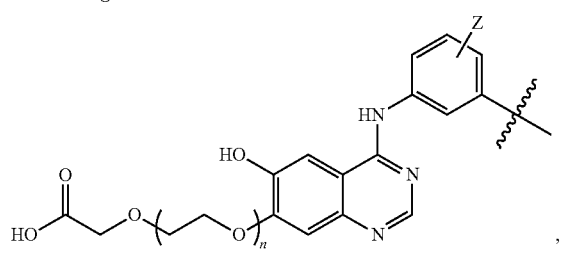
,

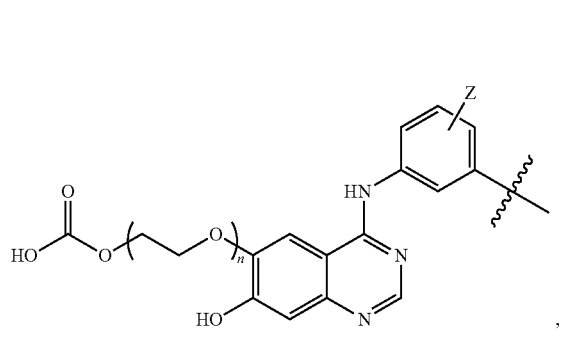
,

-continued

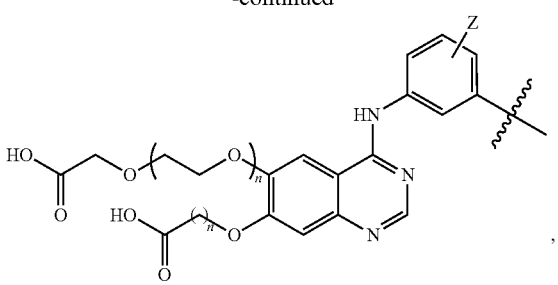
,

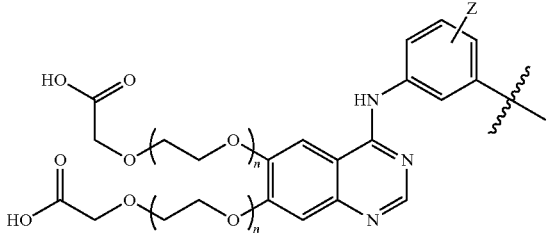
,

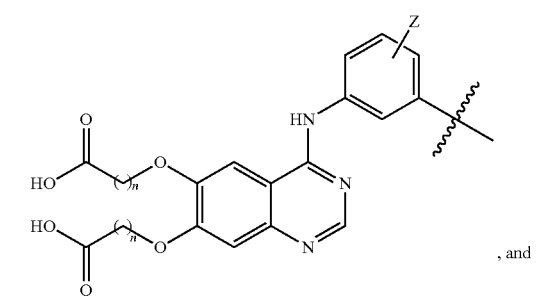
, and

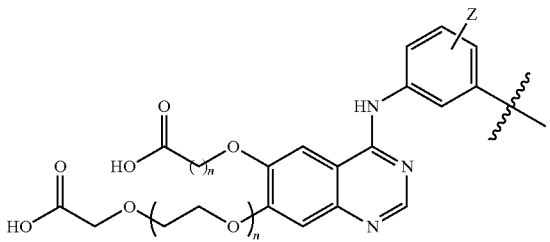
, where n is 1, 2, 3, 4, 5, or 6, including all ranges therebetween, and Z is hydrogen, an electron withdrawing group, a deactivating group, or a combination thereof. Non-limiting examples of electron withdrawing groups and/or deactivating groups include halogens (fluorine, bromine, iodine, chlorine), nitro groups, cyano groups, trihalides (e.g., trifluoromethyl and the like), sulfonates, ammonium groups, aldehydes, carboxyl groups, acyl chlorides, and combinations thereof.

In an example, compounds of the present disclosure have the following structure:

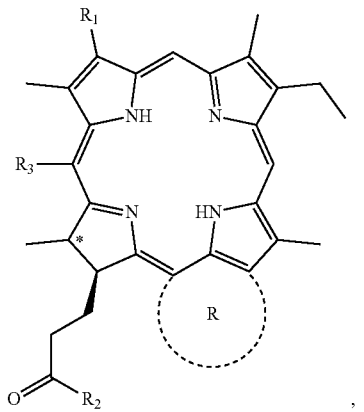

where R is a 5 to 6-member carbocycle or heterocycle (e.g., a heterocycle comprising a nitrogen) with at least one carbonyl or imine, $R_1$ is an linear or branching aliphatic group/moiety (e.g., a vinyl moiety, or alkyl ether), optionally comprising a linker moiety attached to E, $R_2$ is an —OR', —NHR', or —OH, where R' is an aliphatic group/moiety and optionally further comprises a linker moiety attached to E, and $R_3$ is hydrogen or a linker moiety attached to E.

In an example, compounds of the present disclosure have the following structure:

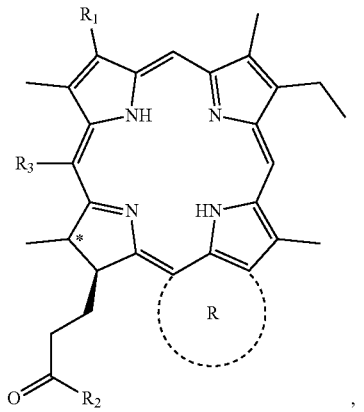

where R is

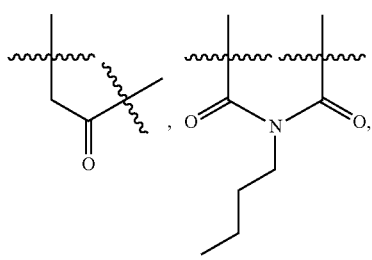

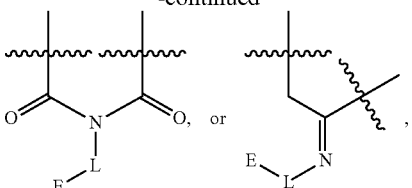

$R_1$ is

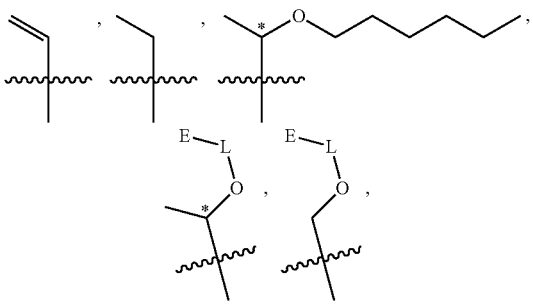

$R_2$ is —OH, —OCH$_3$, or L—E, $R_3$ is H or

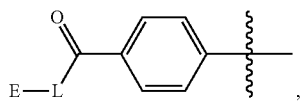

L is a linking moiety selected from the group consisting of:

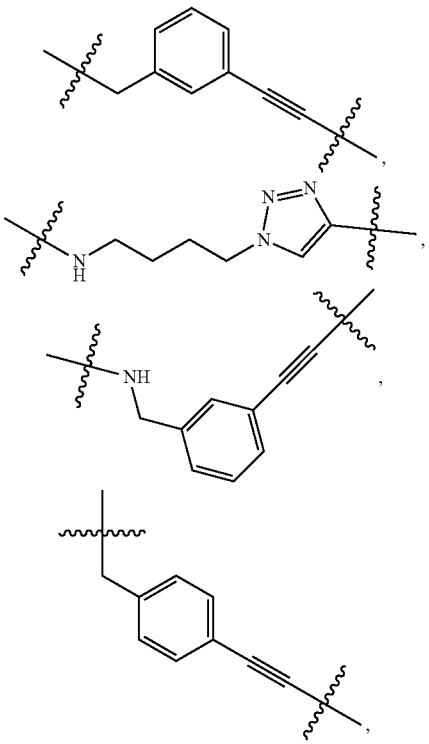

-continued
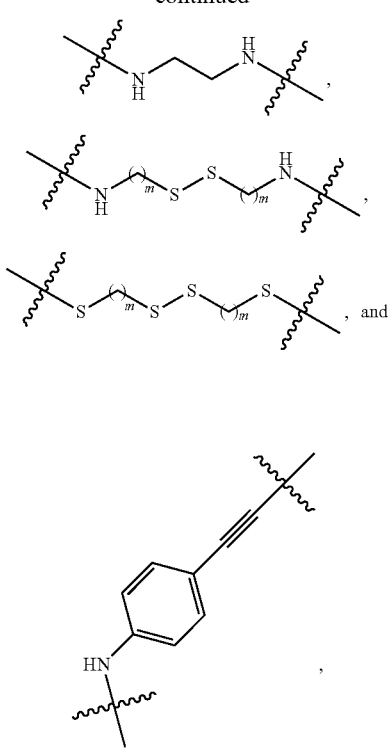
where m is 1, 2, 3, 4, 5, 6, 7, 8, 9, or 10, including all ranges therebetween,
E is selected from the group consisting of:
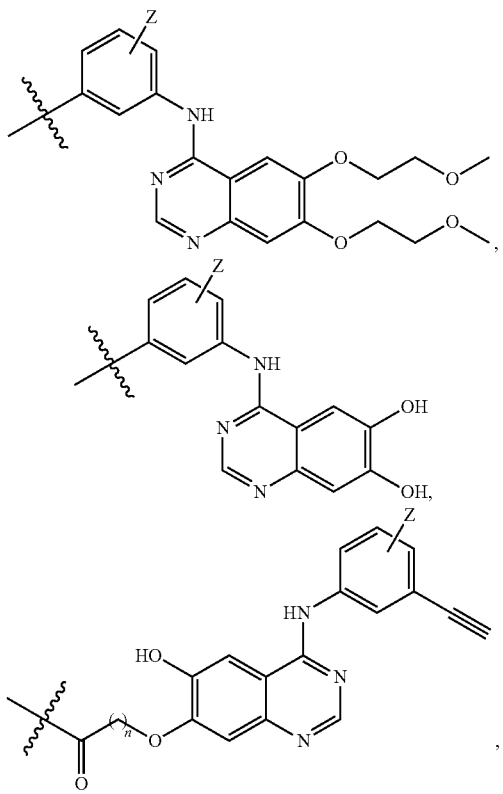
-continued
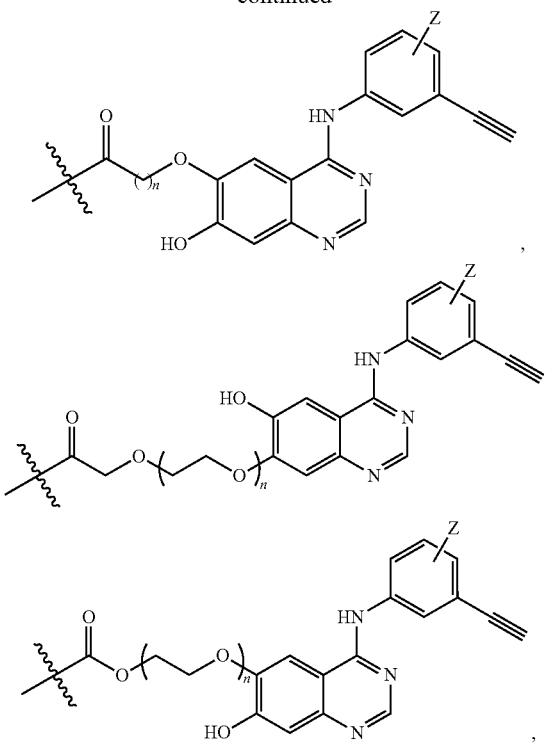

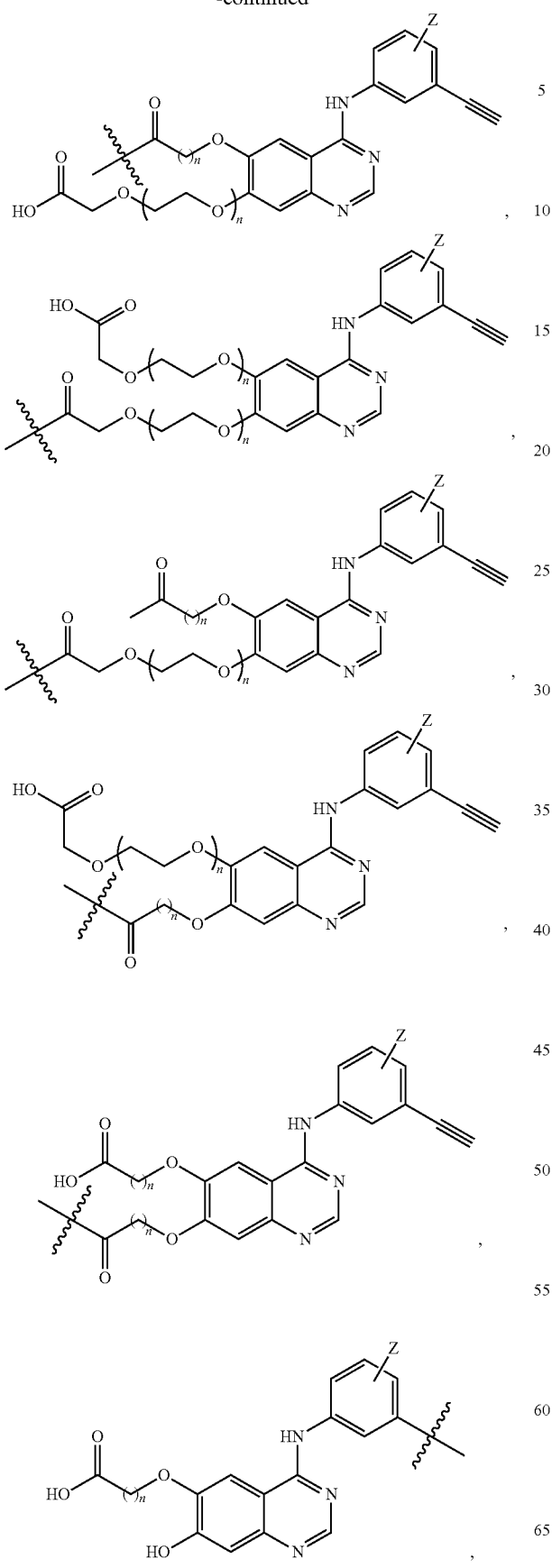
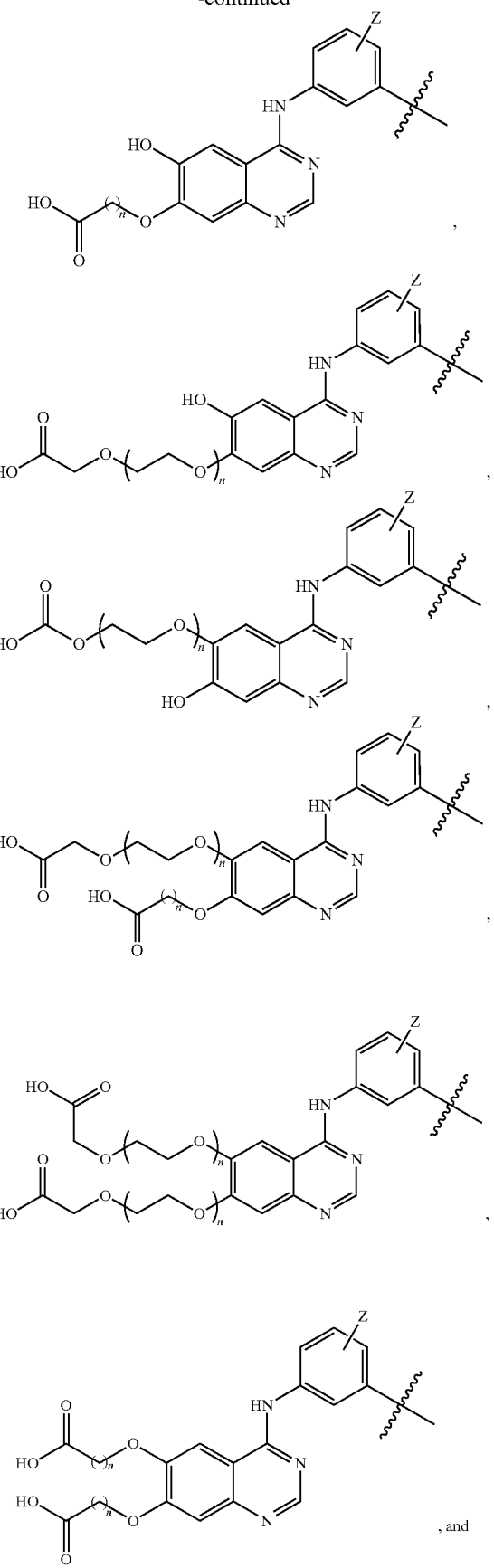
, and

-continued

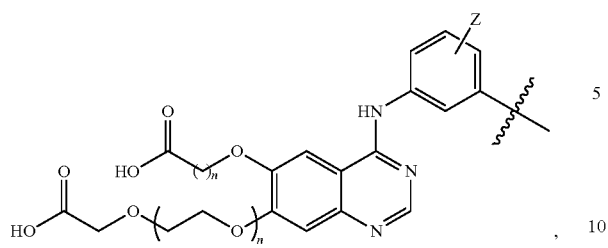

where n is 1, 2, 3, 4, 5, or 6, including all ranges therebetween, Z is hydrogen, an electron withdrawing group, a deactivating group, or a combination thereof, and where at each instance of the asterisk represents a chiral center (e.g., R or S chirality).

Compounds of the present disclosure can comprise an erlotinib analog group attached to a linker moiety attached to the lower half of the photosensitizer. For example, compounds can have the following structure:

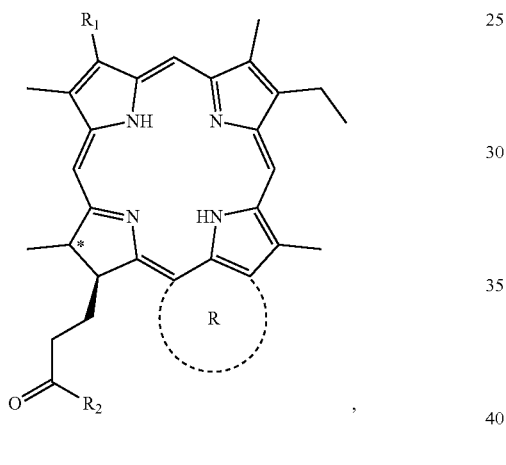

where R is

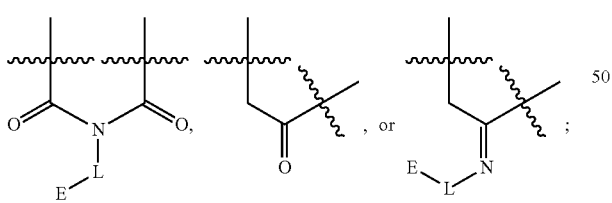

$R_1$ is

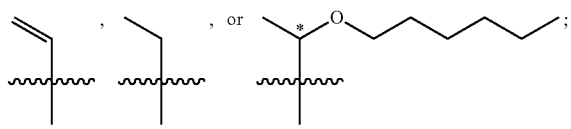

$R_2$ is —OH, —OCH$_3$, or L—E,

L is a linker moiety selected from the group consisting of:

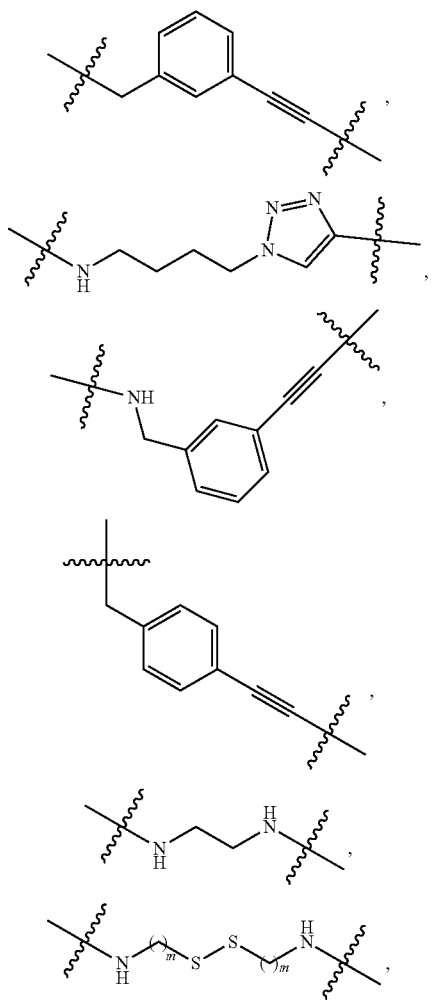

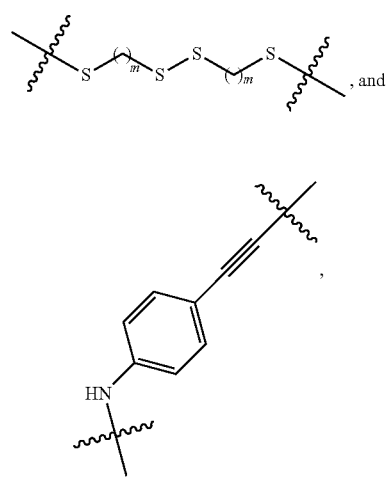

where m is 1, 2, 3, 4, 5, 6, 7, 8, 9, or 10, including all ranges therebetween, including all integers and ranges therebetween, E is selected from the group consisting of
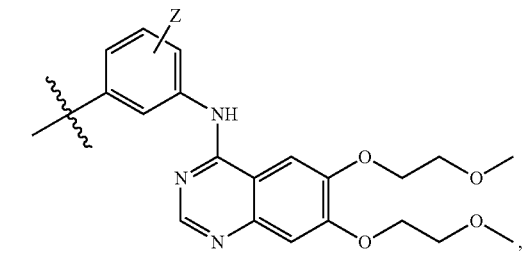
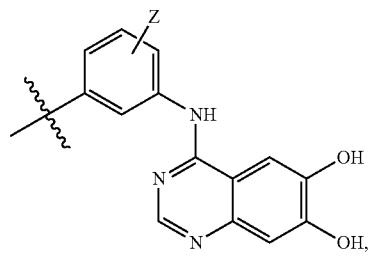
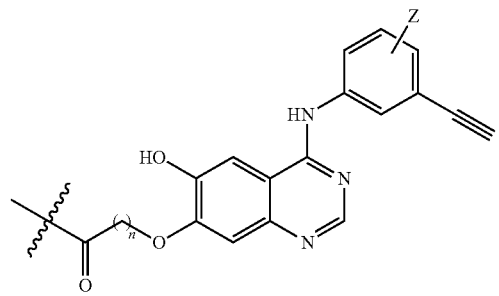
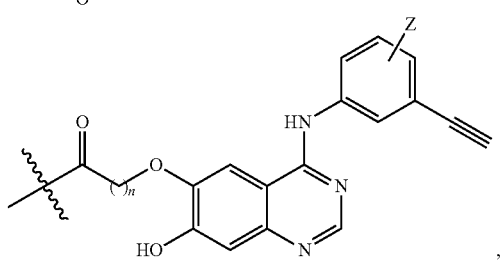
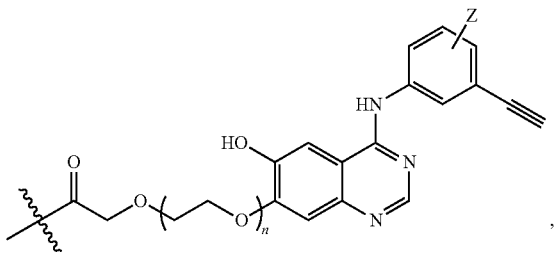
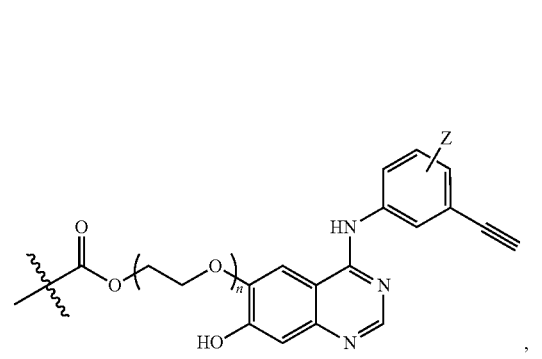
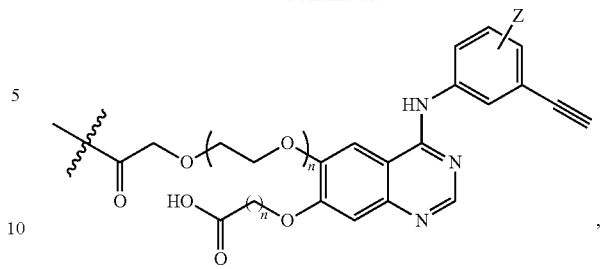
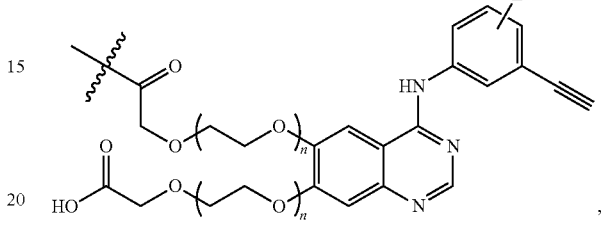
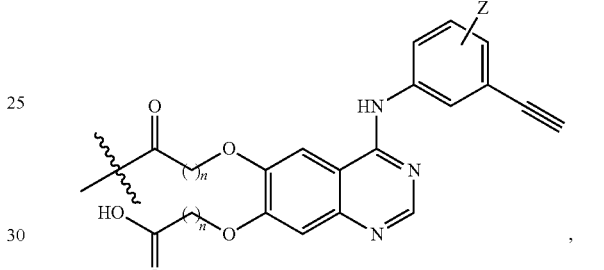
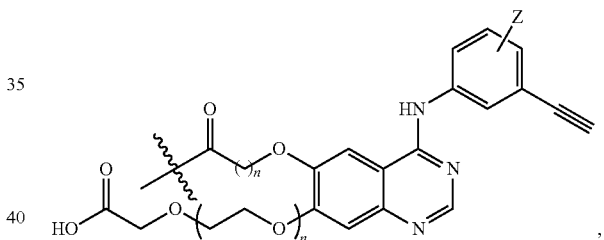
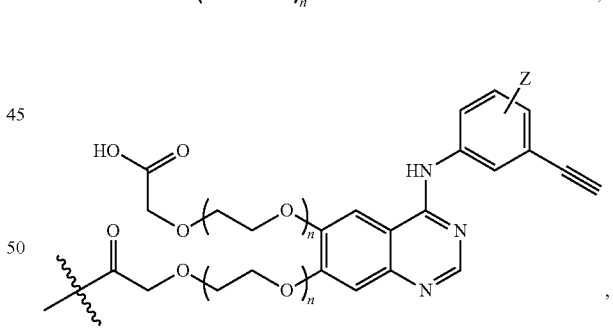
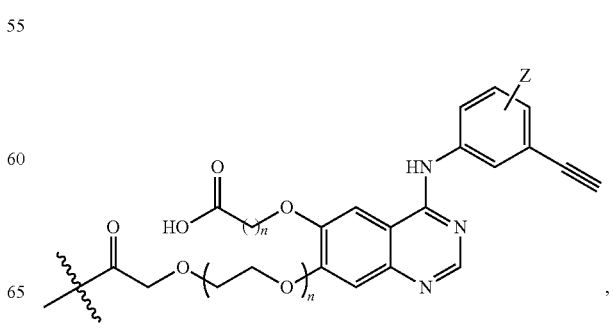

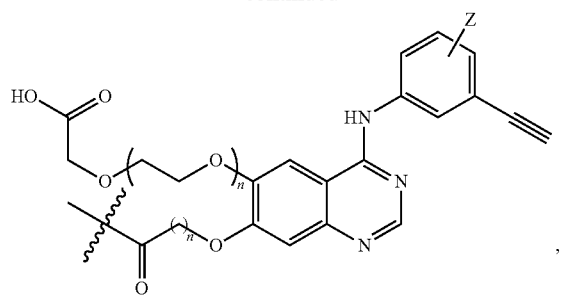

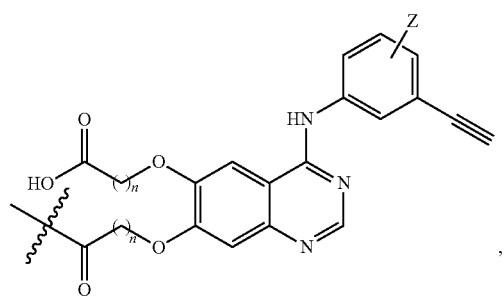

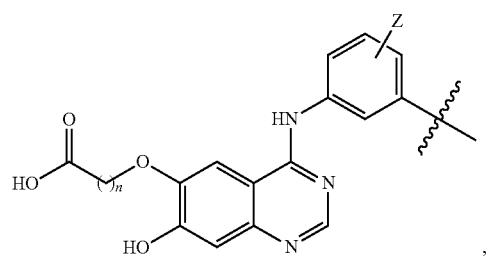

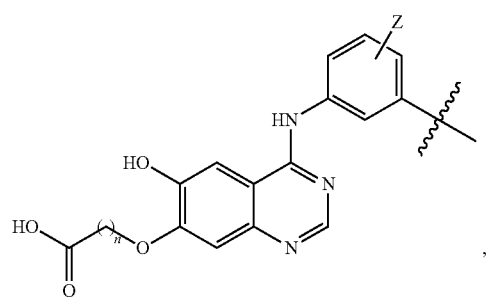

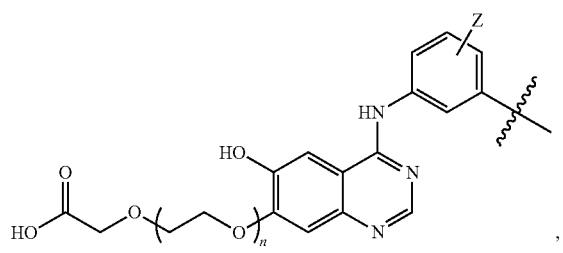

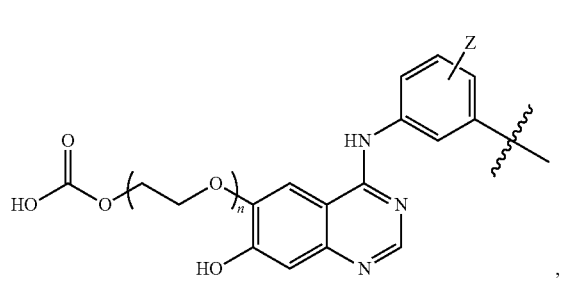

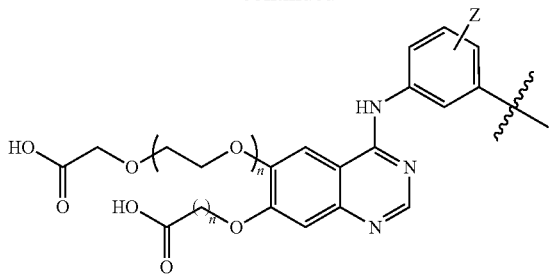

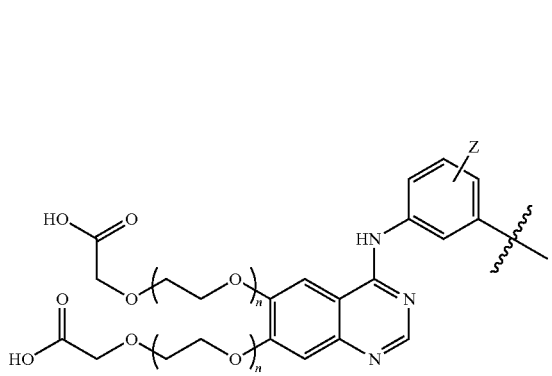

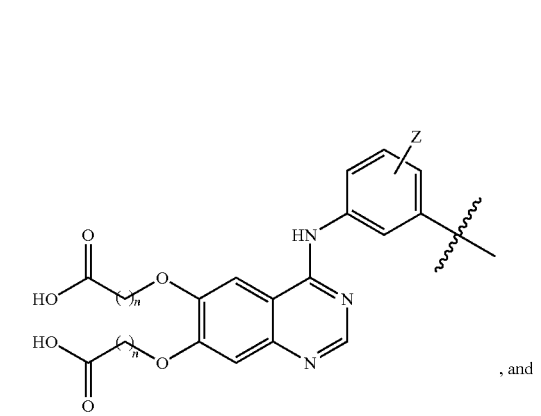

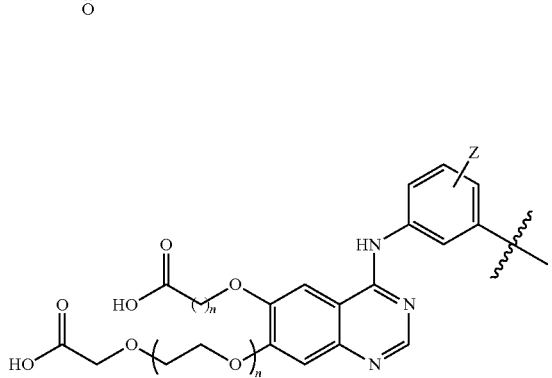

, and where where n is 1, 2, 3, 4, 5, or 6, including all ranges therebetween, and Z is hydrogen, an electron withdrawing group, a deactivating group, or a combination thereof, and where at each instance of the asterisk represents a chiral center (e.g., R or S chirality).

The erlotinib analog group can be attached to the linker moiety through a carbon-nitrogen bond (e.g., an amide bond) or through a carbon-sulfur bond (e.g., a thioester bond). Non-limiting examples of the compound include:

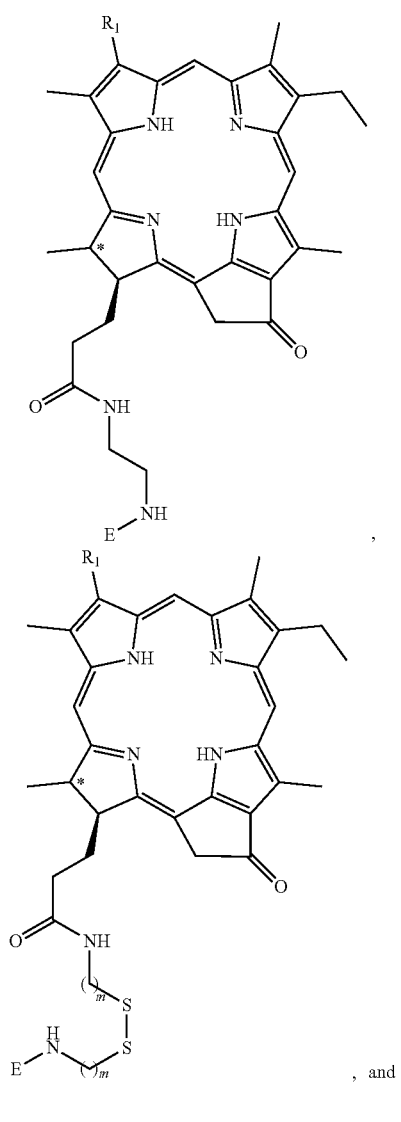
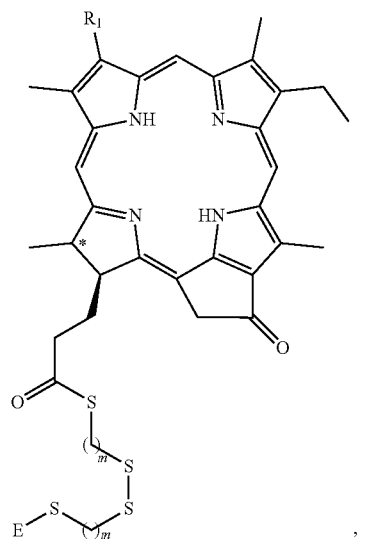
, and
$R_1$ is
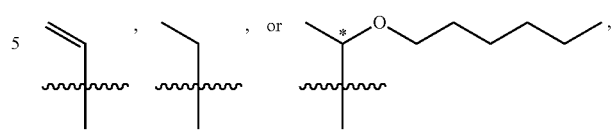
E is selected from the group consisting of:
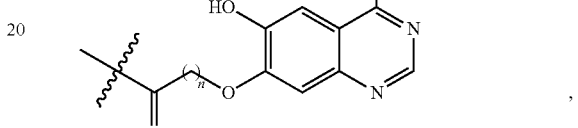
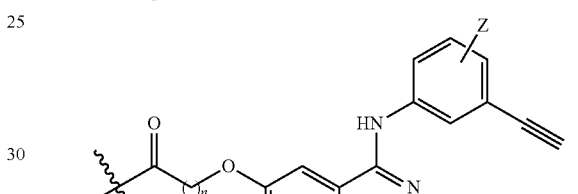
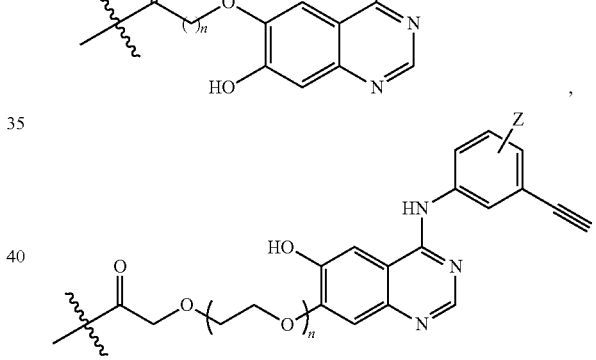
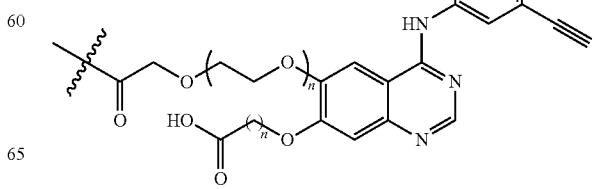

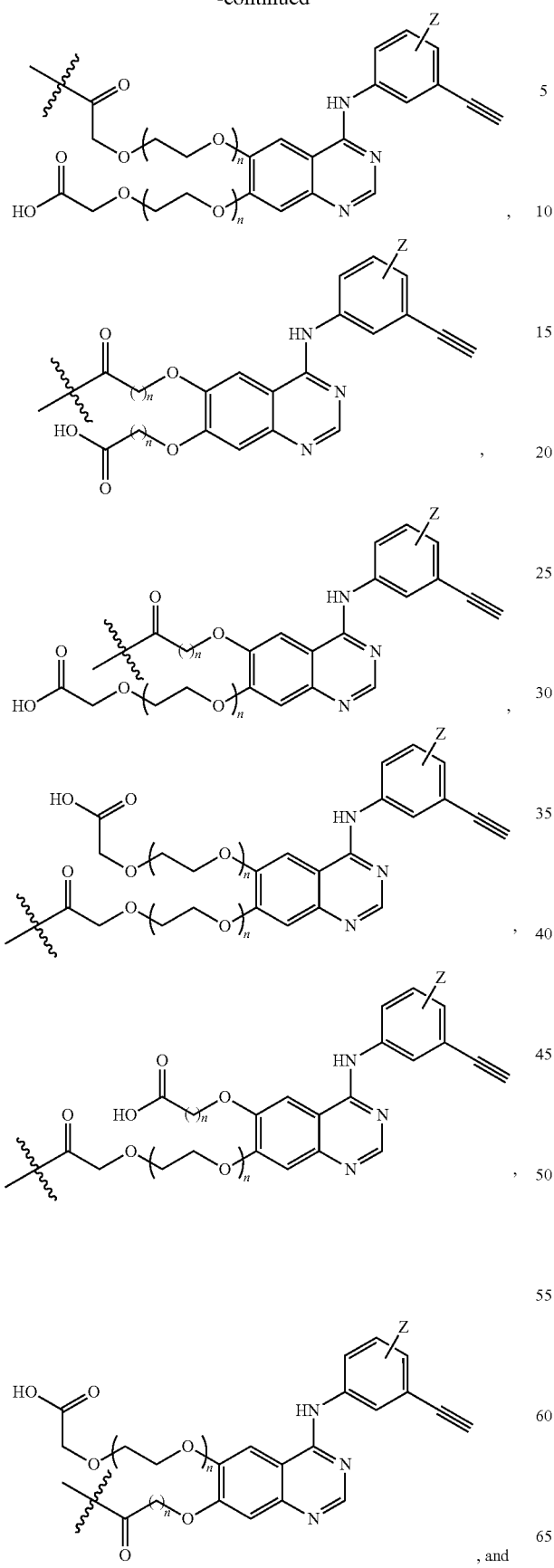

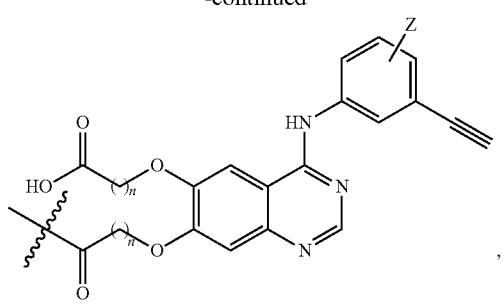

where n is 1, 2, 3, 4, 5, or 6, including all ranges therebetween, and Z is hydrogen, an electron withdrawing group, a deactivating group, or a combination thereof, and each instance of the asterisk represents a chiral center (e.g., R or S chirality).

In an example, compounds of the present disclosure comprise an erlotinib analog groups attached to a linker moiety attached to the upper half of the photosensitizer. Compositions of such an example have the following structure:

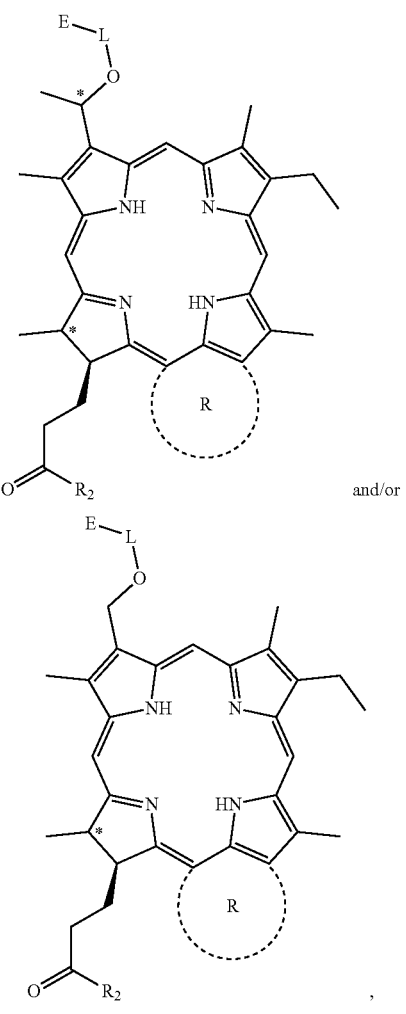

where R is
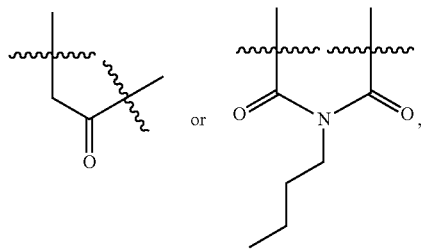 [SMILES: *CC(*)=O ; *C(=O)N(CCCC)C(*)=O] or 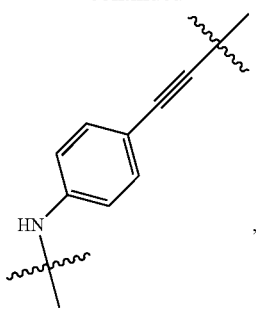
$R_2$ is —OH or —OCH$_3$,
L is a linker moiety selected from the group consisting of:
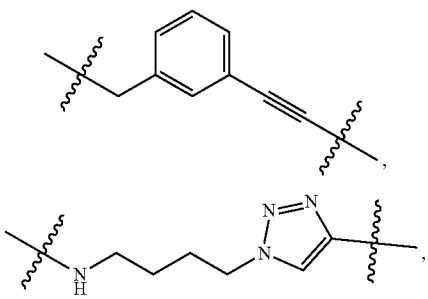
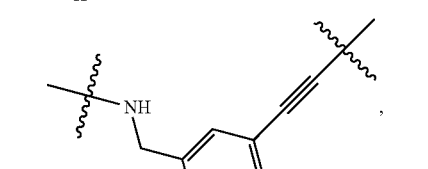
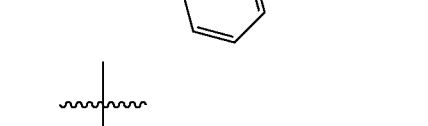
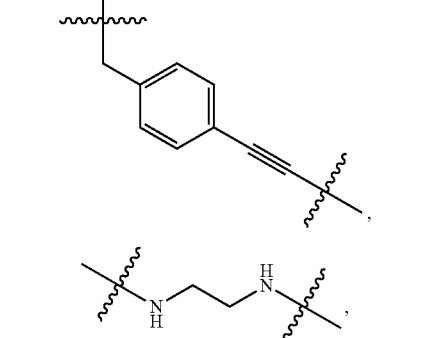
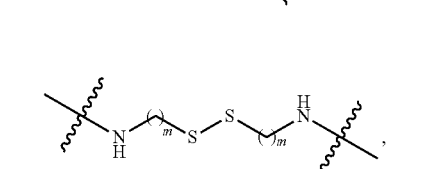
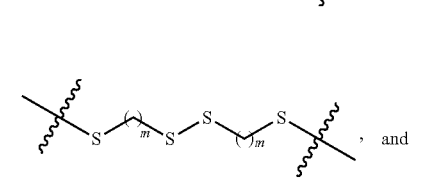, and
where m is 1-10, including all integers and ranges therebetween
E is selected from the group consisting of:
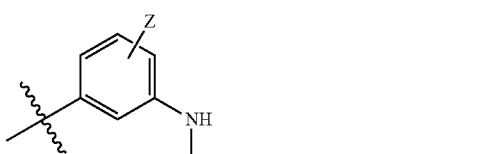
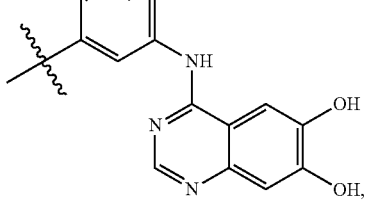
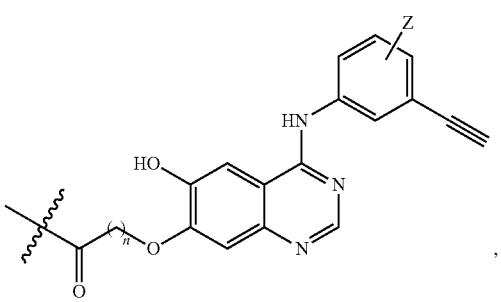
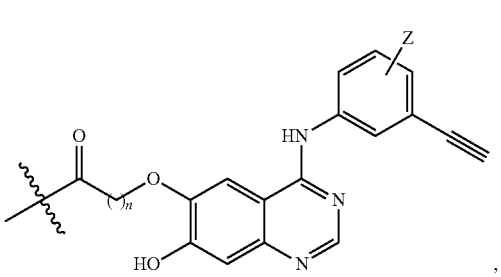

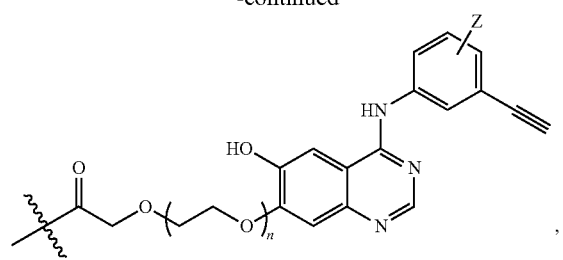
,
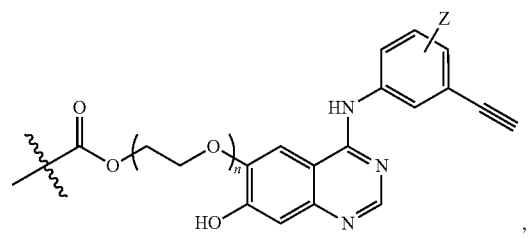
,
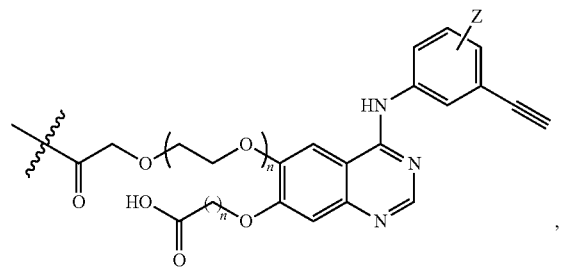
,
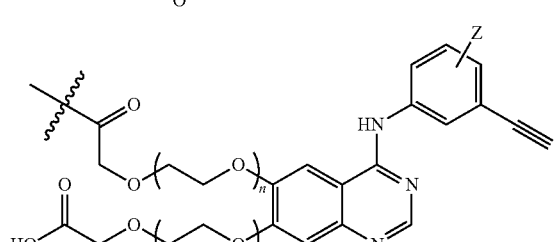
,
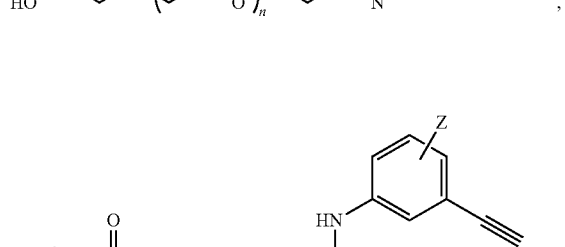
,
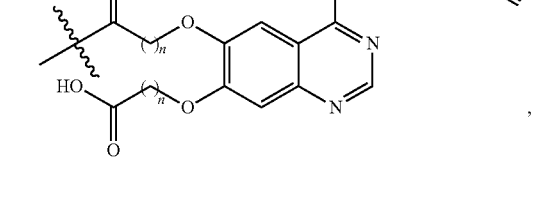
,
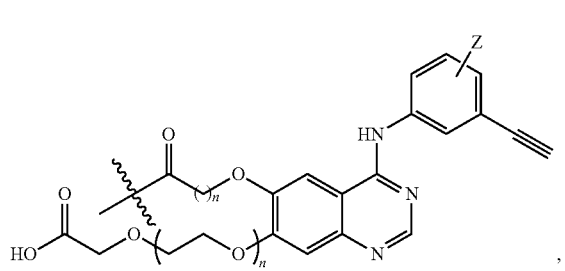
,
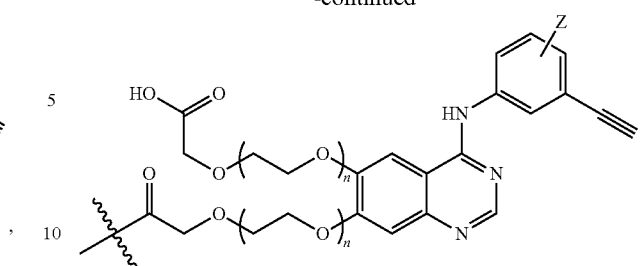
,
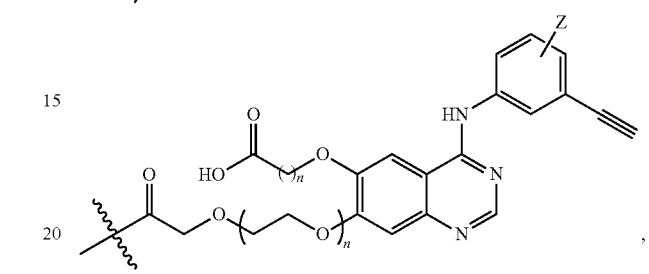
,
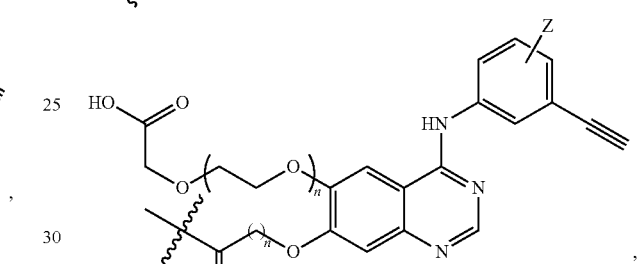
,
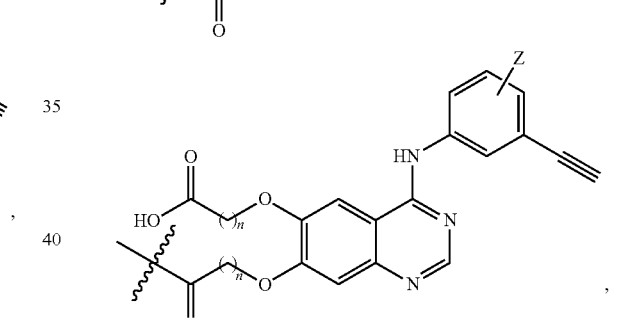
,
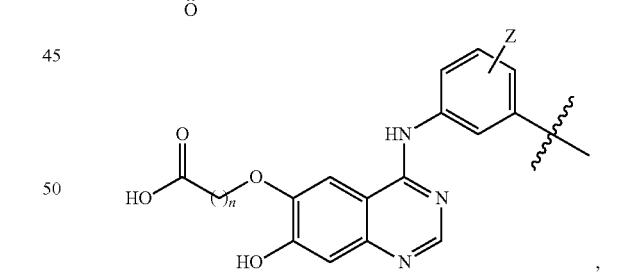
,
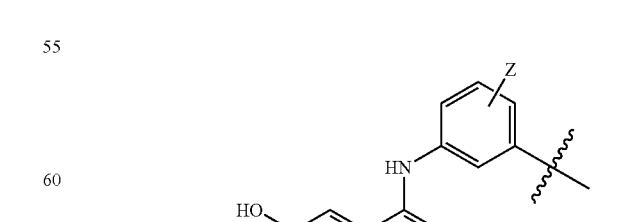
, -continued

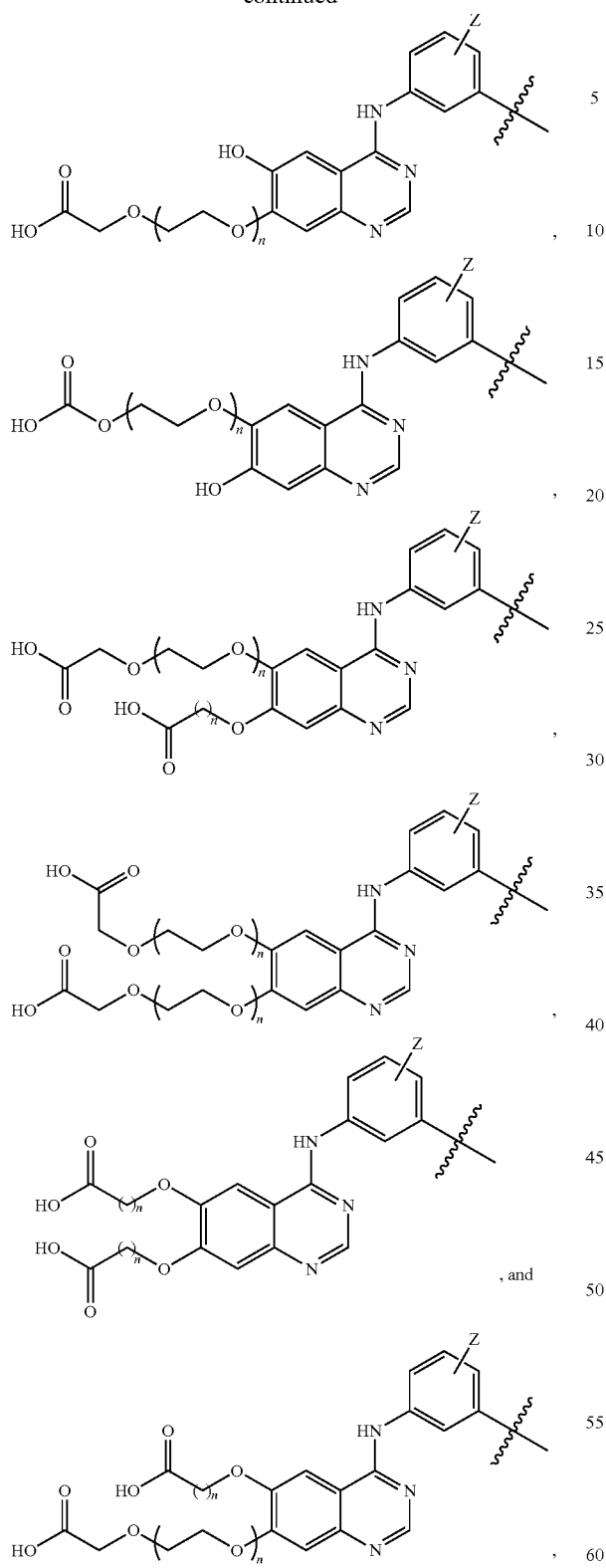

where where n is 1, 2, 3, 4, 5, or 6, including all ranges therebetween, and Z is hydrogen, an electron withdrawing group, a deactivating group, or a combination thereof, and where at each instance the asterisk represents a chiral center (e.g., R or S chirality).

The erlotinib analog group can be attached to the linker moiety through an sp$^2$ aryl carbon-s$^1$ carbon bond or through an sp$^2$ triazole carbon-sp$^2$ aryl carbon bond. Non-limiting examples of the compound include:

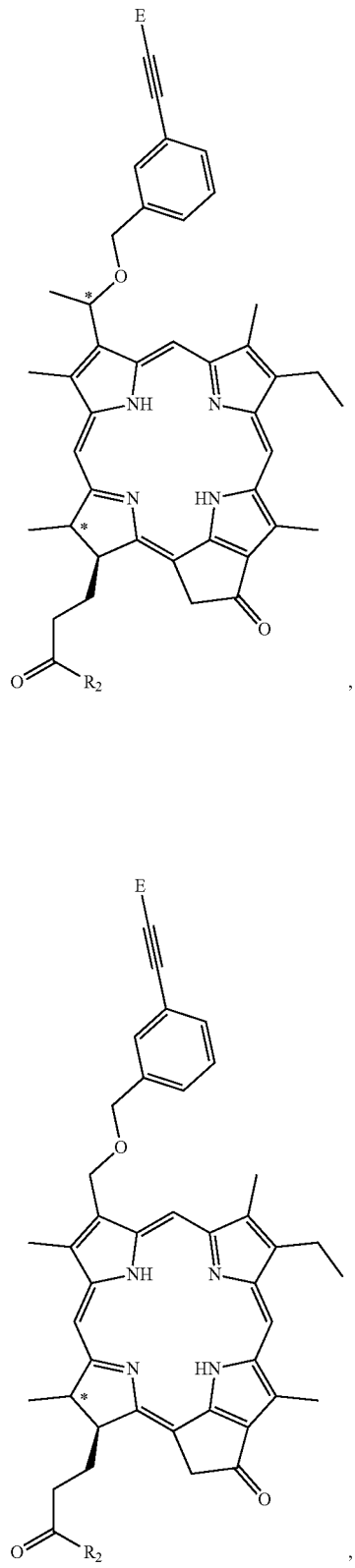

-continued
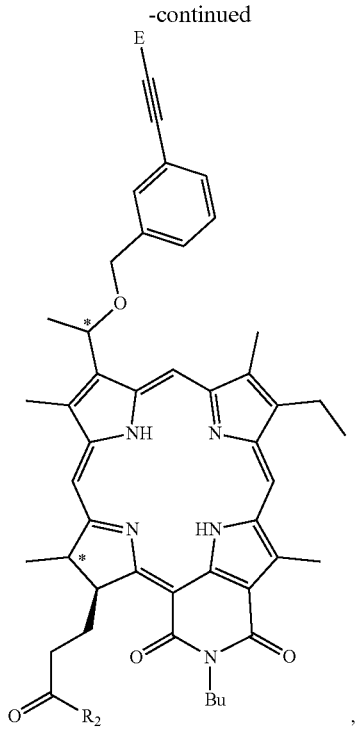
, and
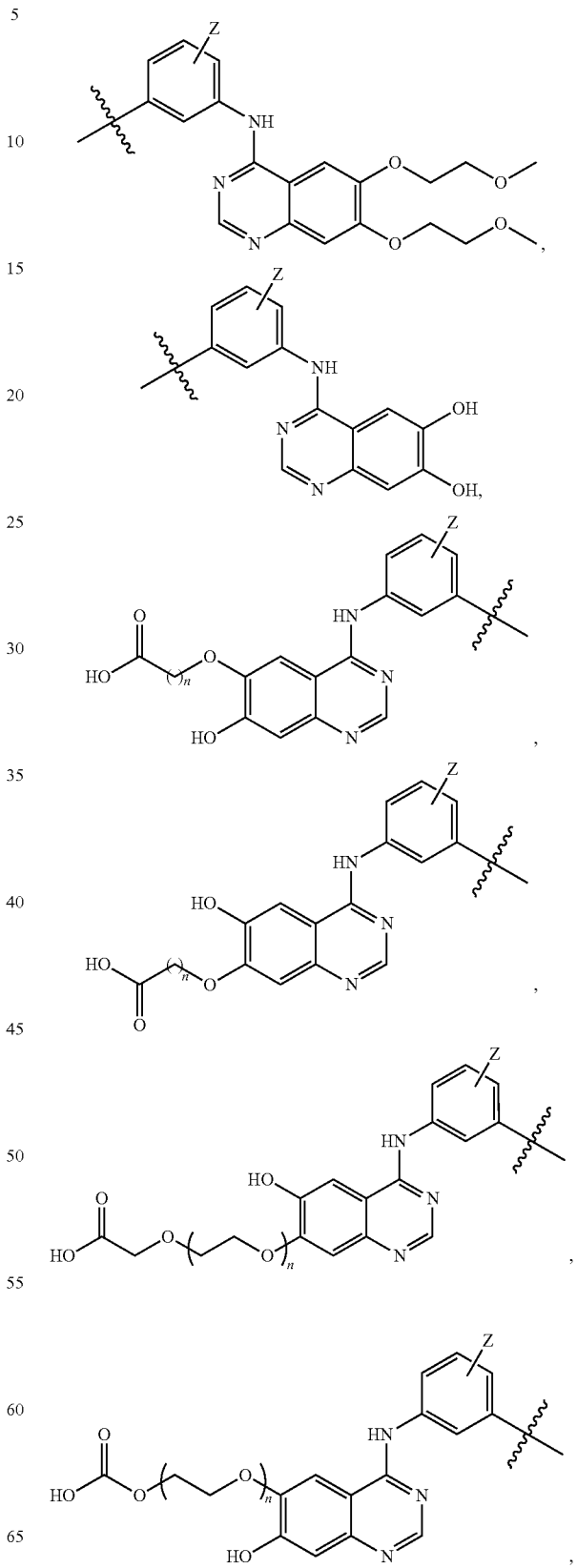
where R₂ is hydrogen or —OCH₃,
E is selected from the group consisting of:

-continued

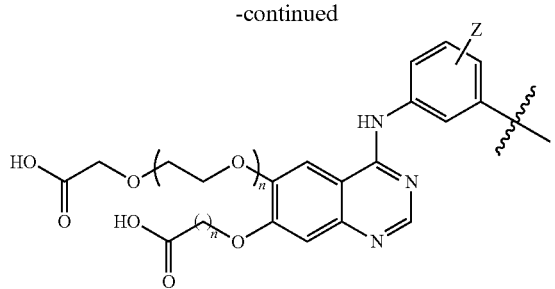

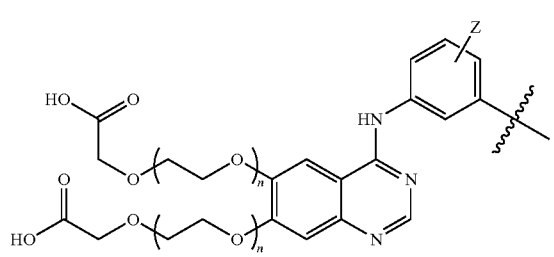

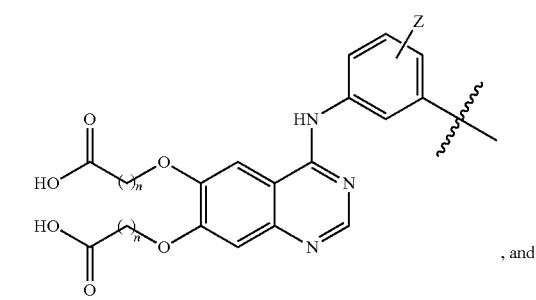

, and

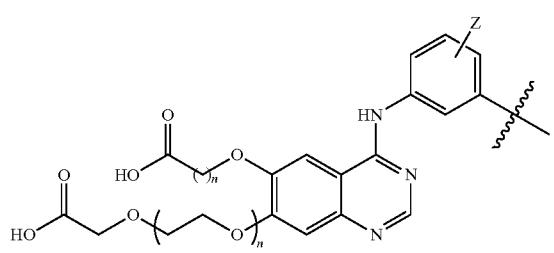

where where n is 1, 2, 3, 4, 5, or 6, including all ranges therebetween, and Z is hydrogen, an electron withdrawing group, a deactivating group, or a combination thereof, and where at each instance of the asterisk is a chiral center (e.g., R or S chirality).

In an example, compounds of the present disclosure comprise an erlotinib analog group attached to a linker moiety attached to position 20 of a porphyrin photosensitizer (e.g., a tetrapyrrolic core or reduced tetrapyrrolic core, such as, but not limited to, derivates of HPPH). In such an example, the composition has the following structure:

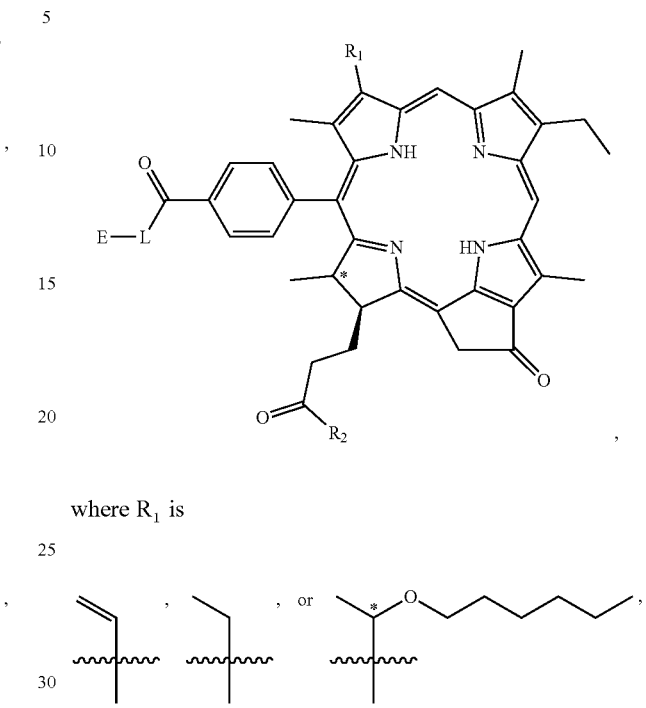

where $R_1$ is

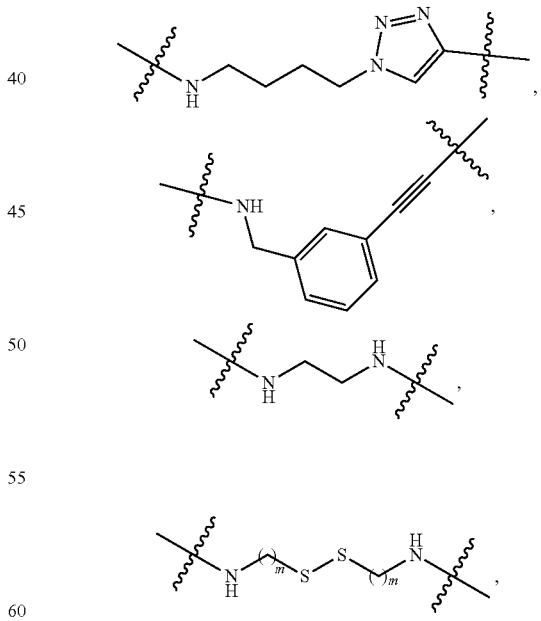

, or $R_2$ is —OH or —OCH$_3$,

L is a linker moiety selected from the group consisting of:

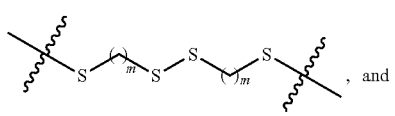

, and

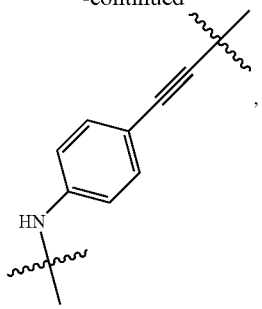
m is 1, 2, 3, 4, 5, 6, 7, 8, 9, or 10, including all ranges therebetween,
E is selected from the group consisting of:
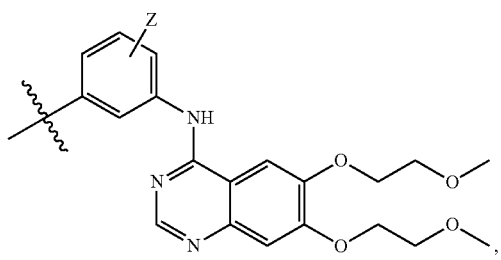
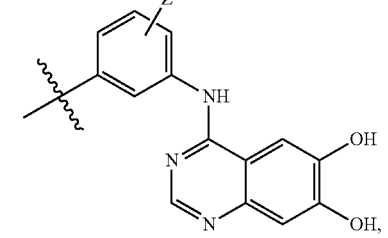
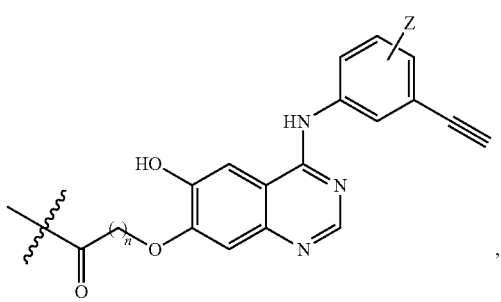
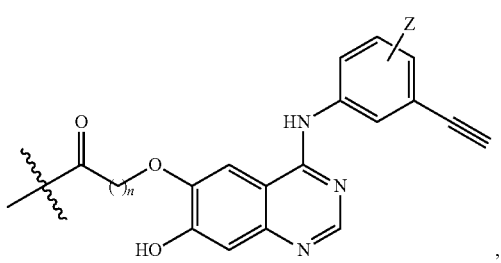
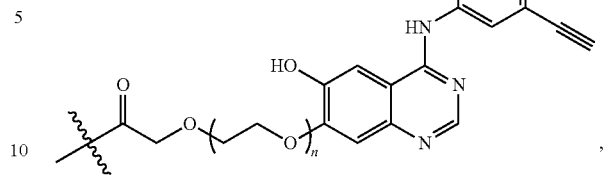
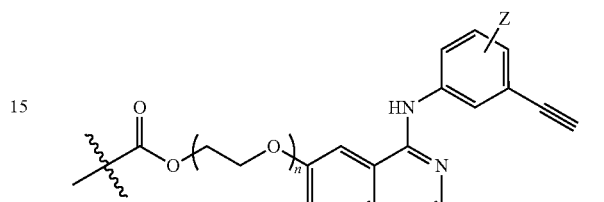
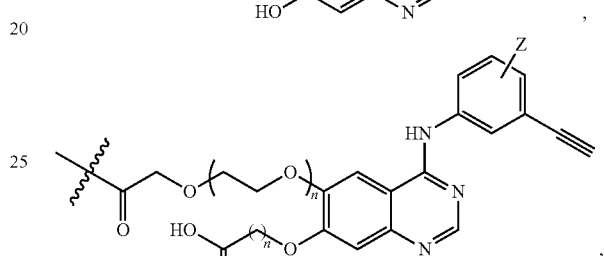
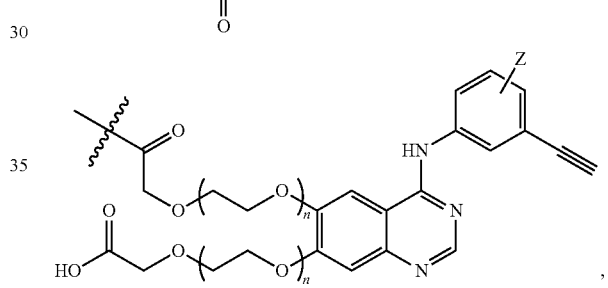
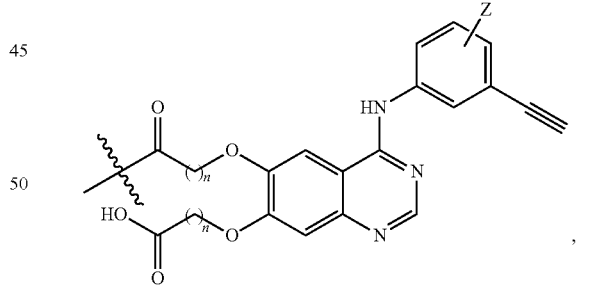
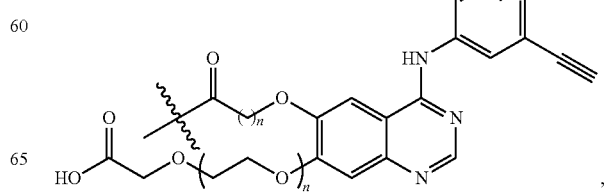

-continued
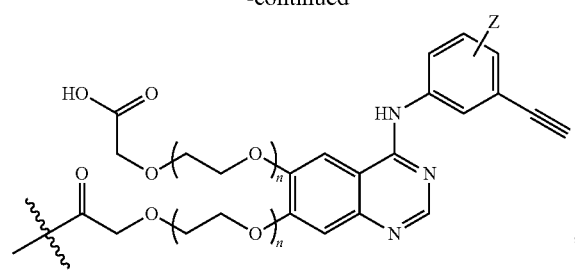
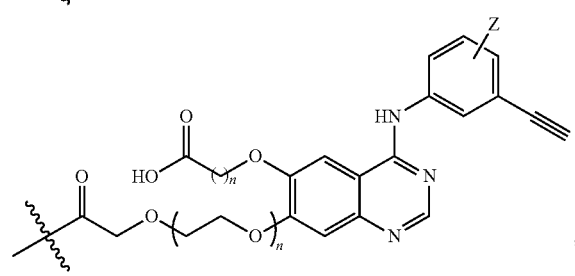
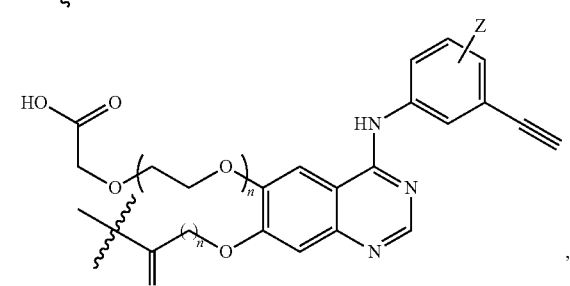
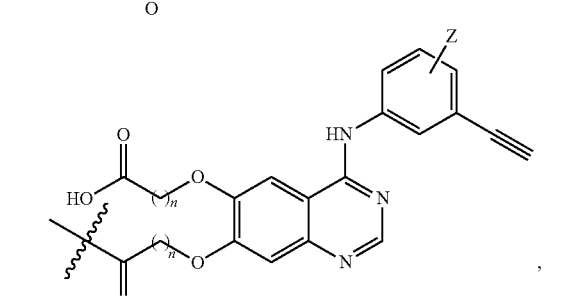
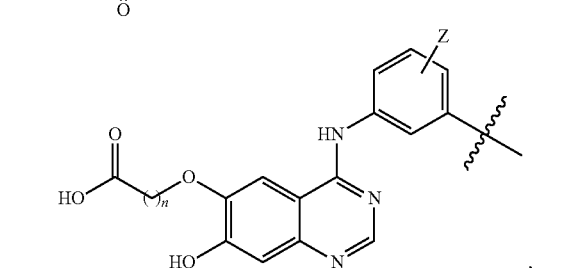
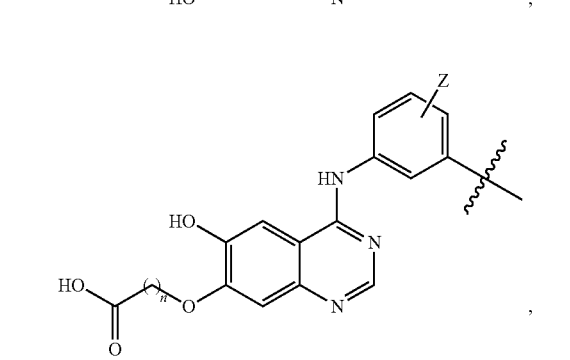
, and
where n is 1, 2, 3, 4, 5, or 6, including all ranges therebetween, and Z is hydrogen, an electron withdrawing group, a deactivating group, or a combination thereof, and where at each instance of the asterisk represents a chiral center (e.g., R or S chirality).
In an example, a compound of the present is disclosure compromises or further comprises a photosensitizer (e.g., a tetrapyrrolic core or reduced tetrapyrrolic core, including but not limited to, derivatives of HPPH), a linker moiety, an erlotinib analog group, and a functional group (e.g., a functional group that is PET active, such as a PET functional group). For example, a compound of the present disclosure is used for PET, fluorescence, and PDT.

In an example, the functional group (e.g., a functional group that is PET active) is an alkyl aryl moiety attached to a PET active group (e.g., —Sn(CH$_3$)$_3$, or -$^{124}$I), a group that is not PET active, or a combination thereof. The functional group (e.g., the functional group that is PET active) has a radioactive half-life of 24 hours (h) or more (e.g., 4 days).

In an example, the compound of the present disclosure has the following structure:

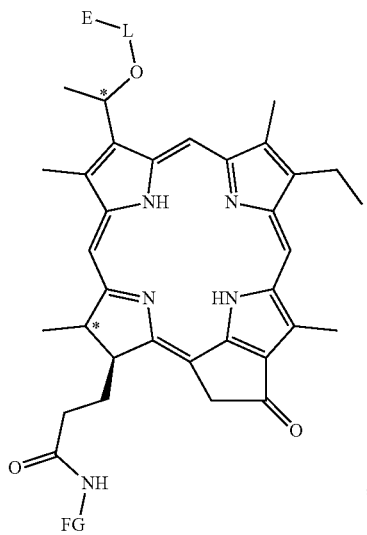

,

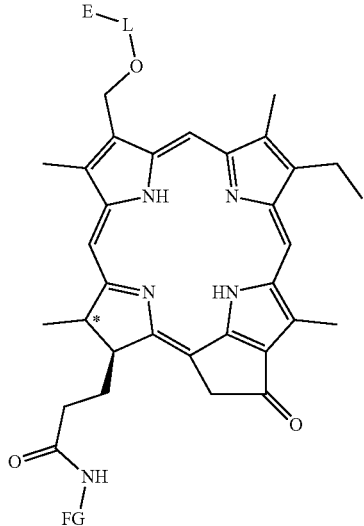

,

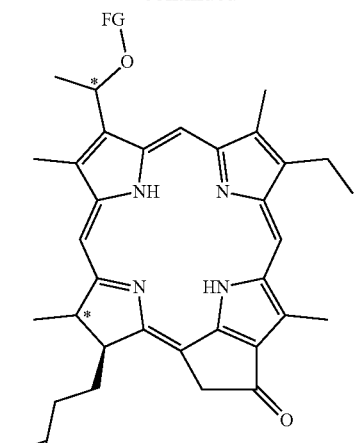

or

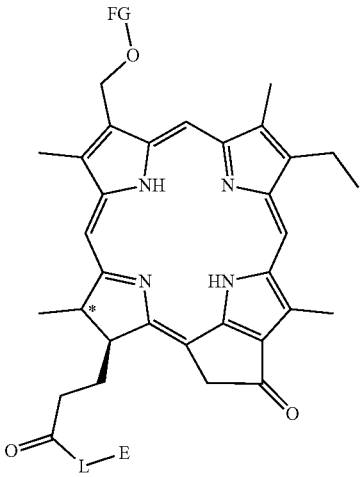

, where L is a linker moiety selected from the group consisting of:

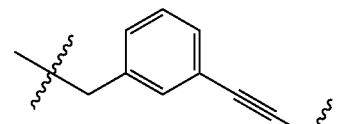

,

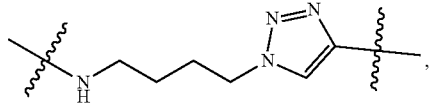

,

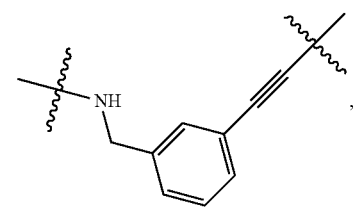

,

-continued
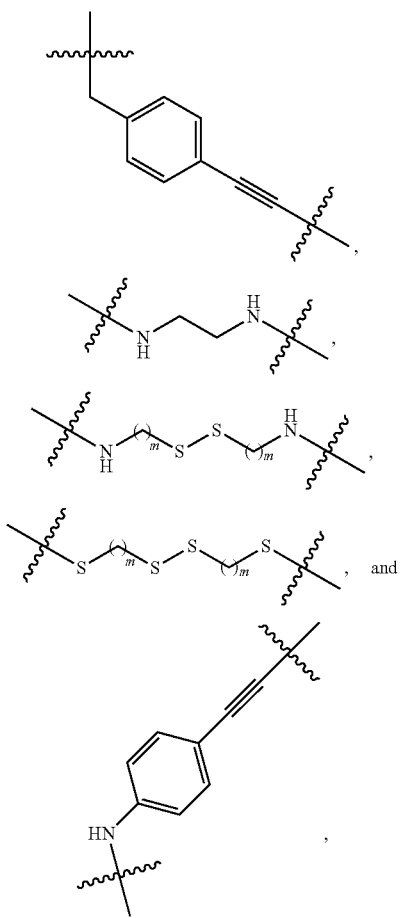
where m is m is 1, 2, 3, 4, 5, 6, 7, 8, 9, or 10, including all ranges therebetween,
E is selected from the group consisting of:
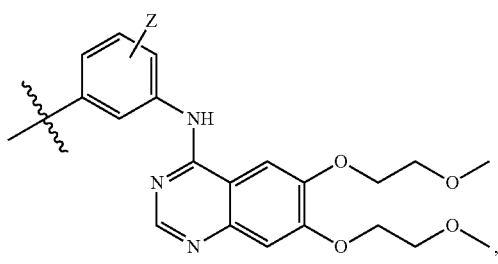
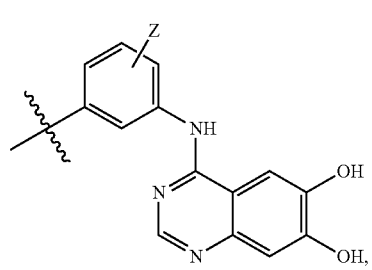
-continued
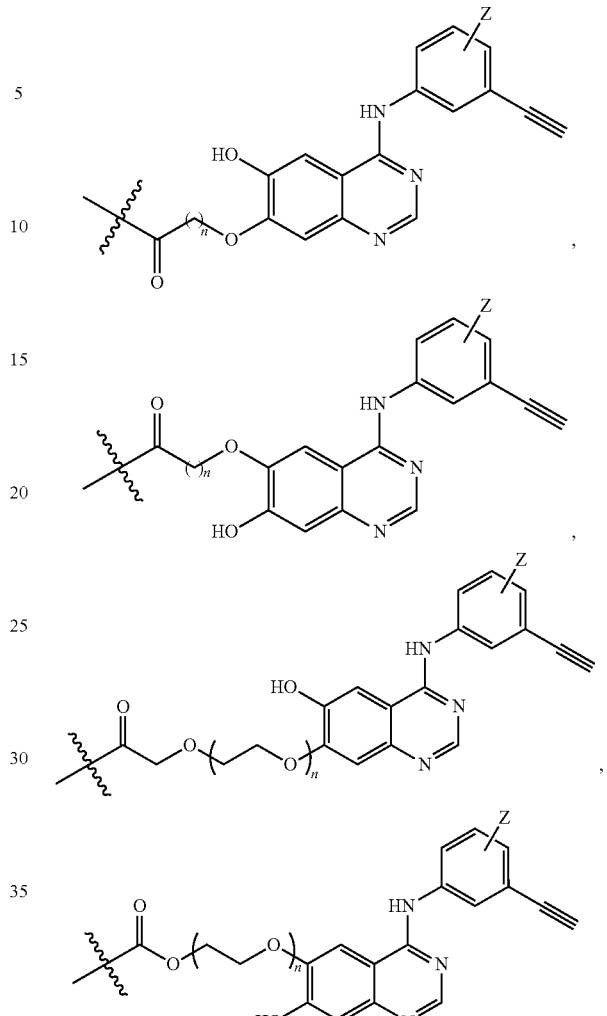
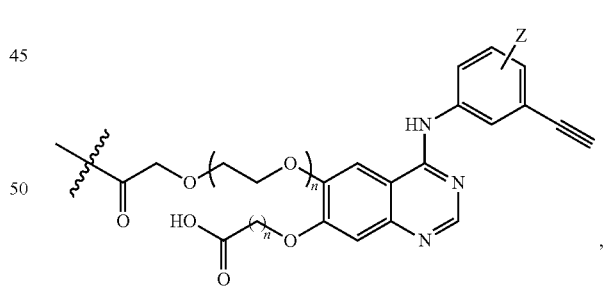
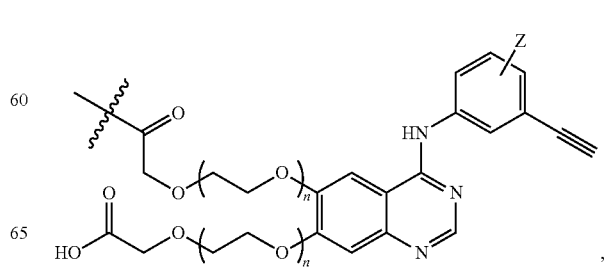

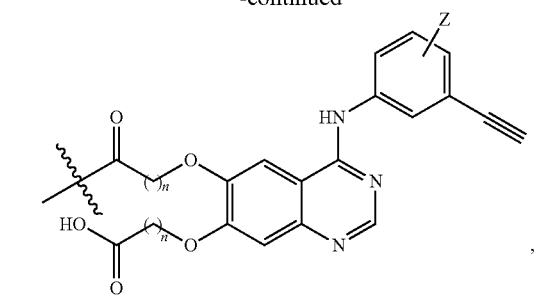,
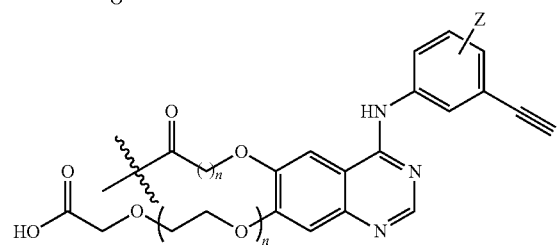,
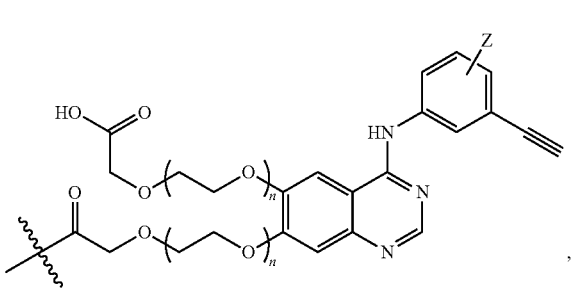,
,
,
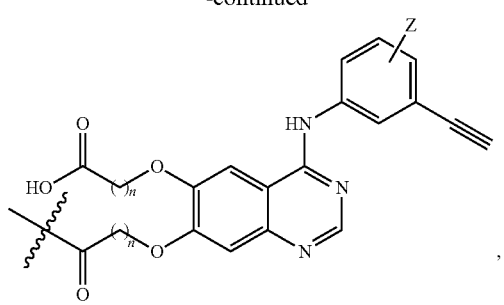,
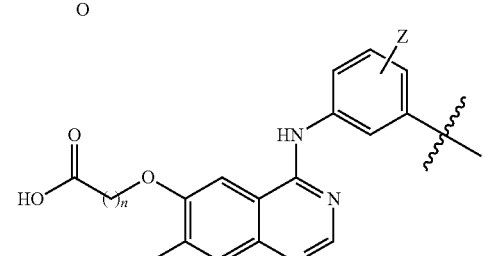,
,
,
,

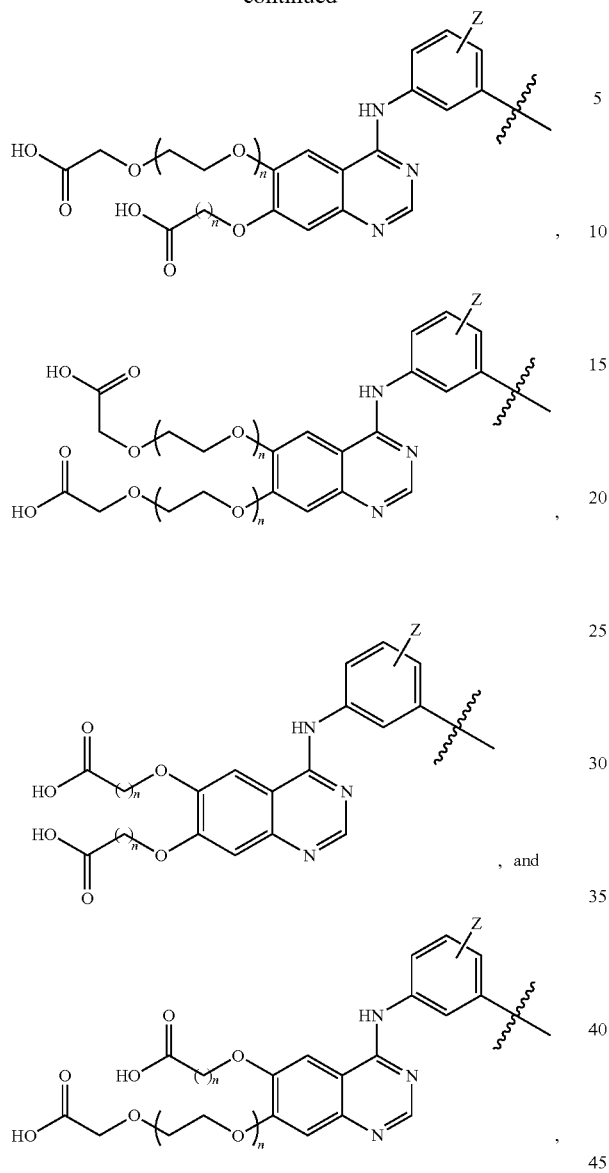

where where n is 1, 2, 3, 4, 5, or 6, including all ranges therebetween, and Z is hydrogen, an electron withdrawing group, a deactivating group, or a combination thereof, FG is a functional group (e.g., a functional group that is PET active) selected from the group consisting of:

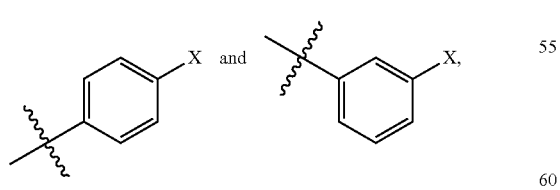

where X is —I, —Sn(CH$_3$)$_3$, -$^{124}$I, or combination thereof, and at each instance of the asterisk is a chiral center (e.g., R or S chirality).

In an example, compounds of the present disclosure have the following structures:

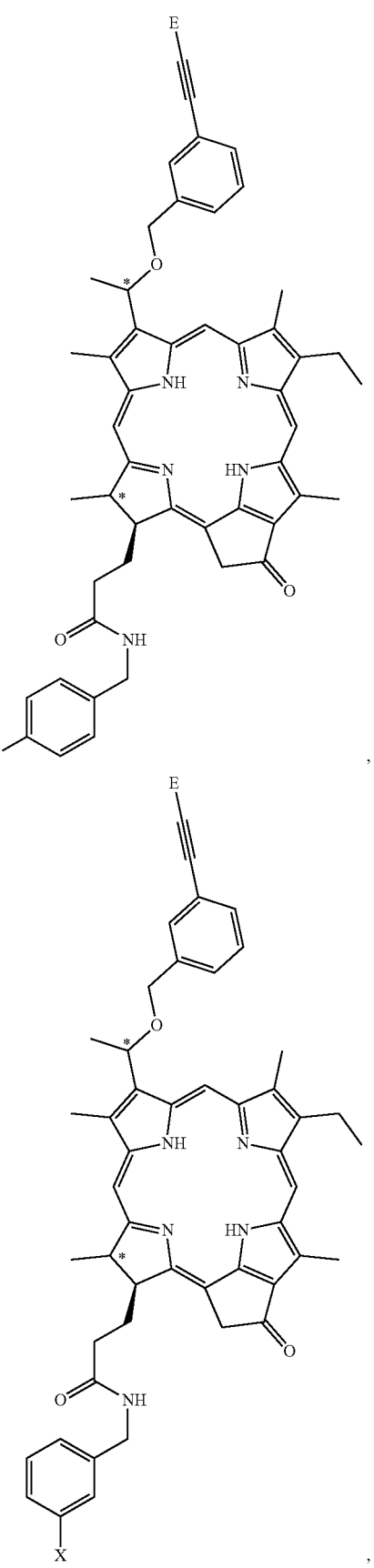

51
-continued
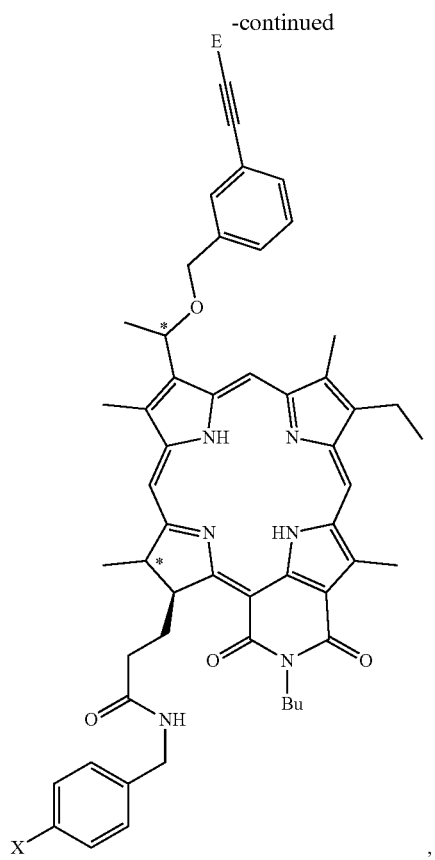
52
-continued
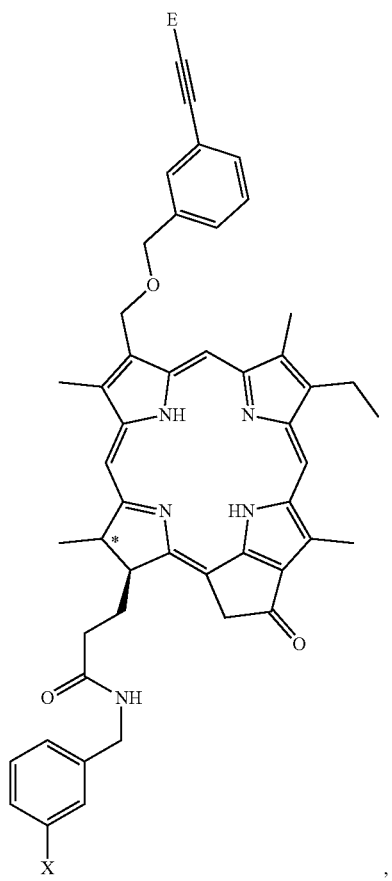
,
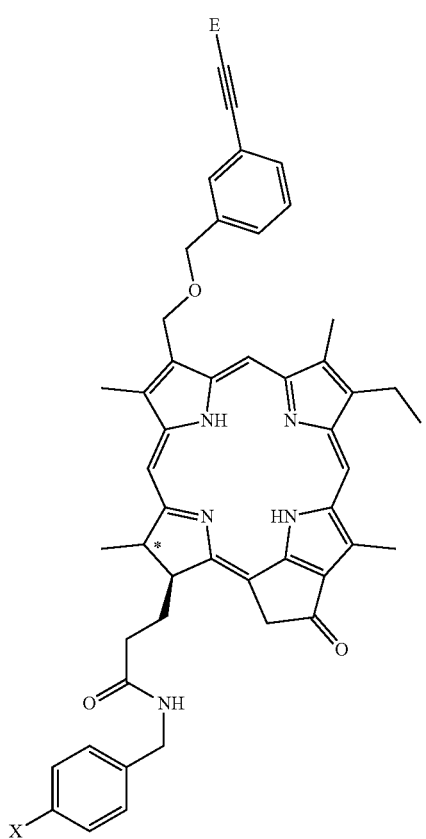
,
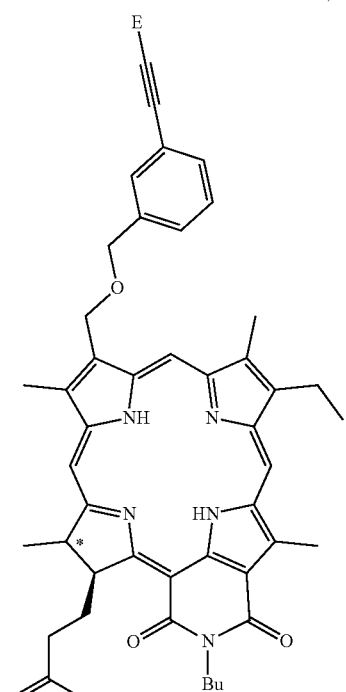
, 53
-continued
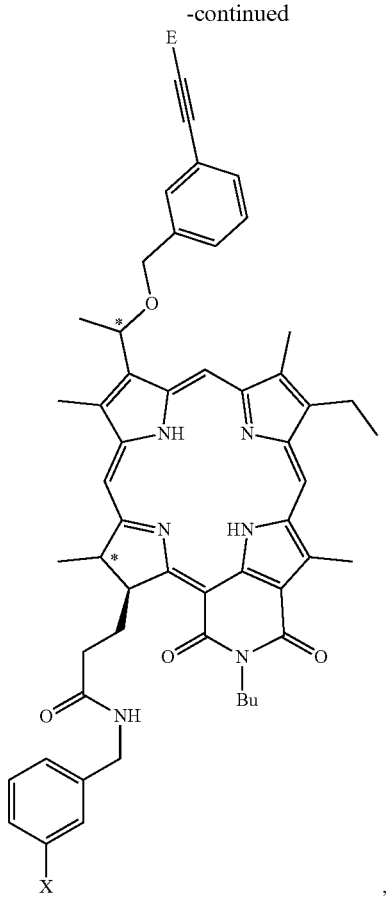
54
-continued
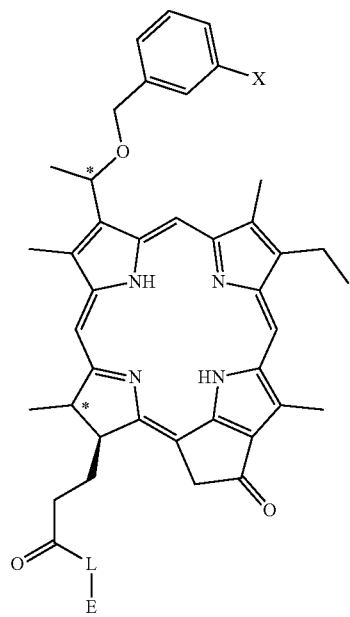
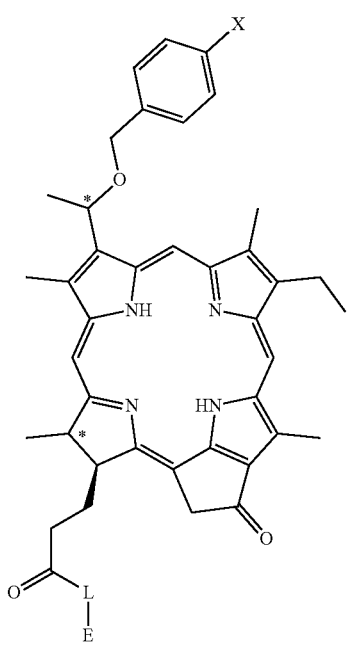
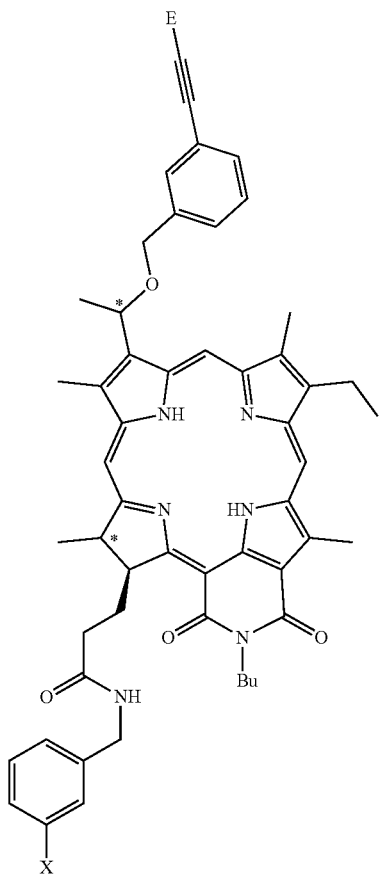

-continued
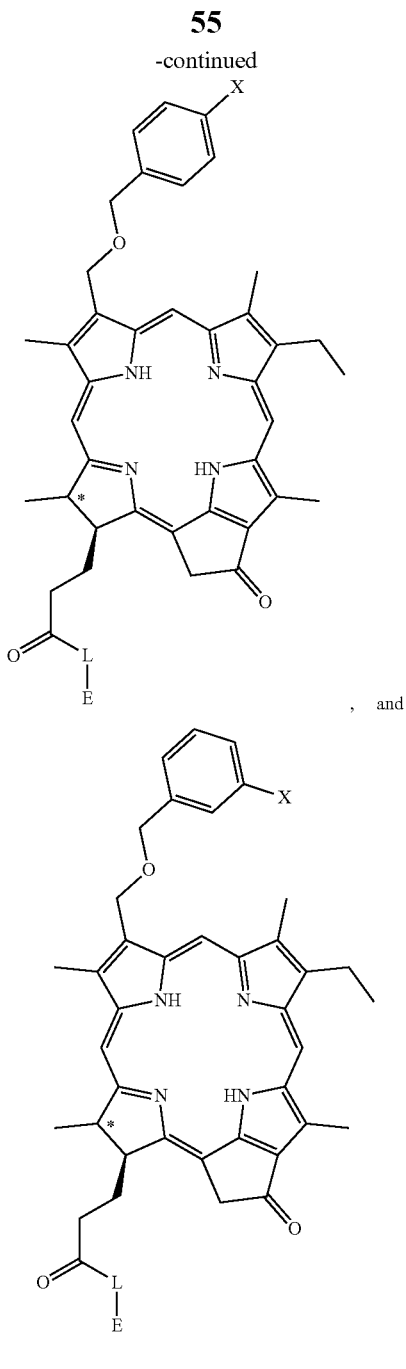
, and
where L is a linker moiety selected from the group
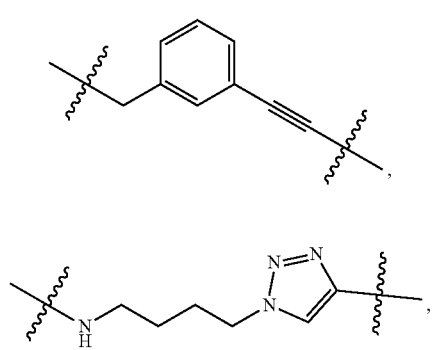
-continued
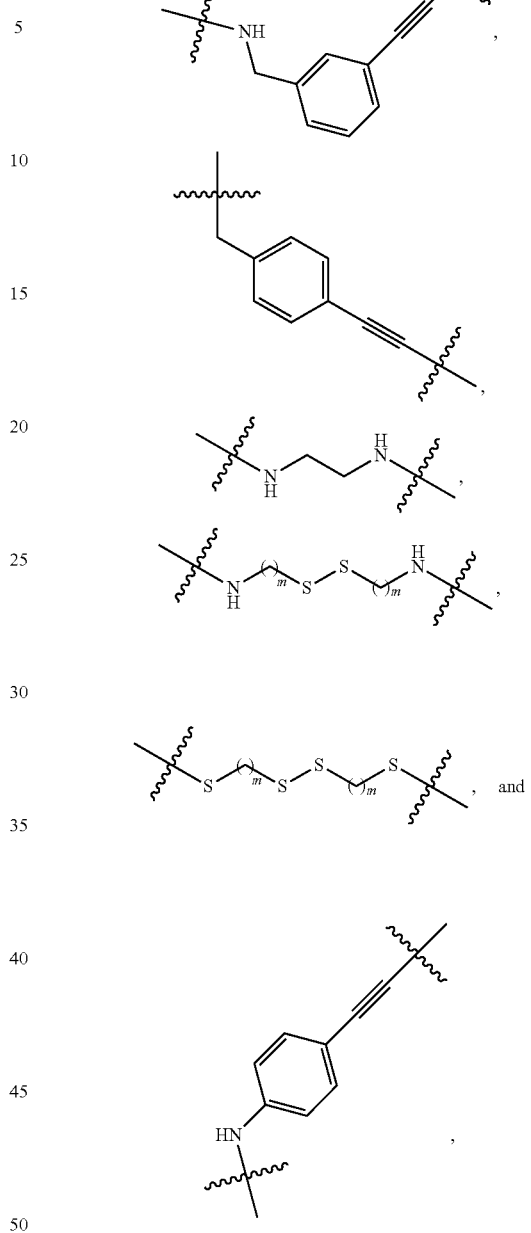
where m is 1, 2, 3, 4, 5, 6, 7, 8, 9, or 10, including all ranges therebetween,
X is —I, —Sn(CH$_3$)$_3$, -$^{124}$I, or combination thereof,
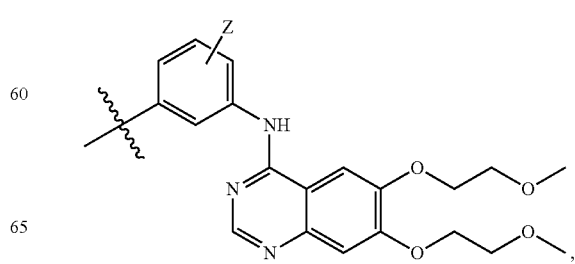

-continued
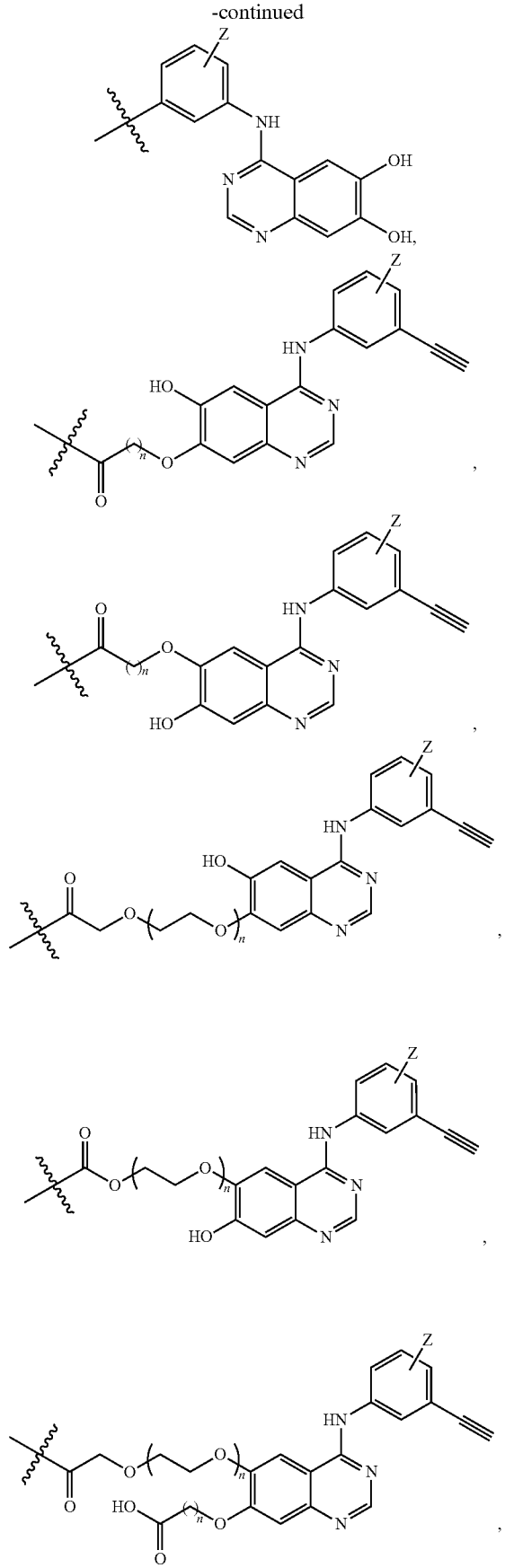
-continued
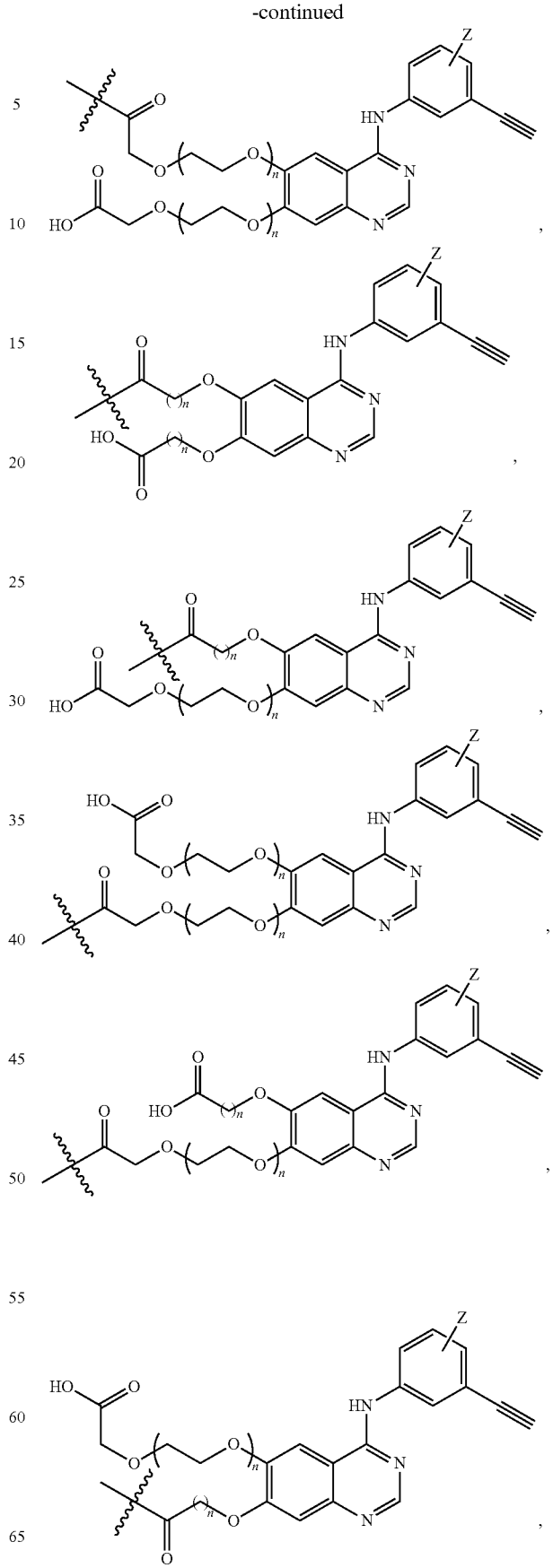

-continued
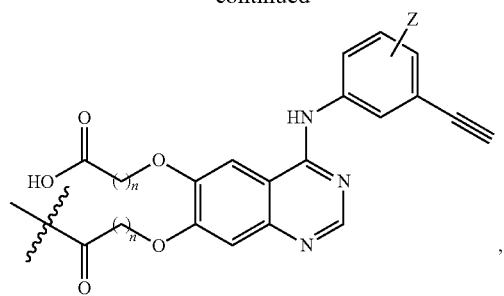
,
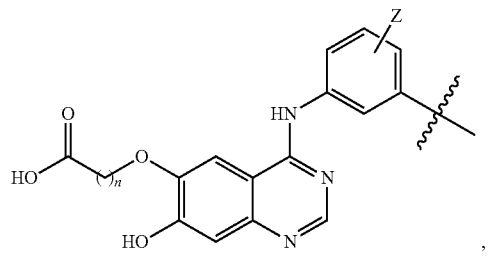
,
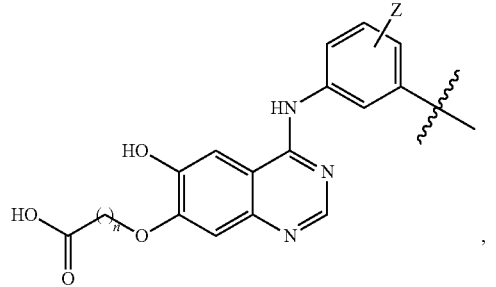
,
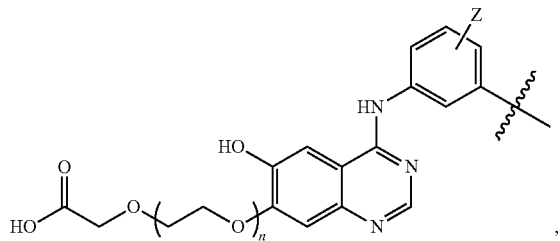
,
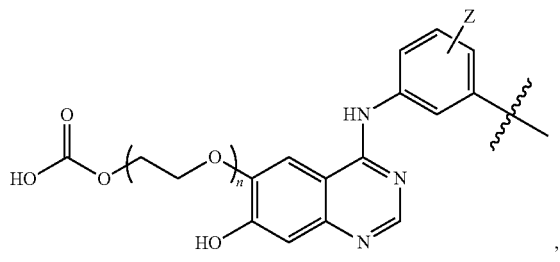
,
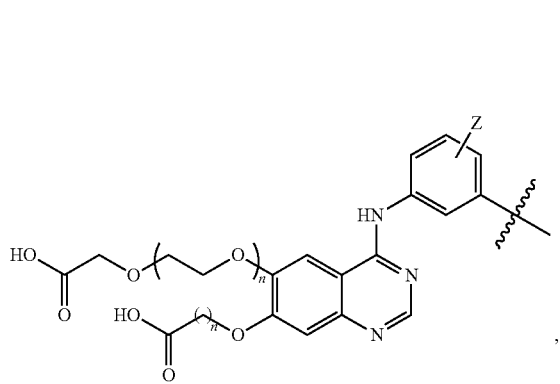
,
-continued
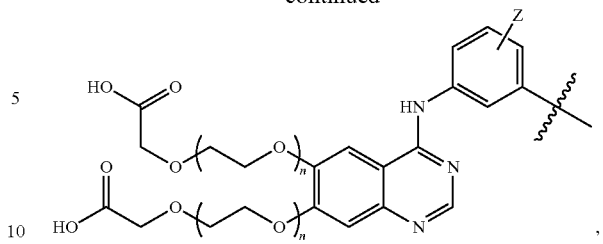
,
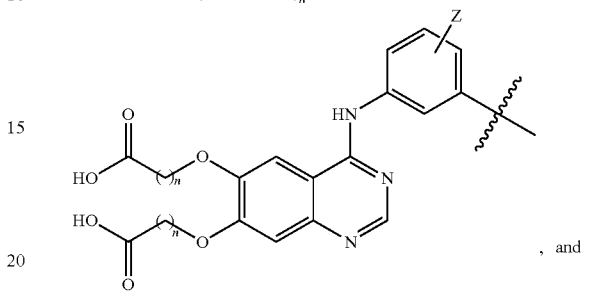
, and
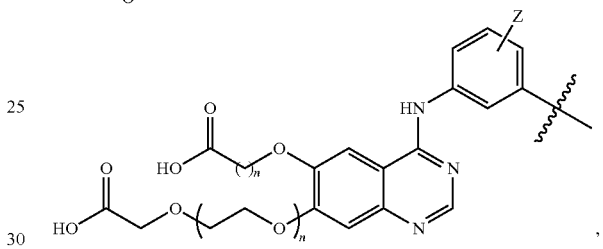
,
where n is 1, 2, 3, 4, 5, or 6, including all ranges therebetween, and Z is hydrogen, an electron withdrawing group, a deactivating group, or a combination thereof, and where at each instance of the asterisk represents a chiral center (e.g., R or S chirality). Alternatively, further non-limiting examples of the compound include:
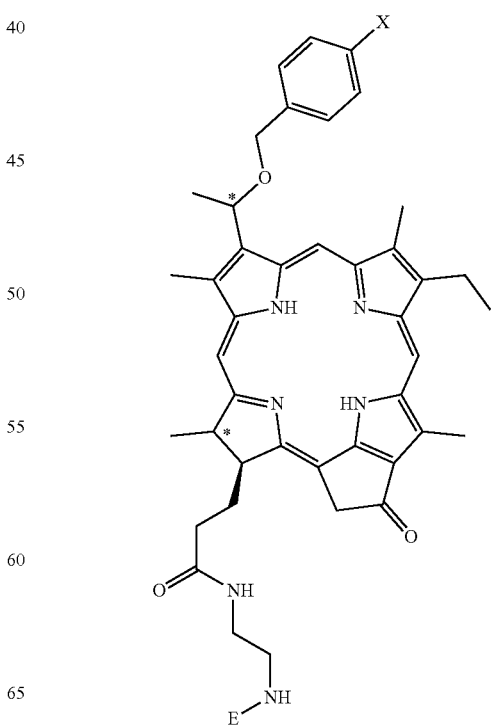
,

61
-continued
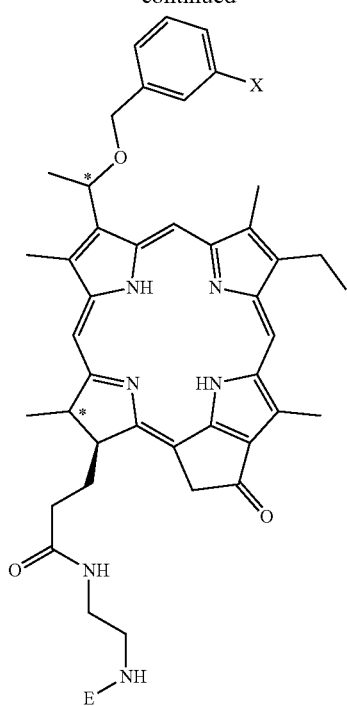
62
-continued
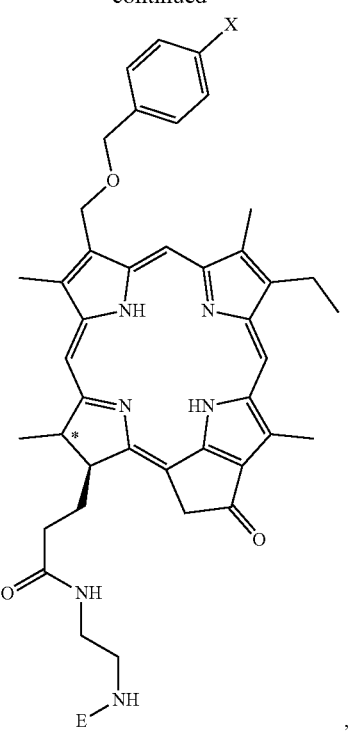
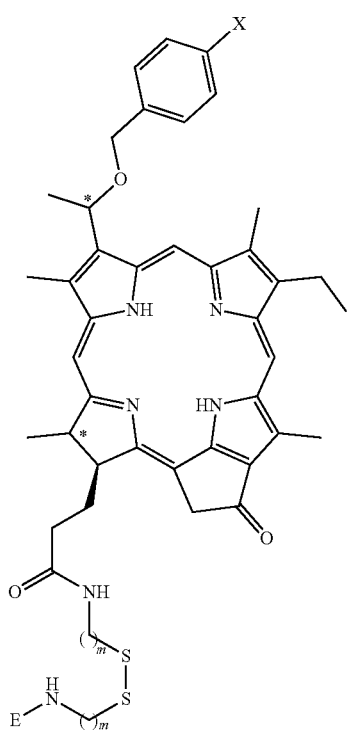
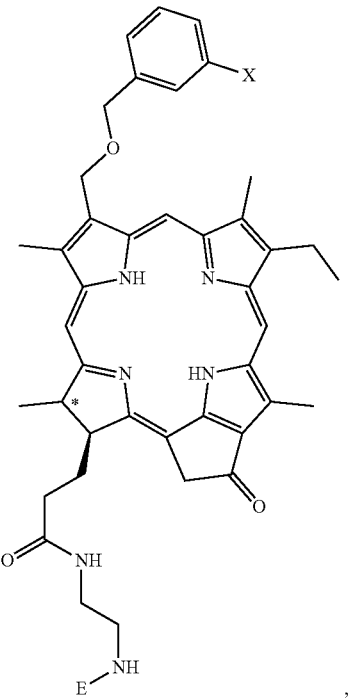

63
-continued
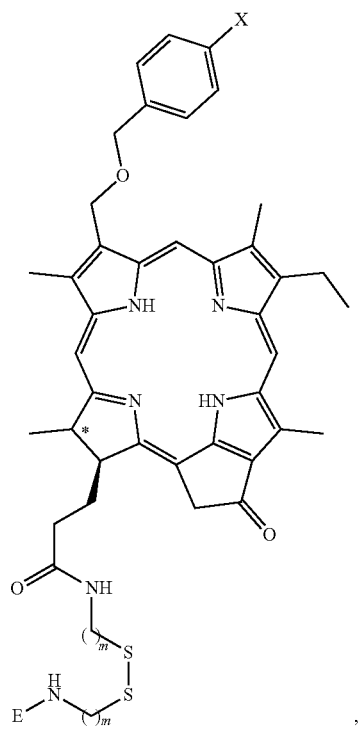
64
-continued
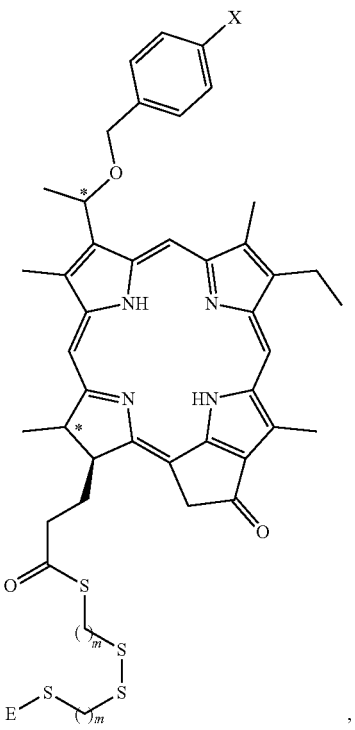
,
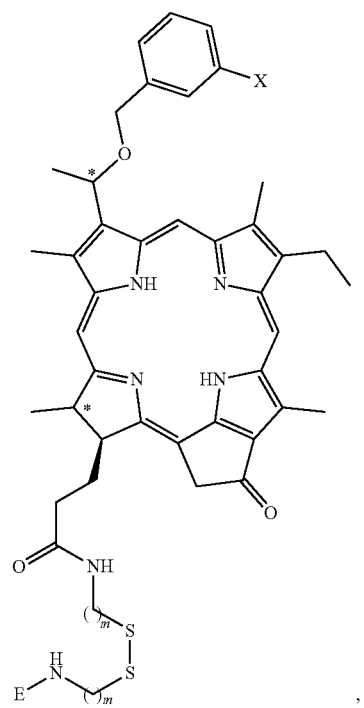
,
,

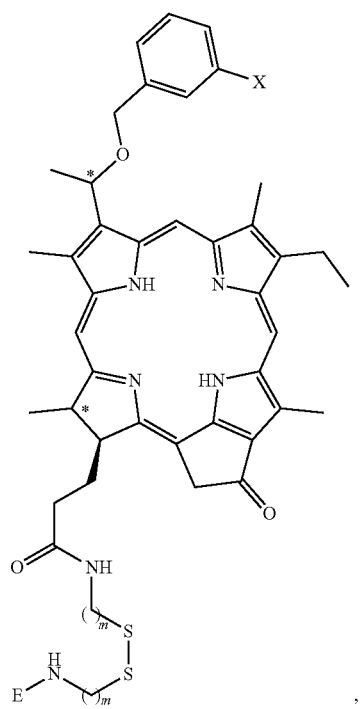
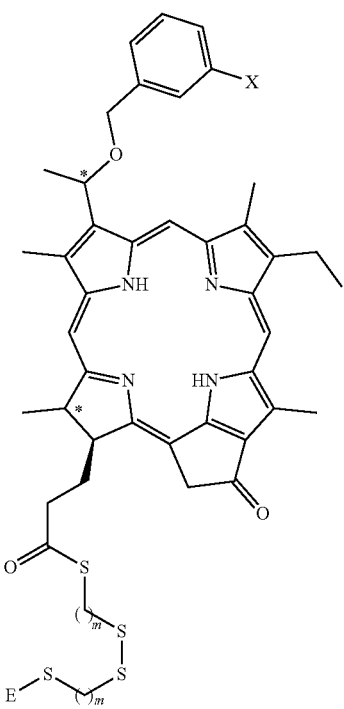
where m is 1, 2, 3, 4, 5, 6, 7, 8, 9, or 10, including all ranges therebetween, and X is —I, —Sn(CH$_3$)$_3$, -$^{124}$I, or combination thereof,
E is selected from the group consisting of:
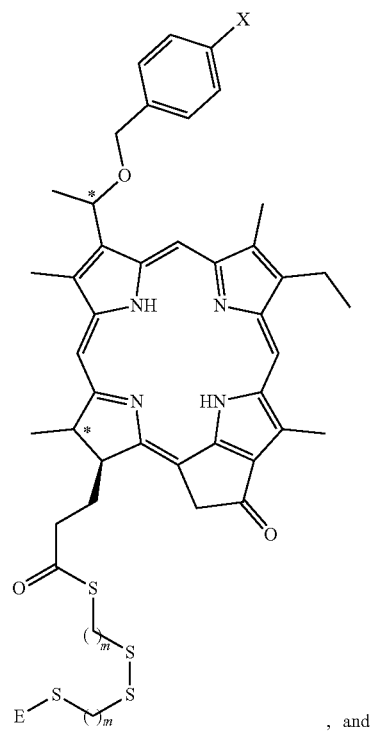, and
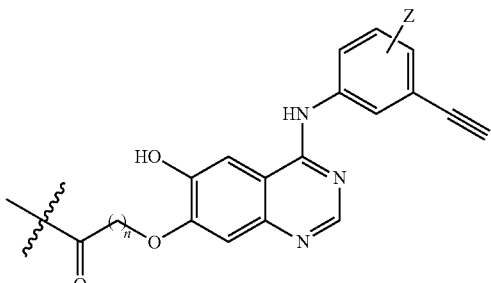
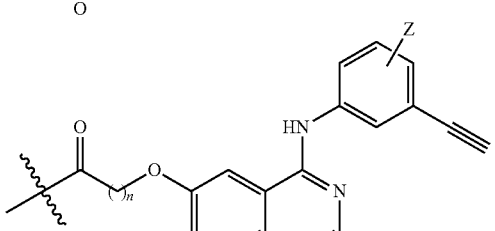
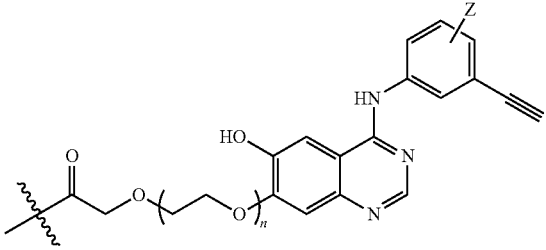

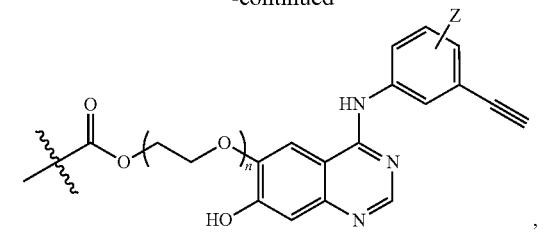

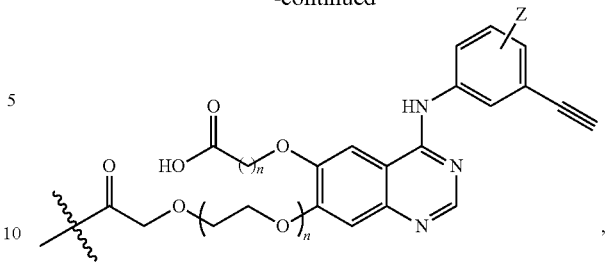

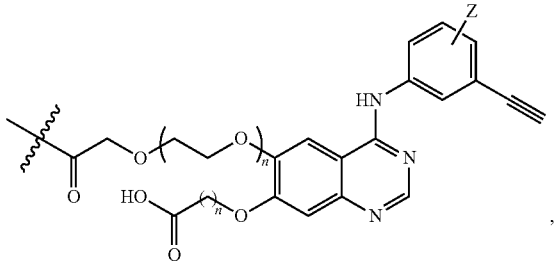

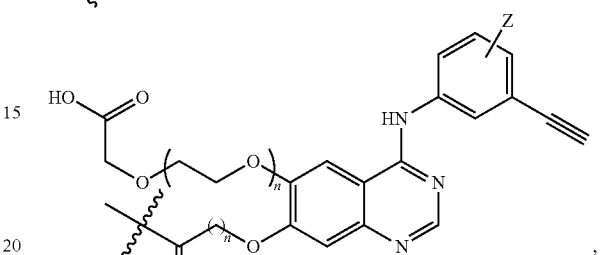

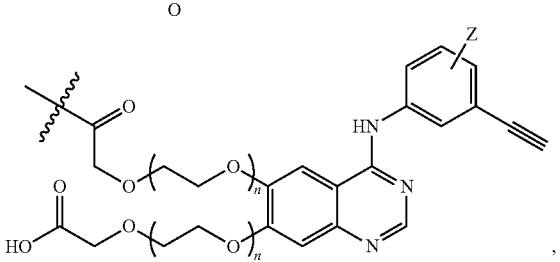

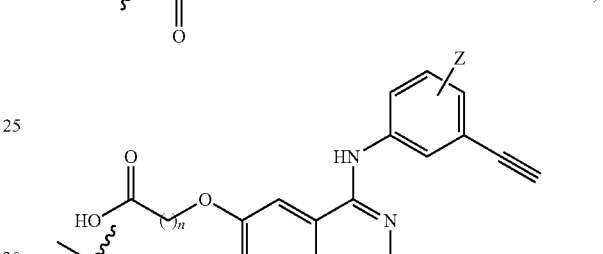

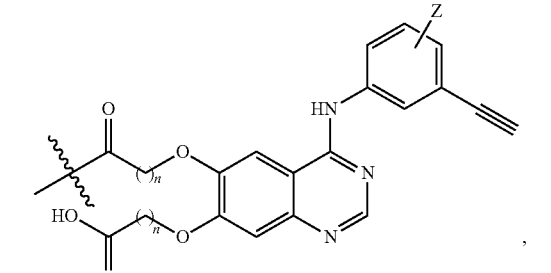

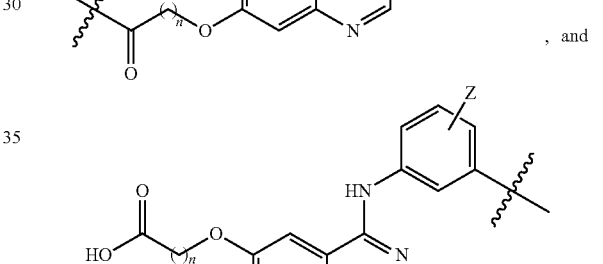

, and

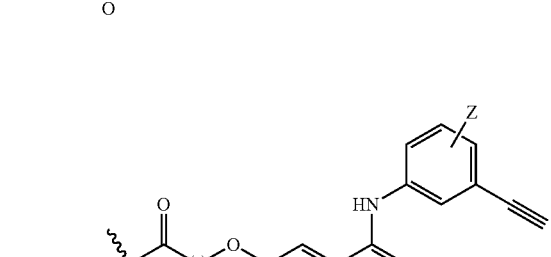

where n is 1, 2, 3, 4, 5, or 6, including all ranges therebetween, and Z is hydrogen, an electron withdrawing group, a deactivating group, or a combination thereof, and each instance of the asterisk represents a chiral center (e.g., R or S chirality).

In various examples, a compound is a salt, a partial salt, a hydrate, a polymorph, an isomer (e.g., a structural or stereoisomer), or a mixture thereof. The compounds can have stereoisomers. For example, the compound can be present as a racemic mixture, a single enantiomer, a single diastereomer, mixture of enantiomers, or mixture of diastereomers.

The compounds of the present disclosure include pharmaceutically acceptable derivatives and prodrugs of those compounds. A compound may be a lyophilized compound (e.g., a lyophilized powder).

In an aspect, the present disclosure provides compositions comprising one or more compound of the present disclosure. The compositions may comprise one or more pharmaceutically acceptable carrier.

The compositions can include one or more standard pharmaceutically acceptable carriers. The compositions can include solutions, suspensions, emulsions, and solid injectable compositions that are dissolved or suspended in a solvent before use. The injections can be prepared by dissolving, suspending or emulsifying one or more of the active ingredients in a diluent. Examples of diluents are distilled water for injection, physiological saline, vegetable oil, alcohol, and a combination thereof. Further, the injections can contain stabilizers, solubilizers, suspending agents, emulsifiers, soothing agents, buffers, preservatives, etc. The injections, are sterilized in the final formulation step or prepared by sterile procedure. The pharmaceutical composition of the invention can also be formulated into a sterile solid preparation, for example, by freeze-drying, and can be used after sterilized or dissolved in sterile injectable water or other sterile diluent(s) immediately before use. Non-limiting examples of pharmaceutically acceptable carriers can be found in: *Remington: The Science and Practice of Pharmacy* (2005) 21st Edition, Philadelphia, Pa. Lippincott Williams & Wilkins.

In an aspect, the present disclosure provides uses of compounds of the present disclosure. The compounds can be used as imaging agents (e.g., fluorescence imaging agents) or as both imaging and therapeutic agents.

In various examples, the present disclosure provides methods that use one or more compounds of the present disclosure. Examples of methods include, but are not limited to, methods of imaging an individual (or a portion thereof) and methods of imaging and treating an individual.

This disclosure provides methods of treating individuals in need of treatment (e.g., for a hyperproliferative disorder, such as, for example, malignancy (e.g., a malignancy disorder)) comprising administering to an individual a compound or composition of the present disclosure, and imaging the individual or a portion thereof and, after staging the disease, proceeding to appropriate therapy (surgical, chemotherapeutic, photodynamic, or standard radiation).

In an example, a method for detecting the presence of a hyperproliferative tissue in an individual comprises: administering to the individual one or more compound of the present disclosure or one or more composition of the present disclosure (e.g., an effective quantity of one or more compound of the present disclosure or one or more composition of the present disclosure); and imaging the individual or a portion thereof to detect the presence or absence of a hyperproliferative tissue in an individual. In an example, the method further comprises: irradiating the individual with light of a wavelength to kill or impair the hyperproliferative tissue.

In an example, a method of photodynamic therapy for treating hyperproliferative tissue in an individual, comprises: administering to the individual one or more compound of the present disclosure or one or more composition of the present disclosure (e.g., an effective quantity of one or more compound of the present disclosure or one or more composition of the present disclosure), and irradiating the individual with light of a wavelength to activate the compound, whereby the hyperproliferative tissue is treated (e.g., irradiating the individual with light of a wavelength to activate the compound and kill or impair the hyperproliferative tissue).

An image can be obtained using a techniques known in the art, such as, but not limited to, fluorescent imaging, and in some cases positron emission tomography (PET).

Methods of the present disclosure can be carried out in an individual who has been diagnosed with or is suspected of having cancer. A method can also be carried out in individuals who have a relapse or a high risk of relapse after being treated for cancer.

In various examples, a method for detecting the presence of a hyperproliferative tissue in an individual comprising: administering to the individual an effective quantity of one or more compound and/or one or more composition of the present disclosure; and imaging the individual or a portion thereof to detect the presence or absence of a hyperproliferative tissue in an individual.

A method may further comprise exposing the individual with light of a wavelength effective to treat the individual (e.g., kill or impair the hyperproliferative tissue).

The compound(s) and/or composition(s) may selectively interact(s) with hyperproliferative tissue relative to normal tissue, and a method may further comprise irradiating the individual with light of a wavelength to kill or impair the hyperproliferative tissue. A method may also further comprise allowing time for any of the compound(s) that is/are not selectively interacted with the hyperproliferative tissue to clear from the normal tissue of the subject prior to the step of exposure.

A method may use one or more lyophilized compound and/or one or more composition comprising one or more lyophilized compound. The lyophilized compound(s) and/or composition(s) may be reconstituted prior (e.g., immediately prior) to administration to the individual and immediately prior to imaging.

Methods of the present disclosure can be used on various individuals. Individuals are also referred to herein as subjects. In various examples, an individual is a human or non-human mammal. Examples of non-human mammals include, but are not limited to, farm animals, such as cows, hogs, sheep, and the like, as well as pet or sport animals such as horses, dogs, cats, and the like. Additional non-limiting examples of individuals include rabbits, rats, and mice.

"Hyperproliferative disorders" as used herein denotes those conditions disorders sharing as an underlying pathology excessive cell proliferation caused by unregulated or abnormal cell growth, and include uncontrolled angiogenesis. Examples of such hyperproliferative disorders includes, but are not limited to, cancers or carcinomas.

Non-limiting examples of cancers include head and neck, bladder, ovarian, thyroid, and lung cancers and the like.

Various hyperproliferative tissues can be imaged and/or treated using methods of the present disclosure. Non-limiting examples of hyperproliferative tissues include vascular endothelial tissue, a neovasculature tissue, a neovasculature tissue present in the eye, an abnormal vascular wall of a tumor, a solid tumor, a tumor of a head, a tumor of a neck, a tumor of an eye, a tumor of a gastrointestinal tract, a tumor of a liver, a tumor of a breast, a tumor of a prostate, a tumor of a lung, a tumor of an ovary, a tumor of the bladder, a tumor of the thyroid, a nonsolid tumor, malignant cells of one of a hematopoietic tissue and a lymphoid tissue. Combinations of hyperproliferative tissues can be imaged and/or treated.

In various examples, a method of the present disclosure comprises administering to an individual one or more compound and/or one or more composition of the present disclosure. The compound(s) and/or composition(s) and/or can be introduced into a subject using any suitable administration route, including but not limited to parenteral, subcutaneous, intraperitoneal, intramuscular, intravenous, mucosal, topical, intradermal, and oral administration. The compound(s) and/or composition(s) can be delivered to the vascular system of an individual such as, by using intravascular delivery. Administration can be done by way of a single dose or it can be done by multiple doses that are spaced apart.

The compounds can be used in lower amounts than previous PDT agents (e.g., structurally similar previous PDT agents). In various examples, a compound or compounds is/are administered to an individual at an amount (e.g., a dose) that is 25% or less, 50% or less, or 75% or less than a usual or typical amount (e.g. dose) of a previous PDT agent (e.g., a structurally similar previous PDT agent) that would be administered to the individual. In various other examples, the compounds are administered to an individual at amount (e.g., dose) that is 25% to 75% less or 50% to 75% less than a usual or typical amount (e.g. dose) of a previous PDT agent (e.g., a structurally similar previous PDT agent) that would be administered to the individual.

The compounds can act as conventional PDT agents. PDT methods are known in the art. The compounds of the present disclosure can be used in dual mode methods. In such methods, the compounds act as both a contrast agent/medium and as a therapeutic agent (e.g. as a photodynamic therapy (PDT) agent). Accordingly, dual mode methods comprise both an imaging step and an irradiation step: the "see and treat" algorithm.

"Irradiating" and "irradiation" as used herein includes exposing an individual to a desired wavelength or wavelengths of light. Preferably, the irradiating wavelength is selected to match the wavelength(s) which excite the photosensitizing compound. Preferably, the radiation wavelength matches the excitation wavelength of the photosensitizing compound and has low absorption by the non-target tissues of the individual, including blood proteins, because the non-target tissues have no absorbed the PDT compound. Irradiation is further defined herein by its coherence (laser) or non-coherence (non-laser), as well as intensity, duration, and timing with respect to dosing using the photosensitizing compound. The intensity or fluence rate must be sufficient for the light to reach the target tissue. The duration or total fluence dose must be sufficient to photoactivate enough photosensitizing compound to act on the target tissue. Timing with respect to dosing with the photosensitizing compound is important, because 1) the administered photosensitizing compound requires some time to home in on target tissue and 2) the blood level of many photosensitizing compounds decreases with time. The radiation energy is provided by an energy source, such as a laser or cold cathode light source, that is external to the individual, or that is implanted in the individual, or that is introduced into an individual, such as by a catheter, optical fiber or by ingesting the light source in capsule or pill form (e.g., as disclosed in. U.S. Pat. No. 6,273,904 (2001)).

In an example; a method is carried out using a single dose of the compound(s) and/or composition(s). In another example; a method is carried out using a single dose of the compound(s) and/or composition(s) and no radiation exposure.

In various examples, while the present methods use light energy for administering PDT to treat an individual (e.g., to kill or impair the hyperproliferative tissue) other forms of energy are within the scope of this disclosure, as will be understood by those of ordinary skill in the art.

As used herein, destroy means to kill the desired target tissue or target composition, including infecting agents. "Impair" means to change the target tissue or target composition in such a way as to interfere with its function or reduce its growth. For example, in North et al., it is observed that after virus-infected T cells treated with benzoporphyrin derivatives were exposed to light, holes developed in the T cell membrane and increased in size until the membrane completely decomposed (*Blood Cells* 18:129-40 (1992)). The target tissue or target composition is understood to be impaired or destroyed even if the target tissue or target composition is ultimately disposed of by macrophages.

In another aspect, the present disclosure provides kits. In an example, a kit comprises one or more compounds of the present disclosure and/or one or more compositions of the present disclosure and instructions for their use.

The kits can comprise pharmaceutical preparations containing any one or more of the compounds of the present disclosure. In an example, a kit is or includes a closed or sealed package that contains the pharmaceutical preparation. In certain examples, the package can comprise one or more closed or sealed vials, bottles, blister (bubble) packs, or any other suitable packaging for the sale, or distribution, or use of the pharmaceutical compounds and compositions comprising them. The printed material can include printed information. The printed information can be provided on a label, or on a paper insert, or printed on the packaging material itself. The printed information can include information that identifies the compound in the package, the amounts and types of other active and/or inactive ingredients, and instructions for taking the composition, such as the number of doses to take over a given period of time, and/or information directed to a pharmacist and/or another health care provider, such as a physician, or a patient. The printed material can include an indication that the pharmaceutical composition and/or any other agent provided with it is for treatment of cancer and/or any disorder associated with cancer. In examples, the kit includes a label describing the contents of the container and providing indications and/or instructions regarding use of the contents of the kit to treat any cancer.

The steps of the methods described in the various embodiments and examples disclosed herein are sufficient to carry out the methods of the present disclosure. Thus, in an example, a method consists essentially of a combination of the steps of the methods disclosed herein. In another example, a method consists of such steps.

The following example is presented to illustrate the present disclosure. It is not intended to limiting in any matter.

EXAMPLE 1

This example provides a description of synthesizing and characterizing and using compounds of the present disclosure.

Impact of the position of substituent(s) at the periphery of porphyrin-based compounds. The impact of the position of the erlotinib or modified erlotinib at various positions of a variety of asymmetrical porphyrin-based photosensitizers was investigated. To achieve this goal, the synthetic strategy was divided in six parts.

Part 1: Presence of erlotinib at the lower half of the molecule—In this part of the invention following conjugates were synthesized. The rationale for the synthesis of PS-erlotinib conjugates 1-5 was as follow:

(a) To investigate the importance of the nature of linker(s) joining the two moieties (1, 2 & 3), and determine the conjugation of erlotinib in photosensitizers containing either a 5-member isocyclic ring or a six member imide ring system (2 vs. 4).

(b) Compare the importance of erlotinib substituent in longer wavelength absorbing PS, e.g., purpurinimide (700 nm) and bacteriopurpurinimide (782 nm), 4 & 5, in which one pyrrole ring or two pyrrole rings (diagonal to each other are reduced.

(c) To investigate the importance of the nature of linker(s) joining the two moieties (1-3).

Figure 15:
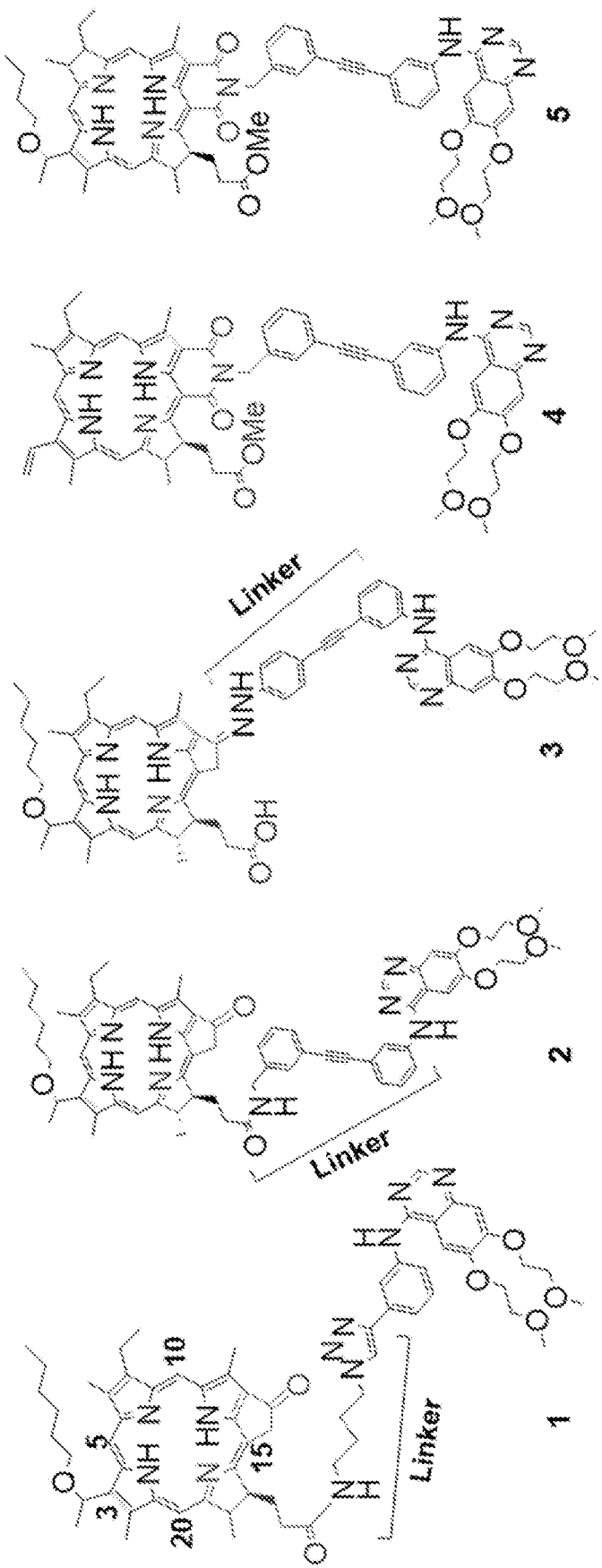
FIG. 15 shows the conjugation of erlotinib in photosensitizers containing either of a 5-member isocyclic ring or a 6-member imide ring system.

(d) To determine the conjugation of erlotinib in photosensitizers containing either a 5-member isocyclic ring or a six member imide ring system (2 vs. 4). See FIG. 15.

Part 2: Presence of erlotinib at the upper half of the molecule—The rationale for the synthesis of PS-erlotinib conjugates 6-11 was as follows:

(a) Compare the presence of erlotinib in pyropheophorbides 6 & 7 with related bacteriochlorin analogs 8 & 9, bearing a 5-member fused isocyclic ring and two pyrrole rings diagonal to each other are reduced.

(b) Compare the effect of bacteriochlorins bearing a 5 member isocyclic ring 8 & 9, with bacterichlorins 10 & 11, containing a fused six member N-butyl imide ring system.

Figure 16:
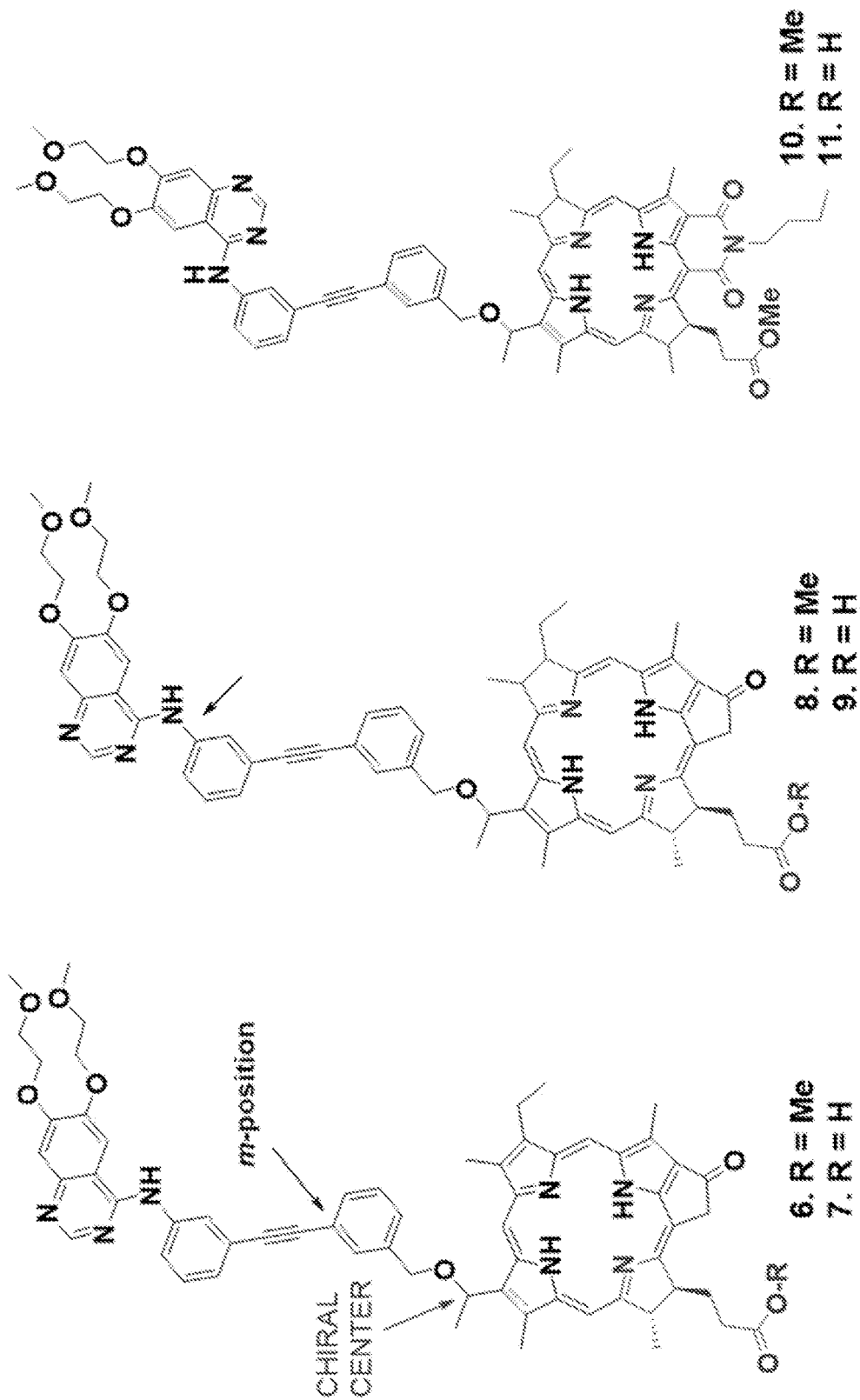
FIG. 16 shows the presence of erlotinib in pyropheophorbides 6 & 7, bacteriochlorin analogs 8 & 9, and bacterichlorins 10 & 11.

(c) Investigate the cells specificity of the methyl ester vs. carboxylic acid functionality in PS 26-31. (d) Compare the effect of bacteriochlorins bearing a 5 member isocyclic ring 8 & 9, with bacterichlorins 10 & 11, containing a fused six member N-butyl imide ring system. See FIG. 16.

Figure 17:
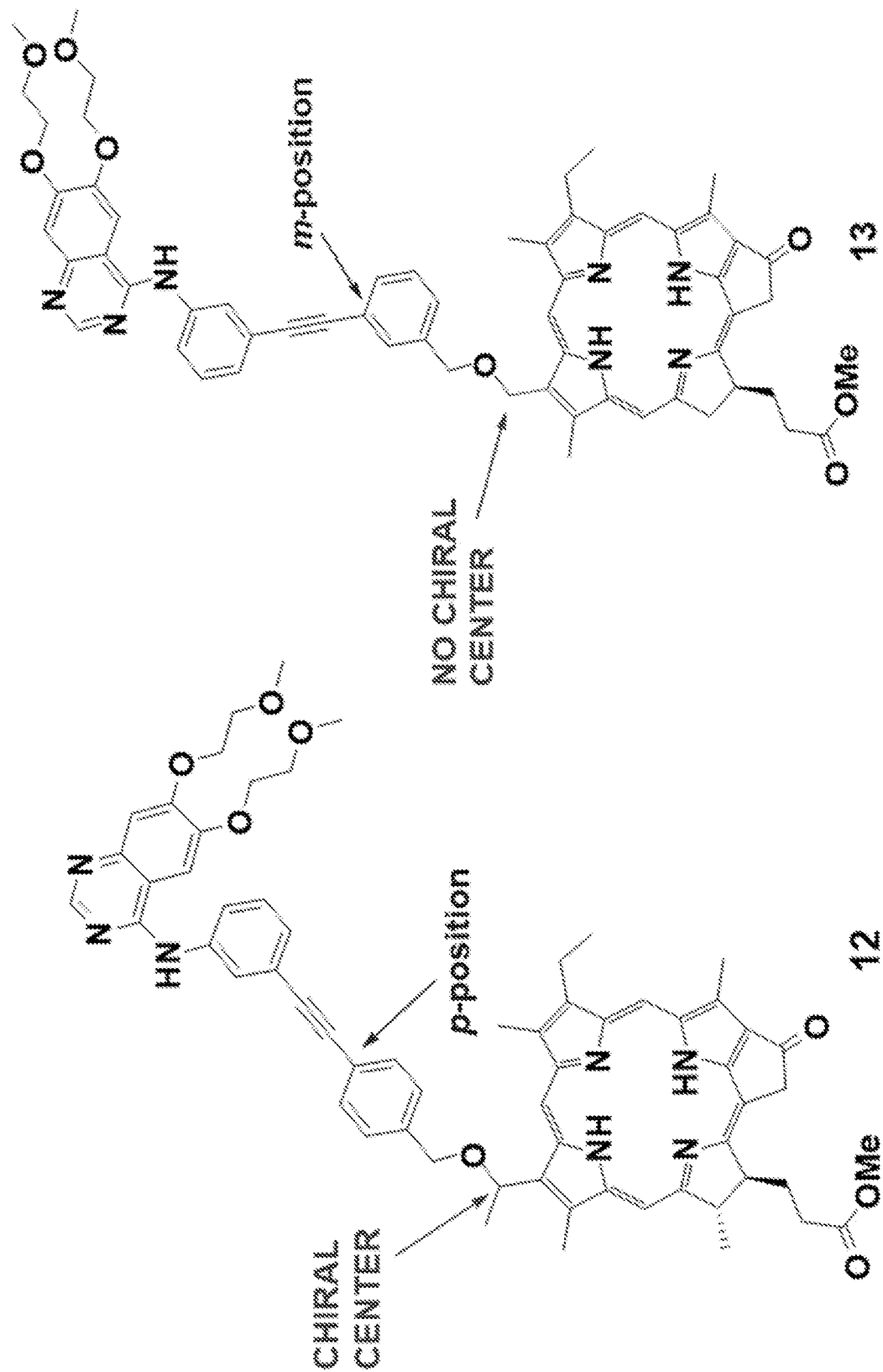
FIG. 17 shows the presence of erlotinib either at position-3 (conjugate 6) or at position-4 of the benzyloxyethyl functionality.

Part 3: Determine the impact of the position of erlotinib at the upper half of the molecule: The rationale for the synthesis of conjugate 12 was to investigate the importance of the presence of erlotinib either at position-3 (conjugate 6) or at position-4 of the benzyloxyethyl functionality. See FIG. 17.

Part 4: Determine the importance of chirality at position-$3^1$ of PS-erlotinib conjugate at the upper half of the molecule—Previous reports with a series of alkyl ether and benzyl ether photosensitizers have shown that chirality at position $3^1$-position is necessary for efficient in vivo biological efficacy. Therefore, to investigate the structural requirement for erlotininb substituted PS, compound 13 was designed and successfully synthesized and its efficacy was compared with conjugate 6 bearing a chiral center at position-$3^1$.

Figure 18:
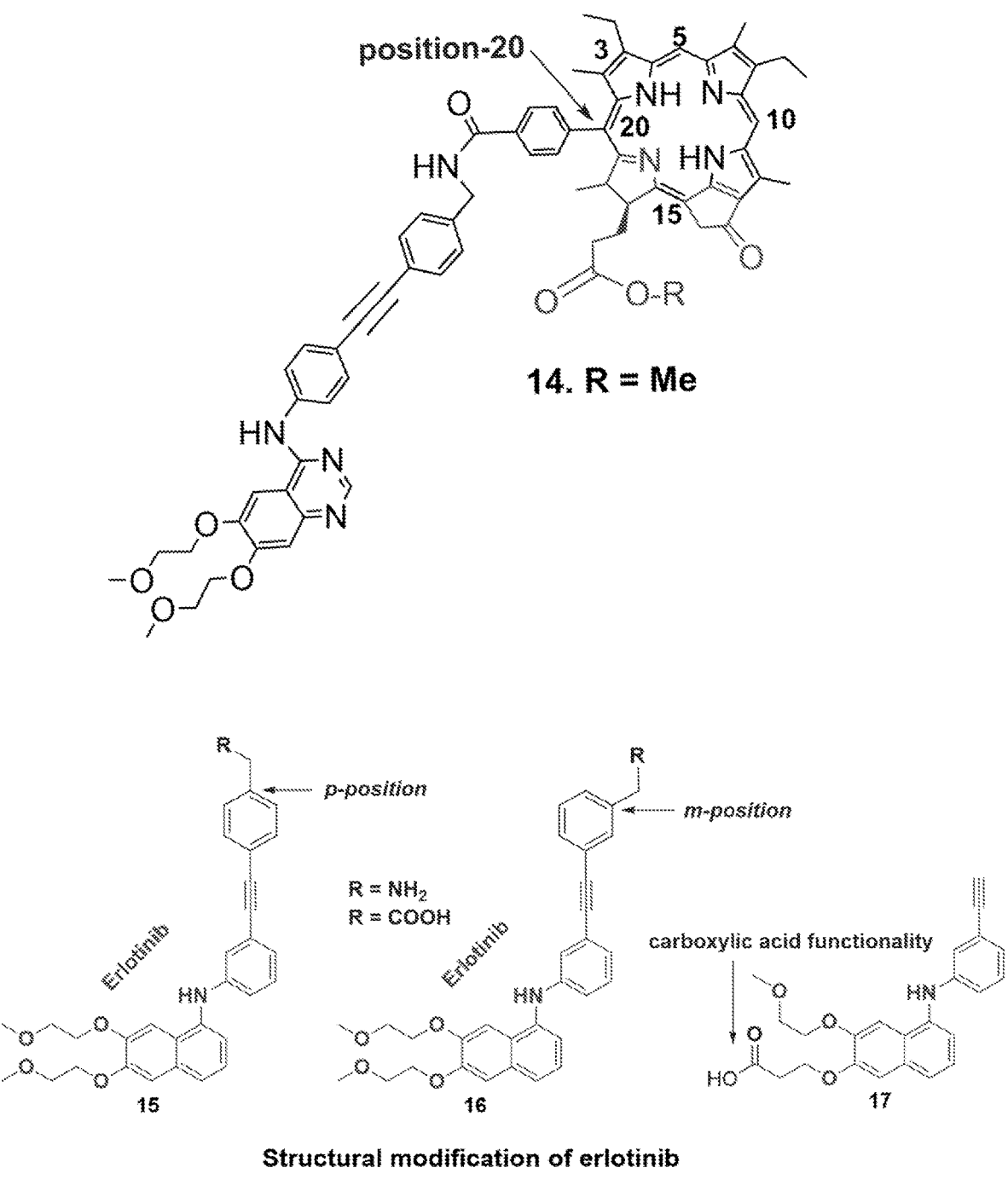
FIG. 18 shows compounds 14-17, showing the structural modification of erlotinib.

Part 5: Investigate the impact of erlotinib substituted at position-20 of the photosensitizer. The main objective of this approach was to determine the target-specificity of erlotinib introduced at position-20 of the PS. For initial study, pyropheophorbide-a analog containing an ethyl group at position-3 was used as the starting material. The PK/PD profiles can be altered by introducing desired alkyl ether side chain at position-3 and replace the methyl ester group with carboxylic acid functionality. See FIG. 18.

Figure 19:
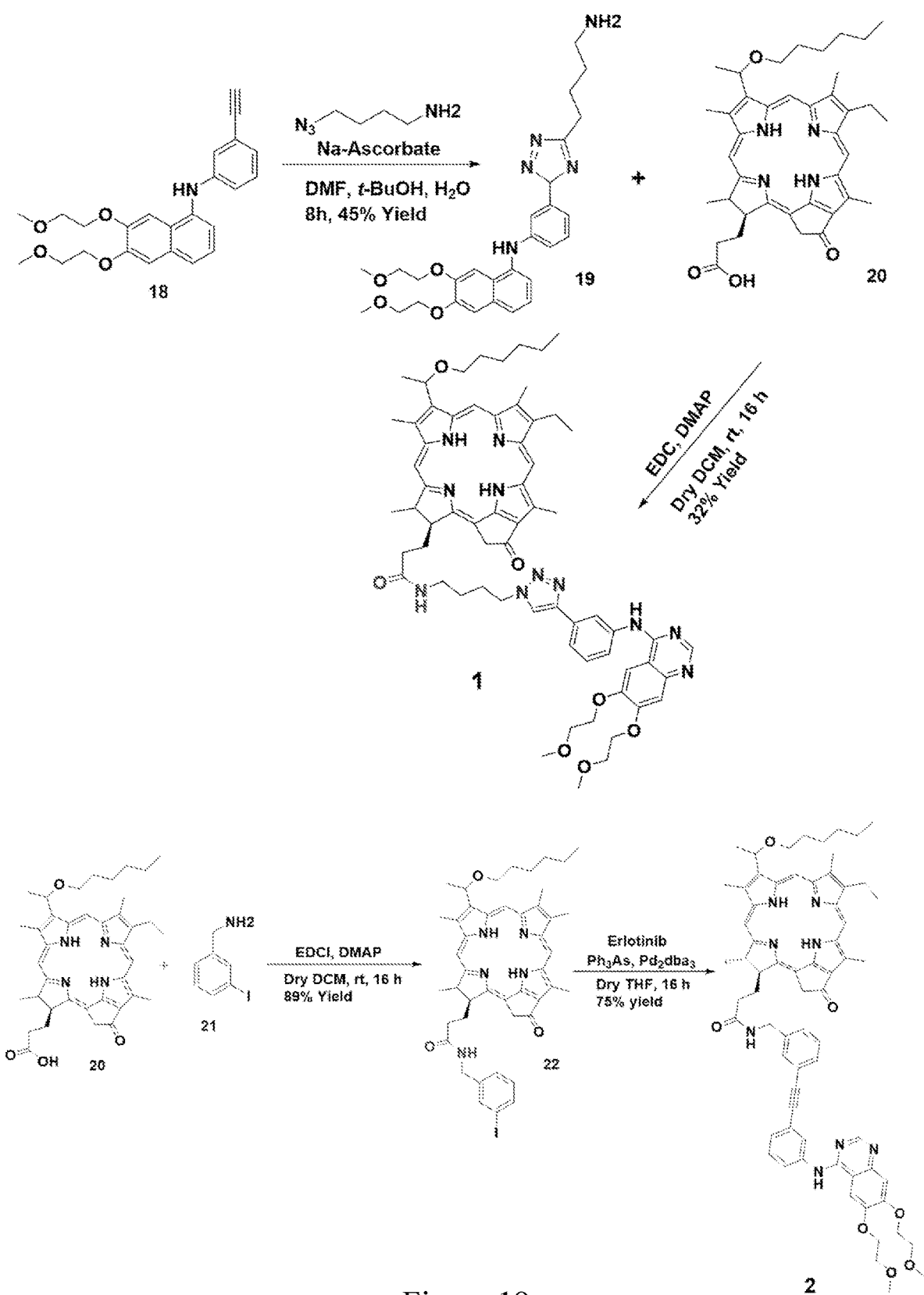
FIG. 19 shows the synthesis of modified erlotinib analogs.
Figure 20:
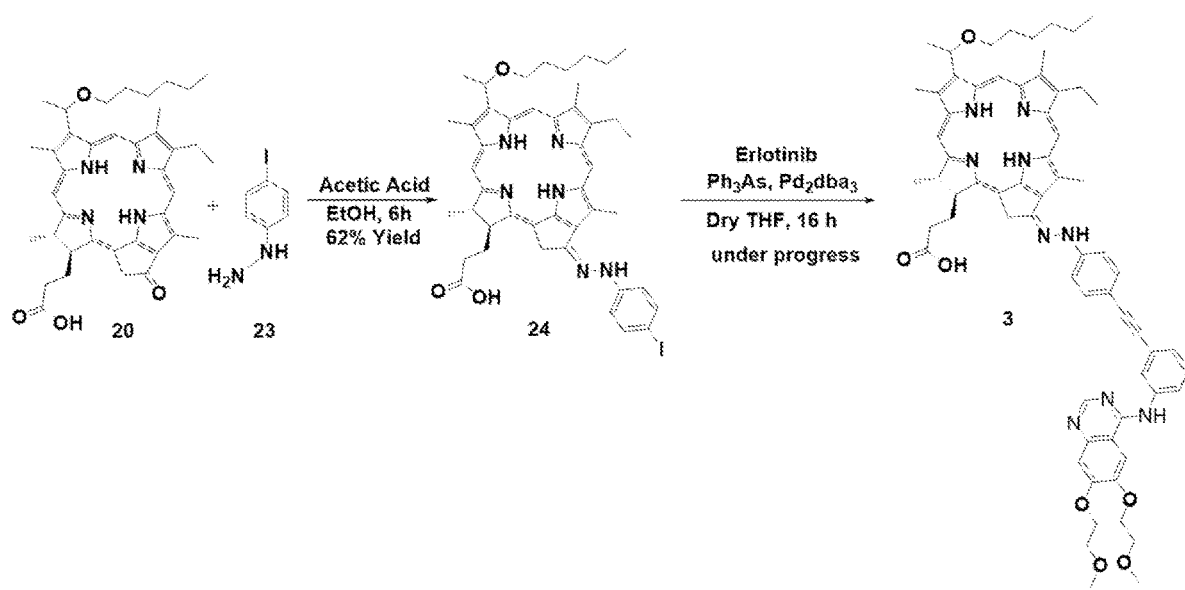
FIG. 20 shows the synthesis of modified erlotinib analogs.
Figure 20:
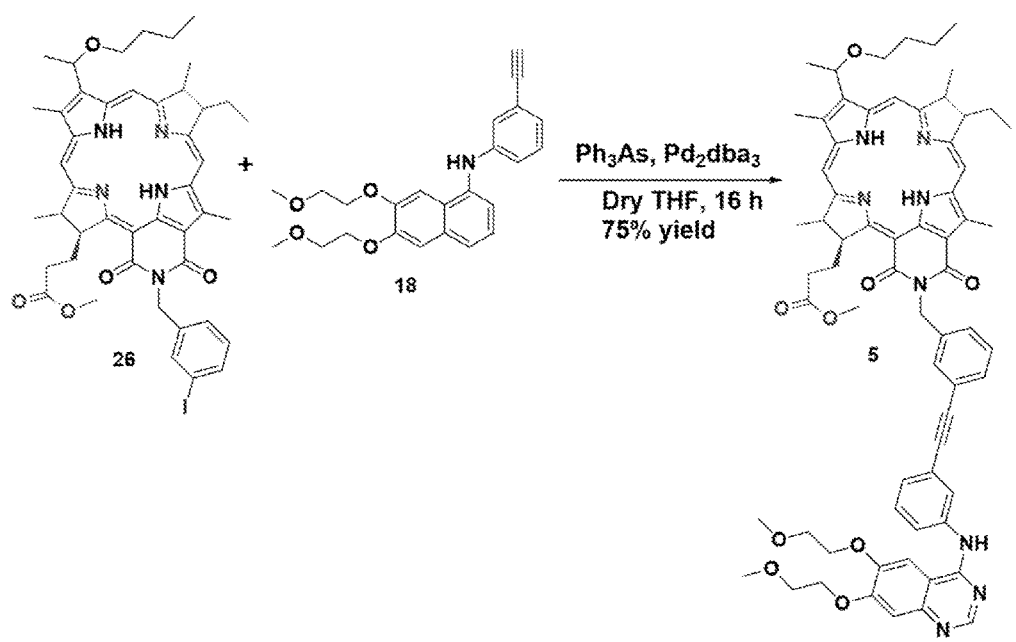
Figure 21:
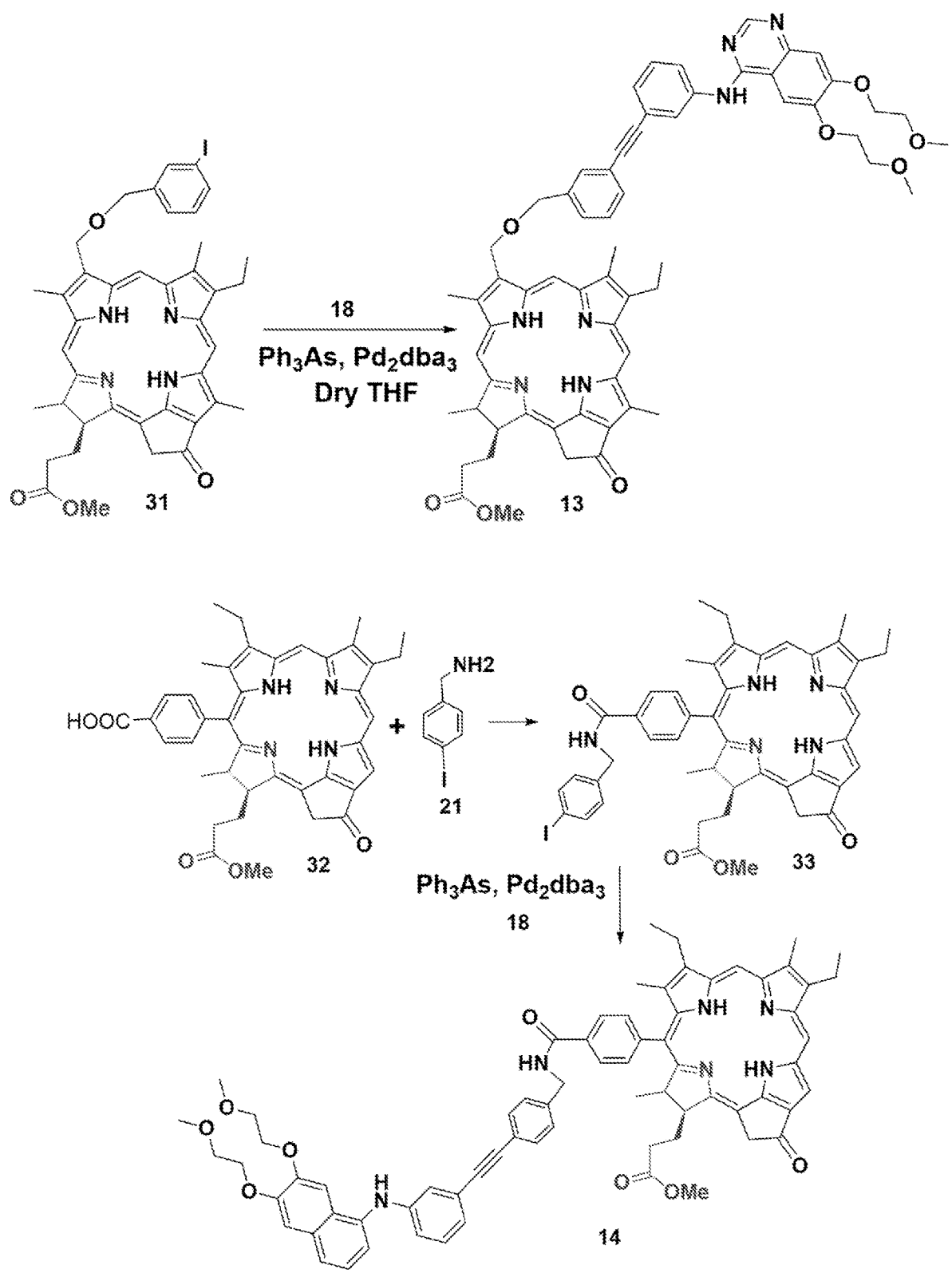
FIG. 21 shows the synthesis of modified erlotinib analogs.

Part 6: Synthesis of modified erlotinib analogs: In our efforts to develop galectin-3 and integrin targeted photosensitizers, we observed that the nature of linker joining the targeted moiety makes a significant difference in receptor binding ability. Therefore, certain functionalities (e. g., amino, carboxylic acid were introduced in erlotinib. Such modifications provide an opportunity to introduce erlotinib at various peripheral positions of functionalized symmetrical or unsymmetrical photosensitizers with desired photophysical properties. See FIGS. 19-21.

Following methods were used for the preparation of the conjugates 1-14, where the erlotinib moiety was conjugated at various peripheral positions of the PS. For example, the synthesis of compound 1, erlotinib was reacted with aziodobutylamine by following the standard methodology, the corresponding amino analog 19 was then conjugated with HPPH 20 containing a carboxylic acid functionality and the final product 1 was isolated in good yield.

Conjugate 3 was synthesized by reacting HPPH 20 with 4-iodo phenyl hydrazine, which again reacted with erlotinib under Suzuki reaction conditions.

It was previously shown that in a series of alkyl- and aryl ether analogs of pyropheophorbide-a, the presence of chirality at position $3^1$ plays an important role in photosensitizing activity. Replacing the methyl group at this position with hydrogen significantly reduce its biological efficacy. Therefore, the iodinated PS 31 without having a chiral center at position-$3^1$ was synthesized by following our own methodology and reacted with 18 by following the methodology discussed above and the desired conjugate 13 was isolated in modest yield.

For introducing erlotinib at position-20 of the PS, 20-benzoic acid mesopyro-pheophorbide-a methyl ester 32 was synthesized by following our own methodology. Reaction of 30 with 4-iodobenzylamine gave the intermediate 33, which on further reacting with 18 afforded the desired conjugate 14 in good yield.

The detailed synthetic and characterization details of the PS-erlotinib conjugates 1-14 are described in the herein.

Part 7: Multifunctional agents for PET/Fluorescence with an option of PDT.

Figure 22:
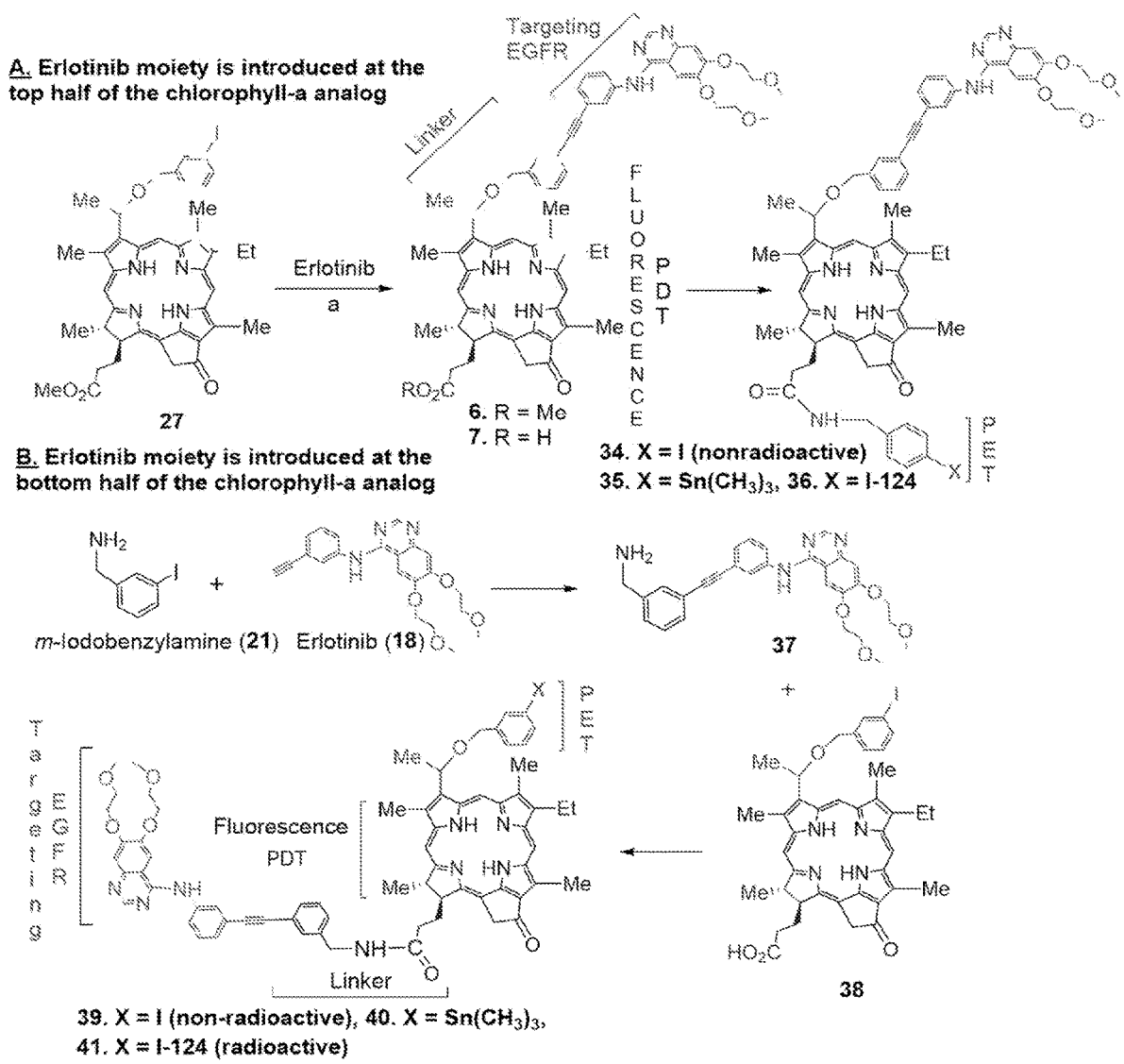
FIG. 22 shows dual imaging agents 36 and 41.

(a) Conjugation of photosensitizer with erlotinib: the desired dual imaging agents 36 and 41 with an option of PDT were synthesized by following the methodology depicted below. See FIG. 22.

Figure 23:
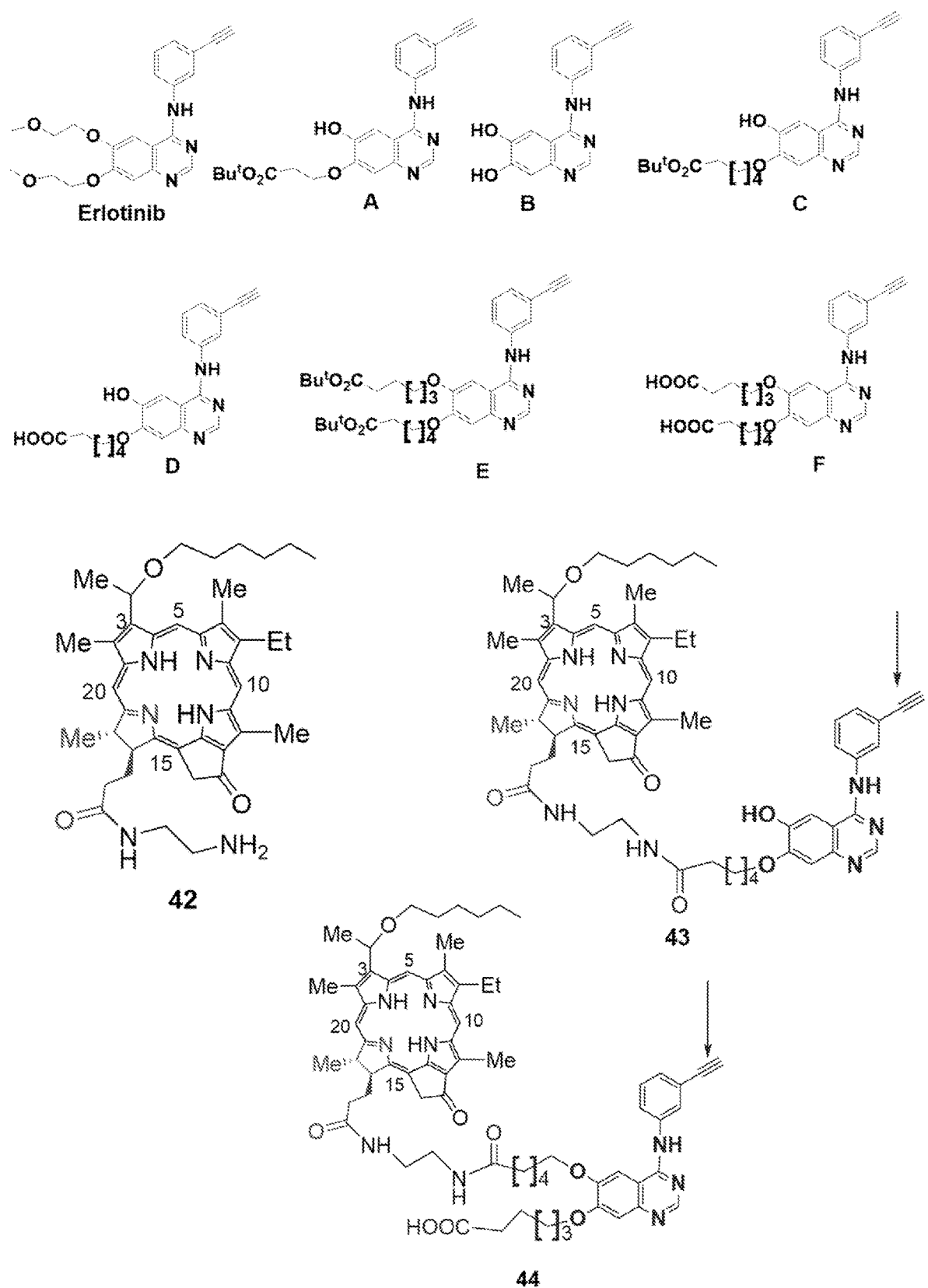
FIG. 23 shows the structures of 43 and 44.

(b) Conjugation of photosensitizer with modified erlotinib: to investigate the impact of modified erlotinib analogs, erlotinib was modified by introducing such functionalities which could be conjugated to the photosensitizer, and a series of conjugates were prepared. The structures of the conjugates 43, 44 prepared so far are as in FIG. 23.

Photophysical properties of the conjugates. For the synthesis of the desired conjugates, the starting materials (methyl pyropheophorbide-a and bacteriopheophorbide-a methyl ester) were derived from chlorophyll-a and bactewrioochlorophyll-a, which in turn were isolated from *spirulina algae* and *Rhodobacter sphaeroides*. In general, monopyrrole reduced conjugates with five member exocyclic ring 6 showed long wavelength absorption near 660 nm, whereas the six member fused imide ring 4 system exhibited the long wavelength absorption at 705 nm. The corresponding bacteriochlorins in which two pyrrole rings diagonal to each other were reduced extended the long wavelength absorption significantly. For example bacteriochlorin conjugate 8 bearing a five member ring showed long wavelength absorption at 720 nm, whereas in conjugate 10 with a fused imide ring the long wavelength absorption was observed at 787 nm. These long wavelength absorbing photosensitizers provide an opportunity to treat large and deeply seated tumors (longer the wavelength deeper the tissue penetration of light), and could also limit the number of optical fibers for the PDT treatment, which could make PDT treatment more economical.

The absorption spectra of the selected conjugates 4, 6, 8 and 10 are shown in FIG. 1.

Experimental Details and Characterization of Compounds

Synthesis of conjugate 1: To a solution of HPPH (20) (30 mg, 0.0471 mmol) and compound 19 (47.82 mg, 0.0942 mmol.) in 8 mL of dry dichloromethane, 1-ethyl-3-(3-dimethylamino propyl)-carbodiimide (EDC, 14.62 mg, 0.0942 mmol) and 4-(dimethylamino(pyridine (DMAP, 11.50 mg, 0.0942 mmol) were added. The reaction mixture was stirred at room temperature under $N_2$ atmosphere for overnight. It was then diluted with dichloromethane (40 mL), washed with water (3×50 mL), dried over anhydrous sodium sulfate and concentrated down to yield crude product which was purified by preparative plate by using 20% methanol in dichloromethane to obtain pure final product 1 with 32% yield (15.91 mg). $^1$H NMR (400 MHz, CDCl$_3$, δ ppm): 9.76/9.723 (s, 1H), 8.80 (br s, 1H), 8.67 (s, 1H), 8.62 (s, 1H), 8.472/8.467 (s, 1H), 8.10 (d, J=6.8, 1H), 7.97 (d, J=7.2 Hz, 1H), 7.75 (s, 1H), 7.20-7.38 (m, 4H), 6.25-6.34 (m, 1H), 5.89 (m, 1H), 5.28 (d, J=19.8 Hz, 1H), 4.98 (d, J=19.7 Hz, 1H), 4.43-4.54 (m, 1H), 4.22-4.32 (m, 5H), 3.75-3.86 (m, 4H), 3.68-3.73 (m, 3H), 3.64-3.68 (m, 2H), 3.57-3.64 (m, 1H), 3.47-3.57 (m, 1H), 3.38-3.47 (m, 2H), 3.45 (s, 3H), 3.35/3.34 (s, 3H), 3.311/3.307 (s, 3H), 3.25/3.24 (s, 3H), 2.96-3.06 (m, 1H), 2.85-2.94 (m, 1H), 2.74-2.84 (br s, 1H), 2.64-2.74 (m, 1H), 2.43-2.56 (m, 1H), 2.30-2.41 (m, 1H), 2.10/2.11 (d, J=6.3 Hz, 3H), 1.98-2.07 (m, 2H), 1.67-1.81 (m, 8H), 1.47-1.56 (m, 2H), 1.30-1.47 (m, 2H), 1.17-1.27 (m, 4H), 0.78 (m, 3H), 0.41 (br s, 1H), −1.60/−1.59 (br s, 1H). MS (ESI) m/z: 1126.61 (M+H+). HRMS (ESI): calcd for C$_{65}$H$_{80}$N$_{11}$O$_7$ (M+H+) 1126.6197; found, 1126.6199. UV-vis (CH$_3$OH, λ$_{max}$, nm (abs)): 662 (0.212), 605 (0.040), 539 (0.040), 507 (0.040), 409 (0.403), 347 (0.218).

Synthesis of Conjugate 2: To a solution of HPPH 20 (50 mg, 0.0785 mmol) and 3-Ido benzyl amine 21 (27.5 mg, 0.1178 mmol) in 10 mL of dry dichloromethane, 1-ethyl-3-(3-dimethylaminopropyl)-carbodiimide hydro chloride (EDCI, 30.0 mg, 0.1571 mmol) and 4-(dimethylamino(pyridine (DMAP, 19.2 mg, 0.158 mmol) were added. The reaction mixture was stirred at room temperature under N$_2$ atmosphere for overnight. It was then diluted with dichloromethane (40 mL), washed with water (3×50 mL), dried over anhydrous sodium sulfate and concentrated down to yield crude product which was purified by Silica column by using 2% methanol in dichloromethane to obtain pure product 22 with 89% (59.52 mg) yield. Tryphenylarsine (8.62 mg, 0.0281 mmol) and Pd2dba3 (12.89 mg, 0.014 mmol) were added to a stirred solution of compound 22 (30 mg, 0.0352 mmol) and Erlotinib (20.78 mg, 0.0528 mmol) in dry THF (20 mL) and Et$_3$N (4 mL). The reaction mixture was stirred at room temperature under an argon atmosphere overnight. As per TLC only ¾ amount of the starting material reacted to produce the desired product. The remaining ¼ unreacted even by increasing the catalyst quantity, temperature and duration of the reaction. The desired conjugate 2 and the remaining starting material 22 were purified by preparative TLC plates with 75% yield (29.51 mg). $^1$H NMR (400 MHz, CDCl$_3$, δ ppm): 9.79/9.76 (s, 1H), 8.90-9.00 (m, 2H), 8.68 (s, 1H), 8.49 (s, 1H), 8.21 (dd, J=1.0, 8.0 Hz, 1H), 7.85 (d, J=1.0 Hz, 1H), 7.64 (m, 1H), 7.42 (s, 1H), 7.28-7.35 (m, 2H), 7.20-7.24 (m, 2H), 7.17 (br s, 1H), 7.02 (ddd, J=1.5, 7.6, 7.6 Hz, 1H), 6.91 (d, J=7.4 Hz, 1H), 5.90/5.91 (q, J=6.8 Hz, 1H), 5.07 (d, J=19.8, 1H), 4.46-4.57 (m, 2H), 4.40 (dd, J=6.3, 14.8 Hz, 1H), 4.16-4.29 (m, 5H), 3.95-4.03 (m, 1H), 3.81 (m, 2H), 3.63-3.74 (m, 2H), 3.62 (m, 2H), 3.48-3.62 (m, 2H), 3.44 (s, 3H), 3.372/3.365 (s, 3H), 3.29 (s, 3H), 3.234/3.232 (s, 3H), 2.82 (m, 1H), 2.67 (m, 1H), 2.22-2.37 (m, 4H), 2.13/2.12 (d, J=6.7 Hz, 3H), 2.04 (m, 1H), 1.71-1.82 (m, 5H), 1.63/1.62 (t, J=7.6 Hz, 3H), 1.32-1.53 (m, 2H), 1.18-1.32 (m, 4H), 0.76-0.84 (m, 3H), 0.62 (br s, 1H), −1.48/−1.49 (s, 1H). MS (ESI) m/z: 1117.58 (M+H+). HRMS (ESI): calcd for C$_{68}$H$_{77}$N$_8$O$_7$ (M+H+) 1117.5871; found, 1117.5897. UV-vis (CH$_3$OH, λ$_{max}$, nm (abs)): 662 (0.259), 606 (0.050), 538 (0.051), 507 (0.049), 409 (0.482), 346 (0.286).

Synthesis of Conjugate 4: Tryphenylarsine (9.25 mg, 0.0302 mmol) and Pd$_2$dba$_3$ (13.84 mg, 0.0151 mmol) were added to a stirred solution of compound 25 (30 mg, 0.0377 mmol) and erlotinib (22.30 mg, 0.0569 mmol) in dry THF (10 mL) and Et$_3$N (2.5 mL). The reaction mixture was stirred at room temperature under an argon atmosphere overnight. As per TLC only ½ amount of the starting material reacted to produce the desired product. The remaining ½ unreacted even by increasing the catalyst quantity, temperature and duration of the reaction. The product 4 was purified by preparative TLC plates with 68% yield (27.22 mg). $^1$H NMR (400 MHz, CDCl$_3$, δ ppm): 9.56 (s, 1H), 9.32 (s, 1H), 8.61 (s, 1H), 8.56 (s, 1H), 7.85-7.92 (m, 2H), 7.72 (s, 1H), 7.59 (s, 2H), 7.41 (m, 1H), 7.29-7.38 (m, 3H), 7.19-7.28 (m, 3H), 6.27 (dd, J=1.3, 17.8 Hz, 1H), 6.15 (dd, J=1.3, 11.5 Hz, 1H), 5.73 (d, J=14.4 Hz, 1H), 5.62 (d, J=14.4 Hz, 1H), 5.40 (m, 1H), 4.34 (q, J=7.3 Hz, 1H), 4.23-4.29 (m, 2H), 4.20 (t, J=4.7 Hz, 2H), 3.84 (m, 2H), 3.79 (s, 3H), 3.75 (m, 2H), 3.60 (q, J=7.6 Hz, 2H), 3.51 (s, 3H), 3.46 (s, 3H), 3.40 (s, 3H), 3.34 (s, 3H), 3.13 (s, 3H), 2.74 (m, 1H), 2.33-2.52 (m, 2H), 2.01 (m, 1H), 1.77 (d, J=7.2 Hz, 3H), 1.64 (t, J=7.7 Hz, 3H), 0.01 (br s, 1H), −0.10 (br s, 1H). MS (ESI) m/z: 1159.47 (M+H+). HRMS (ESI): calcd for C$_{63}$H$_{63}$N$_8$O$_8$ (M+H+) 1159.4724; found, 1159.4745. UV-vis (CH$_3$OH, λ$_{max}$, nm (abs)): 707 (0.430), 652 (0.083), 555 (0.224), 513 (0.062), 482 (0.047), 416 (1.132), 348 (0.659).

Synthesis of Conjugate 5: Tryphenylarsine (8.44 mg, 0.0275 mmol) and Pd$_2$dba$_3$ (12.63 mg, 0.0137 mmol) were added to a stirred solution of compound 26 (30 mg, 0.0344 mmol) and Erlotinib (20.34 mg, 0.0517 mmol) in dry THF (10 mL) and Et$_3$N (2.5 mL). The reaction mixture was stirred at room temperature under an argon atmosphere overnight. As per TLC only ½ amount of the starting material reacted to produce the desired product. The remaining ½ unreacted even by increasing the catalyst quantity, temperature and duration of the reaction. The product 5 was purified by preparative TLC plates with 75% yield (29.36 mg). $^1$H NMR (400 MHz, CDCl$_3$, δ ppm): 8.83/8.78 (s, 1H), 8.64 (s, 1H), 8.57 (s, 1H), 8.30 (s, 1H), 7.84-7.93 (m, 3H), 7.67 (d, J=7.8 Hz, 1H), 7.59 (s, 1H), 7.40 (s, 1H), 7.24-7.37 (m, 3H), 7.18-7.23 (m, 2H), 5.68 (d, J=14.4 Hz, 1H), 5.65/5.63 (q, J=6.9 Hz, 1H), 5.57 (d, J=14.5 Hz, 1H), 5.26 (m, 1H), 4.11-4.26 (m, 6H), 3.99 (m, 1H), 3.82 (m, 2H), 3.72 (m, 2H), 3.49-3.64 (m, 2H), 3.60 (s, 3H), 3.517/3.515 (s, 3H), 3.45 (s, 3H), 3.38/3.37 (s, 3H), 3.23/3.22 (s, 3H), 2.68 (m, 1H), 2.26-2.45 (m, 3H), 1.94-2.10 (m, 2H), 1.99 (d, J=6.7 Hz, 3H), 1.79/1.78 (d, J=7.1 Hz 3H), 1.62-1.75 (m, 2H), 1.69 (d, J=7.3 Hz 3H), 1.30-1.54 (m, 2H), 1.12/1.09 (t, J=7.3 Hz, 3H), 0.87/0.86 (t, J=7.4 Hz, 3H), 0.22 (s, 1H), −0.17 (s, 1H). MS (ESI) m/z: 1135.56 (M+H+). HRMS (ESI): calcd for C$_{67}$H$_{75}$N$_8$O$_9$ (M+H+) 1135.5612; found, 1135.5635. UV-vis (CH$_3$OH, λ$_{max}$, nm (abs)): 783 (0.114), 538 (0.109), 415 (0.120), 366 (0.295), 343.9 (0.356).

Synthesis of Conjugate 6: Tryphenylarsine (18.76 mg, 0.06132 mmol) and Pd$_2$dba$_3$ (28.06 mg, 0.0306 mmol) were added to a stirred solution of compound 27 (60 mg, 0.0766) and erlotinib (45.22 mg, 0.1144) in dry THF (30 mL) and Et$_3$N (6 mL). The reaction mixture was stirred at room temperature under an argon atmosphere overnight. As per TLC only ¾ amount of the starting material reacted to produce the desired product. The remaining ¼ unreacted even by increasing the catalyst quantity, temperature and duration of the reaction. The product 6 and the remaining starting material 27 were purified by preparative TLC plates with 72% yield (57.85 mg). $^1$H NMR (400 MHz, CDCl$_3$, δ ppm): 9.75/9.73 (s, 1H), 9.47/9.46 (s, 1H), 8.66 (s, 1H), 8.55 (s, 1H), 7.72-7.78 (m, 2H), 7.53 (m, 1H), 7.45 (m, 1H), 7.28-7.34 (m, 3H), 7.19-7.24 (m, 2H), 7.16 (s, 1H), 7.13-7.16 (m, 1H), 6.01 (q, J=6.7 Hz, 1H), 5.25 (d, J=19.9 Hz, 1H), 5.11 (d, J=19.9 Hz, 1H), 4.76 (d, J=11.8 Hz, 1H), 4.61/4.60 (d, J=11.8 Hz, 1H), 4.48 (dq, J=1.8, 7.3 Hz, 1H), 4.22-4.32 (m, 5H), 3.84 (m, 2H), 3.74 (t, J=4.8 Hz, 2H), 3.58-3.66 (m, 5H), 3.463/3.462 (s, 3H), 3.44/3.43 (s, 3H), 3.407/3.405 (s, 3H), 3.38 (s, 3H), 3.199/3.193 (s, 3H), 2.63-2.74 (m, 1H), 2.50-2.61 (m, 1H), 2.21-2.37 (m, 2H), 2.15 (d, J=6.7 Hz, 3H), 1.82 (d, J=7.2 Hz, 3H), 1.64 (t, J=7.6, 3H), 0.43 (br s, 1H), −1.70 (br s, 1H). MS (ESI) m/z: 1048.49 (M+H+). HRMS (ESI): calcd for $C_{63}H_{66}N_7O_8$ (M+H+) 1048.4928; found, 1048.4957. UV-vis ($CH_3OH$, $\lambda_{max}$, nm (abs)): 662 (0.235), 605 (0.044), 537 (0.049), 507 (0.047), 408 (0.465), 348 (0.299).

Synthesis of Conjugate 7: Aqueous LiOH (36.02 mg in 3 mL of $H_2O$) was added to a solution of compound 6 (30 mg) in dry THF:MeOH (4.5:3 mL), and the reaction mixture was stirred under argon at room temperature for 2 h. The reaction mixture was diluted with $CH_2Cl_2$ (50 mL) and washed with 2% AcOH in $H_2O$ (18 mL) and with $H_2O$ (3×50 mL), and the organic layer was dried over $Na_2SO_4$, concentrated, and purified over a preparative TLC plate using 8% MeOH in $CH_2Cl_2$ as eluent to yield 28.11 mg (95%) of product 7. $^1H$ NMR (400 MHz, 90:10 $CDCl_3/CD_3OD$, δ ppm): 9.61 (s, 1H), 9.22 (br s, 1H), 8.47 (s, 1H), 8.41 (s, 1H), 7.68 (d, J=7.6 Hz, 1H), 7.63/7.58 (s, 1H), 7.36-7.46 (m, 5H), 7.23-7.32 (m, 2H), 7.14 (s, 1H), 7.09 (d, J=7.4 Hz, 1H), 5.94 (m, 1H), 5.19 (d, 1H), 4.95 (d, 1H), 4.69 (d, 1H), 4.56 (d, 1H), 4.25-4.45 (m, 6H), 3.86 (m, 2H), 3.73 (m, 2H), 3.47 (s, 3H), 3.42 (s, 3H), 3.33-3.48 (m, 5H), 3.26-3.32 (s, 3H), 3.10/3.08 (s, 3H), 2.61 (br s, 1H), 2.47 (br s, 1H), 2.08 (s, 3H), 2.05-2.35 (m, 2H), 1.67 (br s, 3H), 1.51 (br s, 3H). MS (ESI) m/z: 1034.48 (M+H+). HRMS (ESI): calcd for $C_{62}H_{64}N_7O_8$ (M+H+) 1034.4814; found, 1034.4821. UV-vis ($CH_3OH$, $\lambda_{max}$, nm (abs)): 662 (0.235), 605 (0.044), 537 (0.049), 507 (0.047), 408 (0.465), 348 (0.299).

Synthesis of Conjugate 8: Tryphenylarsine (18.72 mg, 0.0611 mmol) and Pd2dba3 (28.00 mg, 0.0305 mmol) were added to a stirred solution of compound 28 (60 mg, 0.07643 mmol) and Erlotinib (45.10 mg, 0.1146 mmol) in dry THF (30 mL) and $Et_3N$ (6 mL). The reaction mixture was stirred at room temperature under an argon atmosphere overnight. As per TLC only ¾ amount of the starting material reacted to produce the desired product. The remaining ¼ unreacted even by increasing the catalyst quantity, temperature and duration of the reaction. The product 8 and the remaining starting material 28 were purified by preparative TLC plates with 72% yield (57.79 mg). $^1H$ NMR (400 MHz, $CDCl_3$, δ ppm): 8.65/8.64 (s, 1H), 8.55/8.47 (s, 1H), 8.19 (s, 1H), 8.029/8.025 (s, 1H), 7.90 (m, 1H), 7.70 (m, 1H), 7.49 (m, 1H), 7.44 (m, 2H), 7.33 (m, 1H), 7.24-7.30 (m, 4H), 7.20 (m, 1H), 5.73 (q, J=6.7 Hz, 1H), 4.95 (d, J=19.8 Hz, 1H), 4.78 (d, J=19.8 Hz, 1H), 4.69/4.66 (d, J~11.8 Hz, 1H), 4.57/4.53 (d, J~11.8 Hz, 1H), 4.25-4.34 (m, 4H), 4.14 (dq, J=7.2, 2.0 Hz, 1H), 4.08 (m, 1H), 3.99 (m, 1H), 3.80-3.89 (m, 5H), 3.610/3.608 (s, 3H), 3.472 (s, 3H), 3.466/3.462 (s, 3H), 3.33 (s, 3H), 3.146/3.143 (s, 3H), 2.42-2.59 (m, 2H), 2.16-2.33 (m, 3H), 2.05/2.04 (d, J=6.6 Hz, 3H), 1.95-2.07 (m, 1H), 1.74/1.67 (d, J=7.20 Hz, 3H), 1.68/1.66 (d, J=7.1 Hz, 3H), 1.33/1.32 (br s, 1H), 1.09/1.07 (t, J=7.4 Hz, 3H), −0.17/−0.18 (br s, 1H). MS (ESI) m/z: 1050.50 (M+H+). HRMS (ESI): calcd for $C_{63}H_{68}N_7O_8$ (M+H+) 1050.5051; found, 1050.5049. UV-vis ($CH_3OH$, $\lambda_{max}$, nm (abs)): 714 (0.136), 652 (0.057), 609 (0.026), 517 (0.102), 486 (0.032), 350 (0.443).

Synthesis of Conjugate 9: Aqueous LiOH (36.00 mg in 3 mL of $H_2O$) was added to a solution of compound 8 (30 mg) in dry THF:MeOH (4.5:3 mL), and the reaction mixture was stirred under argon at room temperature for 2 h. The reaction mixture was diluted with $CH_2Cl_2$ (50 mL) and washed with 2% AcOH in $H_2O$ (18 mL) and with $H_2O$ (3×50 mL), and the organic layer was dried over $Na_2SO_4$, concentrated, and purified over a preparative TLC plate using 8% MeOH in $CH_2Cl_2$ as eluent to yield 28.06 mg (95%) of product 9. $^1H$ NMR (400 MHz, $CDCl_3$, δ ppm): 8.54/8.28 (s, 1H), 8.33/8.23 (s, 1H), 8.10/8.08 (s, 1H), 8.00/7.96 (s, 1H), 7.79/7.73 (s, 1H), 7.51 (d, J=7.0 Hz, 1H), 7.27-7.39 (m, 3H), 7.05-7.25 (m, 4H), 7.00 (m, 1H), 5.72/5.58 (q, J=6.7 Hz, 1H), 4.95 (d, J=19.7 Hz, 1H), 4.75 (d, J=19.7 Hz, 1H), 4.63 (d, J=12.3 Hz, 1H), 4.47 (d, J=12.3 Hz, 1H), 4.10-4.25 (m, 5H), 4.06 (m, 1H), 3.97 (d, J=6.8 Hz, 1H), 3.72-3.83 (m, 3H), 3.70 (br s, 2H), 3.40 (s, 3H), 3.34 (s, 3H), 3.23/3.22 (s, 3H), 3.12/2.97 (s, 3H), 2.40-2.55 (m, 2H), 2.15-2.34 (m, 3H), 2.01/1.99 (d, J=6.7 Hz, 3H), 1.90-2.02 (m, 1H), 1.71/1.66 (d, J=7.2 Hz, 3H), 1.632/1.628 (d, J=7.1 Hz, 3H), 1.43/1.35 (s, 1H), 1.07/1.05 (t, J=7.2 Hz, 3H), −0.07/−0.13 (br s, 1H). MS (ESI) m/z: 1036.48 (M+H+). HRMS (ESI): calcd for $C_{62}H_{66}N_7O_8$ (M+H+) 1036.4895; found, 1036.4898. UV-vis (CH3OH, $\lambda_{max}$, nm (abs)): 715 (0.619), 652 (0.263), 609 (0.121), 518 (0.479), 487 (0.154), 349 (1.988).

Synthesis of Conjugate 10: Tryphenylarsine (8.44 mg, 0.0275 mmol) and $Pd_2dba_3$ (12.63 mg, 0.0137 mmol) were added to a stirred solution of compound 29 (30 mg, 0.0344 mmol) and Erlotinib (20.34 mg, 0.0517 mmol) in dry THF (10 mL) and Et3N (2.5 mL). The reaction mixture was stirred at room temperature under an argon atmosphere overnight. As per TLC only ½ amount of the starting material reacted to produce the desired product. The remaining ½ unreacted even by increasing the catalyst quantity, temperature and duration of the reaction. The product 10 was purified by preparative TLC plates with 71% yield (27.79 mg). $^1H$ NMR (400 MHz, $CDCl_3$, δ ppm): 8.83/8.75 (s, 1H), 8.65 (s, 1H), 8.60 (s, 1H), 8.35 (s, 1H), 7.86-7.90 (m, 1H), 7.64-7.69 (m, 1H), 7.40-7.53 (m, 3H), 7.27-7.33 (m, 4H), 7.23 (s, 1H), 7.16 (m, 1H), 5.77/5.76 (q, 1H, J=6.7 Hz), 5.26 (m, 1H), 4.53-4.72 (m, 2H), 4.42 (m, 2H), 4.23-4.30 (m, 4H), 4.11-4.23 (m, 2H), 3.99 (m, 1H), 3.84 (m, 2H), 3.80 (m, 2H), 3.62 (s, 3H), 3.564/3.561 (s, 3H), 3.46 (s, 3H), 3.443/3.440 (s, 3H), 3.22 (s, 3H), 2.64 (m, 1H), 2.23-2.43 (m, 3H), 2.07 (t, J=6.7 Hz, 3H), 1.88-2.09 (m, 4H), 1.78/1.71 (d, J=7.2 Hz, 3H), 1.694/1.686 (d, J=7.2 Hz, 3H), 1.61 (m, 2H), 1.05-1.12 (m, 3H), 1.07 (t, J=7.4 Hz, 3H), −0.02/−0.03 (s, 1H), −0.34/−0.36 (s, 1H). MS (ESI) m/z: 1135.56 (M+H+). HRMS (ESI): calcd for $C_{67}H_{75}N_8O_9$ (M+H+) 1135.5646; found, 1135.5630. UV-vis ($CH_3OH$, $\lambda_{max}$, nm (abs)): 787 (0.236), 538 (0.194), 417 (0.226), 366 (0.518), 343.9 (0.442).

Synthesis of Conjugate 12: Tryphenylarsine (9.38 mg, 0.0306 mmol) and $Pd_2dba_3$ (14.03 mg, 0.0153 mmol) were added to a stirred solution of compound 30 (30 mg) and Erlotinib (22.61 mg, 0.0572 mmol) in dry THF (10 mL) and $Et_3N$ (2.5 mL). The reaction mixture was stirred at room temperature under an argon atmosphere overnight. As per TLC only ½ amount of the starting material reacted to produce the desired product. The remaining ½ unreacted even by increasing the catalyst quantity, temperature and duration of the reaction. The product 12 was purified by preparative TLC plates with 55% yield (22.09 mg). $^1H$ NMR (400 MHz, $CDCl_3$, δ ppm): 9.75 (s, 1H), 9.53 (s, 1H), 8.68 (s, 1H), 8.55 (s, 1H), 7.92 (s, 1H), 7.73 (m, 1H), 7.46-7.50 (m, 2H), 7.29-7.41 (m, 5H), 7.22-7.26 (m, 2H), 6.00 (q, J=6.7 Hz, 1H), 5.27/5.26 (d, J=19.8 Hz, 1H), 5.12/5.11 (d, J=19.9 Hz, 1H), 4.76 (d, J=12.2 Hz, 1H), 4.63/4.62 (d, J=12.2 Hz, 1H), 4.49 (dq, J=1.8, 7.3 Hz, 1H), 4.24-4.33 (m, 5H), 3.80-3.89 (m, 4H), 3.707 (q, J=7.6 Hz, 2H), 3.68 (s, 3H), 3.61/3.60 (s, 3H), 3.474 (s, 3H), 3.468 (s, 3H), 3.37/3.36 (s, 3H), 3.20/3.19 (s, 3H), 2.69 (m, 1H), 2.56 (m, 1H), 2.20-2.38 (m, 3H), 2.17/2.16 (d, J=6.7 Hz, 3H), 1.823/1.816 (d, J=7.3 Hz, 3H), 1.71 (t, J=7.6 Hz, 3H), 0.43 (br s, 1H), −1.71 (br s, 1H). MS (ESI) m/z: 1048.49 (M +H+). FIRMS (ESI): calcd for $C_{63}H_{66}N_7O_8$ (M+H+) 1048.4928; found, 1048.4954. UV-vis (CH$_3$OH, $\lambda_{max}$, nm (abs)): 661 (0.425), 606 (0.077), 537 (0.084), 506 (0.081), 407 (0.818), 334 (1.010).

Synthesis of Conjugate 13: Tryphenylarsine (6.37 mg, 0.0208 mmol) and Pd$_2$dba$_3$ (28.06 mg, 0.0104 mmol) were added to a stirred solution of compound 31 (20 mg, 0.0260 mmol) and Erlotinib (15.35 mg, 0.0390 mmol) in dry THF (15 mL) and Et$_3$N (2 mL). The reaction mixture was stirred at room temperature under an argon atmosphere overnight. As per TLC only ¾ amount of the starting material reacted to produce the desired product. The remaining ¾ unreacted even by increasing the catalyst quantity, temperature and duration of the reaction. The product 13 was purified by preparative TLC plates with 73% yield (19.64 mg). $^1$H NMR (400 MHz, CDCl$_3$, δ ppm): 9.43 (s, 1H), 9.37 (s, 1H), 8.66 (s, 1H), 8.54 (s, 1H), 7.70-7.78 (m, 2H), 7.64 (s, 1H), 7.49 (m, 1H), 7.43 (m, 1H), 7.27-7.39 (m, 3H), 7.18-7.23 (m, 2H), 7.07 (s, 1H), 5.68 (s, 2H), 5.25 (d, J=19.8 Hz, 1H), 5.10 (d, J=19.8 Hz, 1H), 4.80 (s, 2H), 4.47 (dq, J=1.9, 7.3 Hz, 1H), 4.24-4.32 (m, 3H), 4.10 (m, 2H), 3.84 (m, 2H), 3.70 (m, 2H), 3.61 (s, 3H), 3.60 (s, 3H), 3.56-3.63 (m, 2H), 3.47 (s, 3H), 3.39 (s, 3H), 3.34 (s, 3H), 3.18 (s, 3H), 2.69 (m, 1H), 2.56 (m, 1H), 2.23-2.35 (m, 2H), 1.81 (d, J=7.3 Hz, 3H), 1.63 (t, J=7.6 Hz, 3H), 0.37 (br s, 1H), −1.77 (s, 1H). MS (ESI) m/z: 1034.47 (M+H+). HRMS (ESI): calcd for $C_{62}H_{64}N_7O_8$ (M+H+) 1034.4772; found, 1034.4795. UV-vis (CH$_3$OH, $\lambda_{max}$, nm (abs)): 664 (0.207), 606 (0.039), 537 (0.041), 507 (0.041), 410 (0.398), 347 (0.262).

Synthesis of compound 33: 44.6 mg (0.067 mmol) of 1, synthesized using a previously established method, was dissolved in 10 ml of dichloromethane (DCM) dried over molecular sieves. To this 73.5 mg (0.166 mmol) of (Benzotriazol-1-yloxy)tris(dimethylamino) phosphonium hexafluorophosphate (BOP) and 250 μL (0.1806 g; 1.785 mmol) of trimethylamine was added and the reaction mixture was allowed to stir for 30 minutes under Ar. To the reaction mixture, 35.6 mg (0.153 mmol) of 4-Iodobenzylamine HCl was added. The reaction was allowed to stir overnight, protected from light and under Ar atmosphere. TLC in 3% methanol (MeOH) in DCM showed a disappearance of the starting material 1. The reaction mixture was diluted with DCM and washed once with 1M HCl, twice with DI H$_2$O and once with brine (saturated sodium chloride). The organic layer was dried over anhydrous Na$_2$SO$_4$. The organic solution was filtered and concentrated using a rotoary evaporator and dried using a high vacuum pump. The crude reaction mixture was purified using preparation TLC (3% MeOH in DCM). The desired product was collected with an Rf value of about 0.61. The desired product was filtered off the silica gel using 50% MeOH in DCM. The organics were removed and concentrated using a rotary evaporator and dried using a high vacuum pump. Yield 49.5 mg (84%). $^1$H NMR (400 MHz, CDCl$_3$, δ ppm): 9.50 (s, 1H), 9.37 (s, 1H), 8.21 (dd, J=7.9, 1.5 Hz, 1H), 8.18 (dd, J=7.9, 1.2 Hz, 1H), 8.05 (dd, J=7.9, 1.4 Hz, 1H), 7.71-7.78 (m, 3H), 7.25 (m, 2H), 6.78 (t, J=5.7 Hz, 1H), 5.20 (d, J=19.9 Hz, 1H), 5.15 (d, J=19.9 Hz, 1H), 4.69-4.79 (m, 2H), 4.19 (q, J=7.1 Hz, 1H), 4.06 (dd, J=8.4, 3.5 Hz, 1H), 3.77 (q, J=7.7 Hz, 2H), 3.71 (q, J=7.7 Hz, 2H), 3.67 (s, 3H), 3.55 (s, 3H), 3.28 (s, 3H), 2.33-2.57 (m, 2H), 2.27 (s, 3H), 2.11-2.24 (m, 2H), 1.72 (t, J=7.7 Hz, 3H), 1.63 (t, J=7.7 Hz, 3H), 1.02 (d, J=7.1 Hz, 3H), −1.46 (br s, 1H). HRMS (ESI) for $C_{48}H_{48}IN_5O_4$ [MH$^+$] calculated: 886.28237; found: 886.28239. UV-Vis (MeOH, $\lambda_{max}$, nm): 270, 410, 510, 545 610, 665.

Synthesis of conjugate 14: 20.0 mg (0.065 mmol) of triphenylarsine (AsPh$_3$) and 22.0 mg (0.024 mmol) of Tris (dibenzylideneacetone)dipalladium(0) [Pd$_2$(dba)$_3$] were added to a stirred solution of 49.5 mg (0.056 mmol) of 2, 34.1 mg (0.087 mmol) of Erlotinib and 4 ml (2.89 g; 28.56 mmol) of trimethylamine in 30 ml of freshly distilled THF under an atmosphere of Ar. The reaction was allowed to stir overnight, protected from light and under Ar atmosphere. TLC in 5% methanol (MeOH) in DCM showed a disappearance of the starting material 1. The reaction mixture was diluted with DCM and washed once with 1M HCl, twice with DI H$_2$O and once with brine (saturated sodium chloride). The organic layer was dried over anhydrous Na$_2$SO$_4$. The organic solution was filtered and concentrated using a rotoary evaporator and dried using a high vacuum pump. The crude reaction mixture was purified using preparation TLC (4% MeOH in DCM). The desired product was collected with an Rf value of about 0.24. The desired product was filtered off the silica gel using 50% MeOH in DCM. The organics were removed and concentrated using a rotary evaporator and dried using a high vacuum pump. Yield: 25.7 mg (40%). $^1$H NMR (400 MHz, CDCl$_3$, δ ppm) 9.48 (s, 1H), 9.34 (s, 1H), 8.60 (s, 1H), 8.24 (dd, J=1.7, 7.9 Hz, 1H), 8.17 (dd, J=1.6, 7.9 Hz, 1H), 8.09 (dd, J=1.7, 7.9 Hz, 1H), 8.0 (br s, 1H), 7.94 (s, 1H), 7.70-7.76 (m, 2H), 7.49 (m, 2H), 7.43 (br s, 1H), 7.39 (m, 2H), 7.31-7.37 (m, 1H), 7.28 (m, 1H), 7.24 (s, 1H), 7.04 (br s, 1H), 5.14 (m, 2H), 4.76 (m, 2H), 4.33 (m, 2H), 4.25 (m, 2H), 4.17 (q, J=7.1 Hz, 1H), 4.03 (dd, J=3.6, 8.2 Hz, 1H), 3.80-3.86 (m, 4H), 3.74 (q, J=7.6 Hz, 2H), 3.69 (q, J=7.6 Hz, 2H), 3.65 (s, 3H), 3.53 (s, 3H), 3.461 (s, 3H), 3.458 (s, 3H), 3.26 (s, 3H), 2.31-2.54 (m, 2H), 2.27 (s, 3H), 2.09-2.21 (m, 2H), 1.70 (t, J=7.6 Hz, 3H), 1.61 (t, J=7.6, 3H), 1.01 (d, J=7.0 Hz, 3H), −1.46 (br s, 1H). FIRMS (ESI) for $C_{70}H_{70}N_8O_8$ [MH$^+$] calculated: 1151.53894; found: 1151.54308. UV-Vis (MeOH, $\lambda_{max}$, nm): 255, 335, 410, 510, 545 610, 665.

Synthesis of conjugate 34: To a solution of compound 7 (50 mg, 0.0484 mmol) and 3-Ido benzyl amine 21 (16.90 mg, 0.0725 mmol) in 12 mL of dry dichloromethane, 1-ethyl-3-(3-dimethylaminopropyl)-carbodiimide hydro chloride (EDCI, 18.53 mg, 0.0967 mmol) and 4-(dimethylamino(pyridine (DMAP, 11.81 mg, 0.0967 mmol) were added. The reaction mixture was stirred at room temperature under N$_2$ atmosphere for overnight. It was then diluted with dichloromethane (40 mL), washed with water (3×50 mL), dried over anhydrous sodium sulfate and concentrated down to yield crude product which was purified by Silica column by using 6% methanol in dichloromethane to obtain pure product 34 with 76% (45.90 mg) yield. $^1$H NMR (400 MHz, CDCl$_3$, δ ppm): 9.79/9.64 (1H, s, 5-H), 9.34 (1H, s), 8.55/8.53 (1H, s), 8.46/8.34 (1H, s), 7.71/7.67 (1H, m), 7.57/7.51 (1H, m), 7.45 (1H, m), 7.37-7.42 (2H, m), 7.34-7.37 (1H, m), 7.28-7.34 (3H, m), 7.21/7.18 (1H, s), 7.14/7.13 (1H, m), ~7.1-7.2 (1H, br s), 7.08/7.06 (1H, s), 6.85 (1H, m), 6.79/6.77 (1H, dd, J=7.8, 7.8 Hz), 6.00/5.97 (1H, q, J=6.7 Hz), 5.72/5.66 (1H, t, J=5.6 Hz), 5.20/5.19 (1H, d, J=19.7 Hz), 5.05 (1H, d, J=19.7 Hz), 4.76/4.75 (1H, d, J=11.9 Hz), 4.63/4.61 (1H, d, J=11.9 Hz), 4.49/4.47 (1H, dq, J=7.2, 1.8 Hz), 4.34 (1H, m), 4.22-4.32 (2H, m), 4.14 (2H, m), 4.07-4.13 (1H, m), 3.950/3.946 (1H, dd, J=5.6, 15.0 Hz), 3.87 (2H, m), 3.69-3.76 (2H, m), 3.55/3.54 (2H, q, J=7.6 Hz), 3.49 (3H, s), 3.44/3.43 (3H, s), 3.41/3.39 (3H, s), 3.40/3.35 (3H, s), 3.18/3.17 (3H, s), 2.68 (1H, m), 2.50 (1H, m), 2.24 (1H, m), 2.15/2.13 (3H, d, J=6.7 Hz), 1.88 (1H, ddd, J=5.1, 10.0, 14.6 Hz), 1.79/1.77 (3H, d, J=7.1 Hz), 1.59/1.58 (3H, t, J=7.6 Hz), 0.43 (1H, br s), −1.70/−1.72 (1H, s). UV-vis (CH$_3$OH, $\lambda_{max}$, nm (abs)): 664 (0.253), 609

(0.045), 537 (0.049), 506 (0.052), 409 (0.050), 349 (0.273). MS (ESI) m/z: 1249.43 (M+H+). HRMS (ESI): calcd for $C_{69}H_{70}O_7N_8$ I (M+H$^+$) 1249.4383; found, 1249.4371.

Synthesis of conjugate 39: To a solution of compound 38 (50 mg, 0.0661 mmol) and compound 37 (48.64 mg, 0.0976 mmol) in 12 mL of dry dichloromethane, 1-ethyl-3-(3-dimethylaminopropyl)-carbodiimide hydro chloride (EDCI, 25.30 mg, 0.132 mmol) and 4-(dimethylamino(pyridine (DMAP, 16.13 mg, 0.132 mmol) were added. The reaction mixture was stirred at room temperature under $N_2$ atmosphere for overnight. It was then diluted with dichloromethane (40 mL), washed with water (3×50 mL), dried over anhydrous sodium sulfate and concentrated down to yield crude product which was purified by Silica column by using 6% methanol in dichloromethane to obtain pure product 39 with 71% (57.68 mg) yield. $^1$H NMR (400 MHz, CDCl$_3$, δ ppm): 9.76/9.73 (1H, s), 9.00/8.98 (1H s), 8.87/8.86 (1H, s), 8.68 (1H, s), 8.53 (1H, s), 8.20 (1H, d, J=8.2 Hz), 7.823/7.818 (1H, s), 7.79/7.76 (1H, m), 7.61-7.66 (2H, m), 7.41 (1H, s), 7.27-7.34 (3H, m), 7.22 (1H, s), ~7.21 (1H, d, J=8 Hz), ~7.10 (1H, br s), 7.07/7.05 (1H, t, J=7.7 Hz), 7.01 (1H, t, J=7.6 Hz), 6.91 (1H, d, J=7.7 Hz), 5.98/5.97 (1H, q, J=6.7 Hz), 5.08 (1H, d, J=19.8 Hz), 4.72/4.69 (1H, d, J=12 Hz), 4.57/4.56 (1H, d, J=12 Hz), 4.56 (1H, d, J=19.9 Hz), 4.51 (1H, dq, J=7.3, 1.4 Hz), 4.38 (1H, dd, J=6.6, 14.9 Hz), 4.28 (1H), 4.15-4.27 (4H, m), 4.00 (1H, dd, J=4.5, 14.7 Hz), 3.81 (2H, m), 3.63 (2H, m), 3.59 (2H, m), 3.44 (3H, s), 3.37/3.35 (3H, s), 3.239/3.238 (3H, s), 3.23/3.22 (3H, s), 2.81 (1H, m), 2.65 (1H, m), 2.34/2.32 (3H, s), ~2.31 (1H, m), 2.19/2.18 (3H, d, J=6.7 Hz), 2.03 (1H, m), 1.75 (3H, d, J=7.3 Hz), 1.63/1.62 (3H, t, J=7.6 Hz), 0.56 (1H, br s), −1.52 (1H, s). UV-vis (CH$_3$OH, $\lambda_{max}$, nm (abs)): 663 (0.456), 606 (0.084), 538 (0.086), 506 (0.087), 410 (0.829), 346 (0.499). MS (ESI) m/z: 1249.43 (M+H+). HRMS (ESI): calcd for $C_{69}H_{70}O_7N_8$ I (M+H$^+$) 1249.4376; found, 1249.4383.

Synthesis of conjugate 35: To a solution of compound 34 (30 mg, 0.025 mmol), hexamethylditin (295.09 mg, 1.88 mmol) and PdCl$_2$ (PPh$_3$)$_2$ (8.43 mg, 0.0120 mmol) in 12 mL of dry THF. The reaction mixture was stirred at room temperature under $N_2$ atmosphere for overnight. It was then diluted with dichloromethane (40 mL), washed with water (3×50 mL), dried over anhydrous sodium sulfate and concentrated down to yield crude product which was purified by Silica column by using 4% methanol in dichloromethane to obtain pure product 35 with 92% (28.42 mg) yield. $^1$H NMR (400 MHz, CDCl$_3$, δ ppm): 9.77/9.68 (1H, s), 9.37/9.36 (1H, s), 8.55/8.53 (1H, s), 8.55/8.48 (1H, s), 7.72 (1H, m), 7.65/7.61 (1H, m), 7.42-7.46 (2H, m), 7.27-7.36 (4H, m), 7.20-7.25 (2H, m), 7.12-7.17 (3H, m), 7.08/7.05 (1H, t, J=7.4 Hz), 6.89/6.85 (1H, dt, J=7.7, ~1.4 Hz), 6.00/5.97 (1H, q, J=6.7 Hz), 5.62/5.58 (1H, t, J=5.6 Hz), 5.214/5.205 (1H, d, J=19.8 Hz), 5.06 (1H, d, J=19.8 Hz), 4.75 (1H, d, J=11.8 Hz), 4.611/4.605 (1H, d, J=11.8 Hz), 4.50/4.48 (1H, dq, J=7.0, 1.8 Hz), 4.34 (1H, m), 4.28 (2H, m), 4.23/4.22 (1H, dd, J=5.6, 14.5 Hz), 4.15 (2H, m), 4.11 (1H, m), 3.86 (2H, m), 3.73 (2H, m), 3.57 (2H, q, J=7.6 Hz), 3.48 (3H, s), 3.47/3.46 (3H, s), 3.41/3.40 (3H, s), 3.39/3.35 (3H, s), 3.19/3.18 (3H, s), 2.70 (1H, m), 2.48 (1H, m), 2.27 (1H, m), 2.15/2.13 (3H, d, J=6.7 Hz), 1.92 (1H, m), 1.79/1.77 (3H, d, J=7.0 Hz), 1.61/1.60 (3H, t, J=7.6 Hz), 0.40 (1H, br s), 0.144/0.137 (9H, s), −1.70/-1.72 (1H, s). UV-vis (CH$_3$OH, $\lambda_{max}$, nm (abs)): 664 (0.663), 609 (0.120), 538 (0.136), 506 (0.131), 409 (1.315), 349 (0.719). MS (ESI) m/z: 1287.50 (M+H$^+$). HRMS (ESI): calcd for $C_{69}H_{70}O_7N_8$ I (M+H$^+$) 1287.5000; found, 1287.5010.

Synthesis of conjugate 40: To a solution of compound 39 (30 mg, 0.025 mmol), hexamethylditin (295.09 mg, 1.88 mmol) and PdCl$_2$ (PPh$_3$)$_2$ (8.43 mg, 0.0120 mmol) in 12 mL of dry THF. The reaction mixture was stirred at room temperature under $N_2$ atmosphere for overnight. It was then diluted with dichloromethane (40 mL), washed with water (3×50 mL), dried over anhydrous sodium sulfate and concentrated down to yield crude product which was purified by Silica column by using 4% methanol in dichloromethane to obtain pure product 40 with 86% (26.57 mg) yield. $^1$H NMR (400 MHz, CDCl$_3$, δ ppm): 9.77/9.74 (1H, s), 9.10/9.07 (1H, s), 8.75 (1H, br s), 8.69 (1H, s), 8.52 (1H, s), 8.21 (1H, d, J=8.3 Hz), 7.79 (1H, s), 7.65 (1H, m), 7.41-7.49 (3H, m), 7.30-7.41 (4H, m), 7.24 (1H, s), 7.22 (1H, br d, J=8 Hz), 7.06/7.04 (1H, dd, J=1.6, 7.6 Hz), 6.93 (1H, br d, J=7.4 Hz), 6.81 (1H, br s), 6.02/5.99 (1H, q, J=6.8 Hz), 5.13 (1H, d, J=19.8 Hz), 4.81/4.79 (1H, d, J=11.6 Hz), 4.65/4.64 (1H, d, J=19.8 Hz), 4.64/4.62 (1H, d, J=11.5 Hz), 4.53 (1H, q, J=7.2 Hz), 4.41/4.40 (1H, dd, J=6.4, 14.8 Hz), 4.31 (1H, m), 4.27 (2H, m), 4.23 (2H, m), 4.04 (1H, dd, J=4.2, 14.7 Hz), 3.83 (2H, m), 3.63 (2H, m), ~3.61 (2H, m), 3.45 (3H, s), 3.37/3.34 (3H, s), 3.234/3.230 (3H, s), 3.19/3.18 (3H, s), 2.83 (1H, m), 2.65 (1H, m), 2.49 (3H, br s), 2.32 (1H, m), 2.162/2.156 (3H, d, J=6.7 Hz), 2.02 (1H, m), 1.76 (3H, d, J=7.2 Hz), 1.65/1.63 (3H, t, J=7.6 Hz), 0.62 (1H, br s), 0.22/0.20 (9H, s), −1.49 (1H, s). UV-vis (CH$_3$OH, $\lambda_{max}$, nm (abs)): 663 (0.622), 607 (0.119), 539 (0.122), 506 (0.119), 410 (1.314), 347 (0.664). MS (ESI) m/z: 1287.50 (M+H$^+$). FIRMS (ESI): calcd for $C_{69}H_{70}O_7N_8$ I (M+H$^+$) 1287.1876; found, 1249.1883.

Synthesis of conjugate 43: To a solution of compound 42 (30 mg, 0.045 mmol), compound D (17.60 mg, 0.045 mmol) and BOP (29.86 mg, 0.068 mmol) in 10 mL of dry DMF add 2 drops of triethylamine. The reaction mixture was stirred at room temperature under N2 atmosphere for overnight. After completion of the reaction the reaction mixture was diluted with dichloromethane 30 mL), washed with water (3×30 mL), dried over anhydrous sodium sulfate and concentrated down to yield crude product which was purified by Silica column by using 8% methanol in dichloromethane to obtain pure product 43 with 63% (29.28mg) yield. $^1$H NMR (400 MHz, CDCl$_3$, δ ppm): 9.63/9.61 (1H, s), 9.33 (1H, s), 8.42/8.41 (1H, s), 8.38/8.38 (1H, s), 7.73 (1H, s), 7.63/7.61 (1H, s), 7.57 (t, 1H, J=8.4 Hz), 7.33/7.31 (1H, d, J=8.0 Hz), 7.27 (1H, s), 7.21/7.10 (1H, m), 7.01/7.00 (1H, m), 5.70/5.4 (1H, q, J=6.8 Hz), 5.17/5.12 (1H, d, J=20.4 Hz), 4.96/4.91 (1H, d, J=20.0 Hz), 4.39/4.31 (1H, d, J=6.0 Hz), 4.12/4.09 (1H, d, J=8.0 Hz), 3.84 (3H, m), 3.54 (5H, m), 3.48 (5H, s), 3.27 (2H, m), 3.25 (3H, s), 3.14 (3H, s), 3.07 (3H, s), 2.53 (2H, m), 2.24 (2H, m), 2.00 (5H, m), 1.71/1.50 (8H, m), 1.46 (2H, m), 1.27 (4H, m), 1.11 (3H, s), 0.78 (1H, brs), 0.67 (3H, s), −0.01 (1H, s). UV-vis (CH$_3$OH, $\lambda_{max}$, nm (abs)): 661 (0.352), 605 (0.069), 537 (0.072), 507 (0.071), 408 (0.691). MS (ESI) m/z: 1052.33 (M+H$^+$). HRMS (ESI): calcd for $C_{63}H_{74}N_9O_6$ (M+H$^+$) 1052.3354; found, 1052.3362.

Synthesis of conjugate 44: To a solution of compound 42 (30 mg, 0.045 mmol), compound F (22.34 mg, 0.045 mmol) and BOP (29.86 mg, 0.068 mmol) in 10 mL of dry DMF add 2 drops of triethylamine. The reaction mixture was stirred at room temperature under $N_2$ atmosphere for overnight. After completion of the reaction the reaction mixture was diluted with dichloromethane (30 mL), washed with water (3×30 mL), dried over anhydrous sodium sulfate and concentrated down to yield crude product which was purified by Silica column by using 8% methanol in dichloromethane to obtain pure product 44 with 66% (34.42 mg) yield. $^1$NMR (400 MHz, CDCl$_3$, δ ppm): 9.59/9.58 (1H, s), 9.32/9.38 (1H, s), 8.38 (1H, s), 8.35/8.36 (1H, s), 7.71 (1H, brs), 7.57 (1H, t, J=8.4 Hz), 7.33/7.31 (1H, d, J=8.0 Hz), 7.27 (1H, s), 7.21/7.10 (1H, m), 6.90 (1H, t, J=6.80 Hz), 5.79/5.73 (1H, q, J=6.8 Hz), 5.17/5.12 (1H, d, J=20.4 Hz), 4.96/4.91 (1H, d, J=20.0 Hz), 4.39/4.31 (1H, d, J=6.0 Hz), 4.12/4.09 (1H, d, J=8.0 Hz), 3.96/3.80 (12H, m), 3.58/3.47 (4H, m), 3.44 (3H, s), 3.23 (3H, s), 3.11/3.10 (s, 3H), 3.07/3.06 (3H, s), 2.52 (1H, m), 2.47 (1H, s), 2.30 (1H, m), 2.20/2.05 (3H, m), 2.02 (3H, m), 1.98/1.96 (3H, d, J=7.2 Hz), 1.70/1.42 (15H, m), 1.31 (2H, m), 1.12/1.03 (5H, m), 1.10 (5H, m), 0.62 (3H, t, J=7.6 Hz). UV-vis (CH$_3$OH, $\lambda_{max}$, nm (abs)): 662 (0.175), 605 (0.035), 538 (0.036), 507 (0.036), 409 (0.339), 350 (0.180). MS (ESI) m/z: 1166.64 (M+H$^+$). HRMS (ESI): calcd for C$_{69}$H$_{84}$N$_9$O$_8$ (M+H$^+$) 1166.6452; found, 1166.6459.

Biological Studies (a) Bladder Cancer

Comparative in vitro PDT efficacy of 20, 30 and the PS-erlotinib conjugates 6, 34, 39 in bladder cancer cell lines: To compare cytotoxic potential of each compound, an MTT assay was conducted [UMUC3 and T24 cells were plated in 96 well plates at 1×10$^4$ cells per well. Photosensitizers were incubated for 24 hours with the cells before being irradiated at peak absorbance (around 665 nm) for a total of 1, 2, or 4 Joules. 24 hours after light exposure, the plates were read for viability. In general, all photosensitizers showed higher PDT efficacy in UMUC3 than T24 cell lines. However, in both cell lines PS 34 in which erlotinib was introduced at the top half of the molecule was less effective than 39, where it is conjugated at the lower half.

Figure 7:
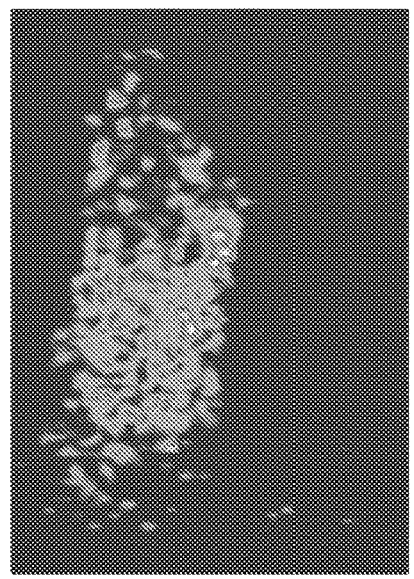
FIG. 7 shows PET image of SCID mouse bearing UMUC3 tumor with PS 30 (I=-$^{124}$I), Dose: 30 µCi.

C1d. Conjugation of PS with erlotinib does not make any significant difference in site(s) of localization: To investigate the impact of structural modifications in intracellular localization ability of PS. Subcellular localization was conducted utilizing an ImageStream flow cytometry. Mitotacker red and FluoSphaeres carboxylate to stain the mitochondria and the lysosome respectively. The results summarized in FIG. 7 shows a significant degree of difference in site(s) of localization by PS in UMUC3 and T24 cells.

Figure 3:
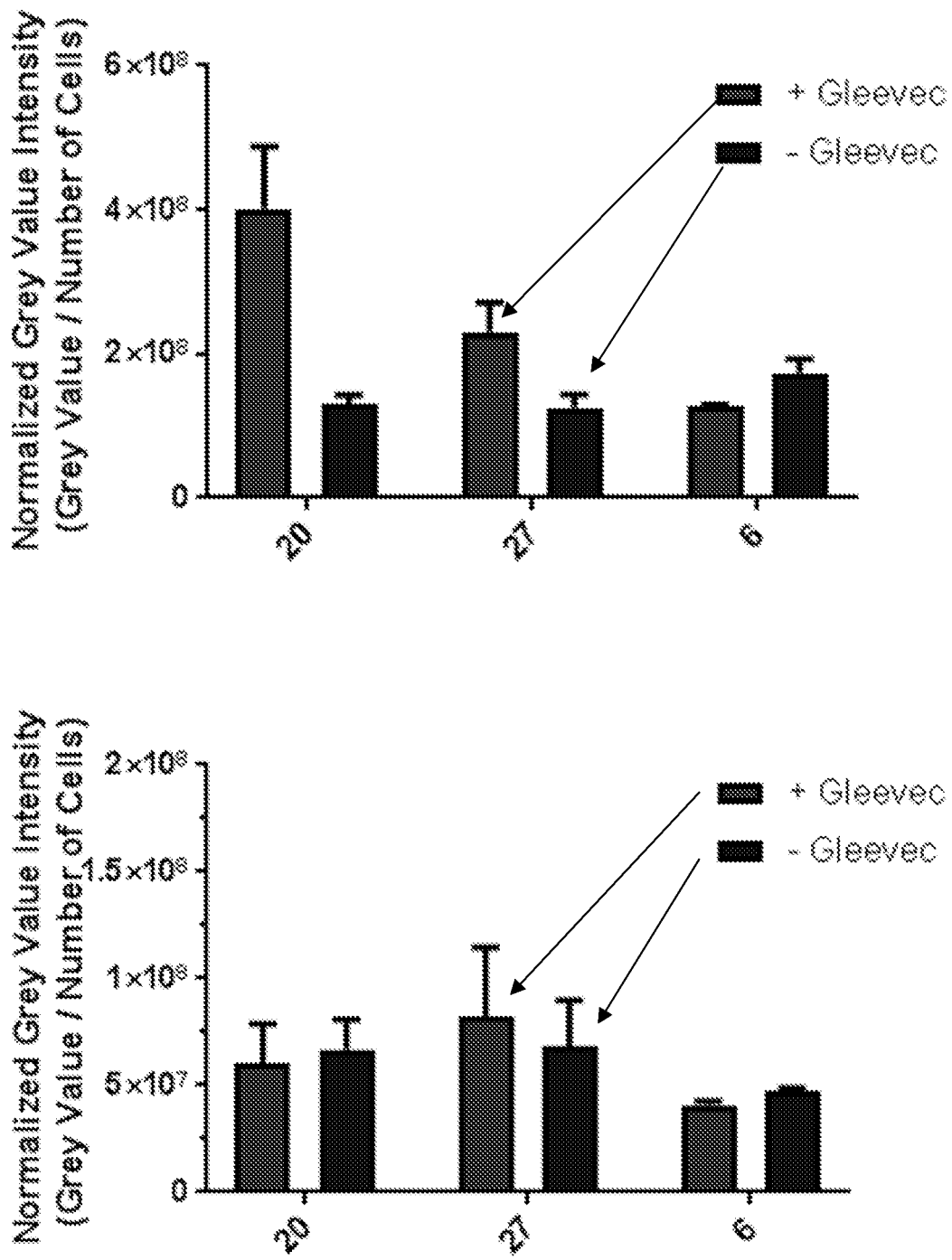
FIG. 3 shows ABCG2 substrate specificity of PSs with and without erlotinib in UMUC3 and T24 cells. T24 cells lack ABCG2 expression.
Figure 4:
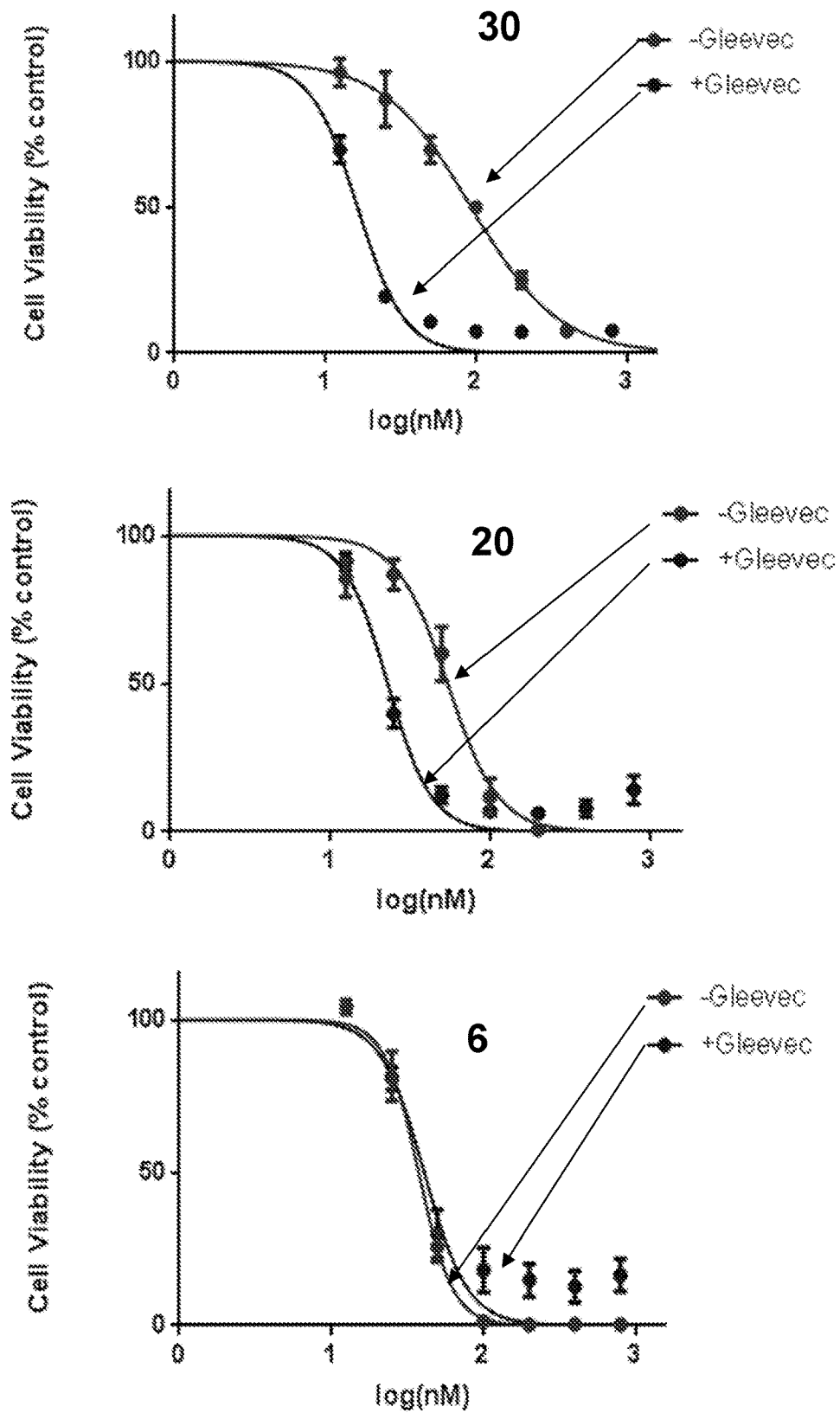
FIG. 4 shows PS 30 (HPPH), 20 are the substrates of ABCG2 and show an enhancement of PDT efficacy in presence of Gleevec (1>2), whereas PS 6 (PS-erlotinib conjugate), which is not a substrate of ABCG2 does not show any impact of Gleevac in PDT efficacy (determined by MTT assay).

C1e. In contrast to PS 1 and 2, the PS- erlotinib conjugate 3 is not the substrate of ABCG2: The influence of PS as substrate for ABCG2 transport was observed by fluorescent microscopy. Cells were co-incubated with or without Gleevec (5 µM) with the photosensitizers 30, 20 and the erlotinib conjugate 6 (500 nM) and their relative uptake was measured. Interestingly in UMUC3 cells, the addition of Gleevec significantly increased its uptake of PS 30 & 20 but no significant difference was observed with the conjugate 3. Conversely, in T24 cells, the addition of Gleevec did not show any significant increase in the uptake of PS 30, 20 and 6 (determined by fluorescence) could be due to a lack of ABCG2 pump (FIG. 3). This information is very interesting as it could help to select an effective treatment option to cancer patients with and without expression of ABCG2 transporter. Interestingly, the comparative in vitro PDT evaluation of PS 30 (HPPH), 20 and 6 (PS-erlotinib conjugate) in UMUC3 cells with and without Gleevac also confirmed that unlike PS 20 and 30, erlotinib conjugate 6 is not the substrates for ABCG2 (no difference in PDT efficacy with and without Gleevec), FIG. 4.

Figure 5:
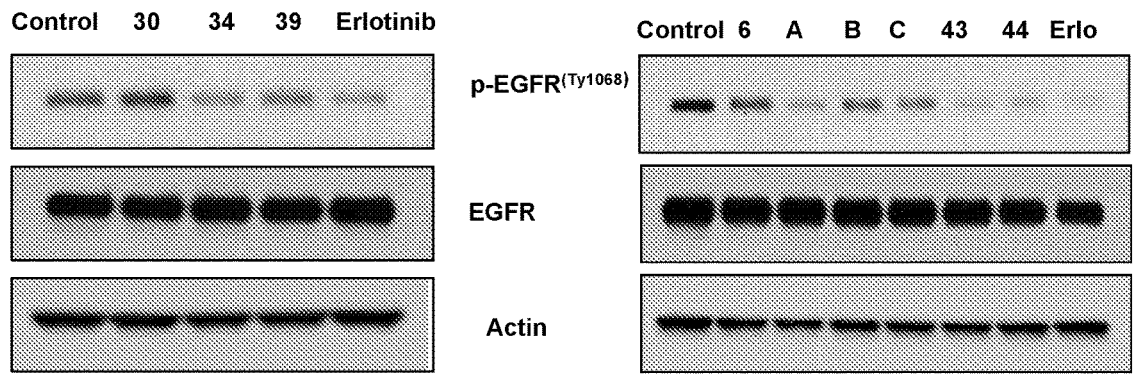
FIG. 5 shows comparative EGFR signal inhibition efficacy of erlotinib, modified erlotinib (A, B, C and PS-erlotinib 30, 34, 39 and PS-modified erlotinib conjugates 43 & 44).
Figure 5:
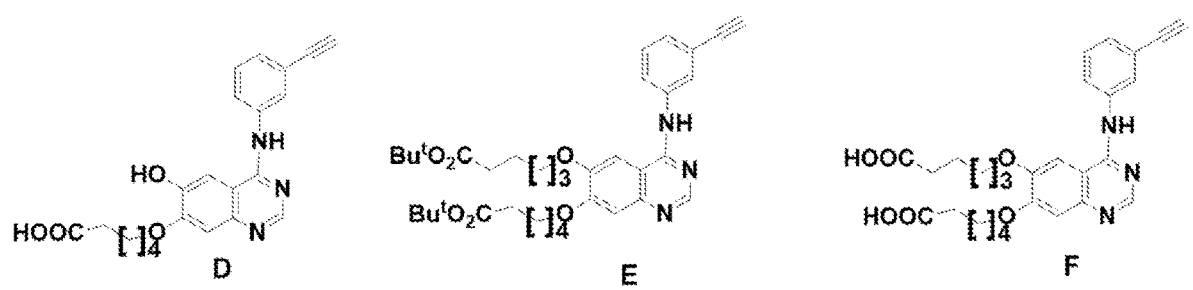
Figure 5:
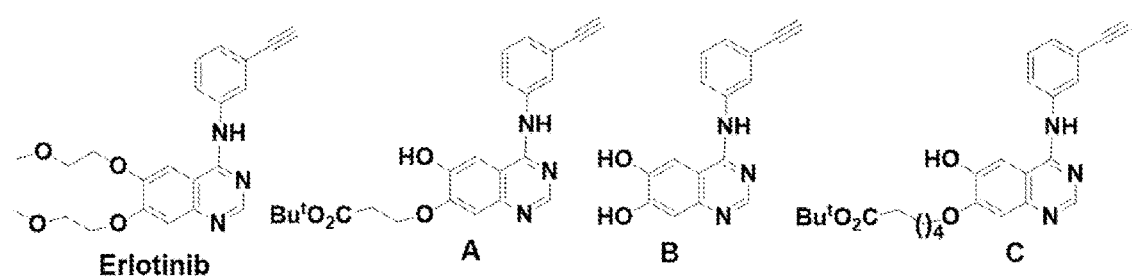
Figure 5:
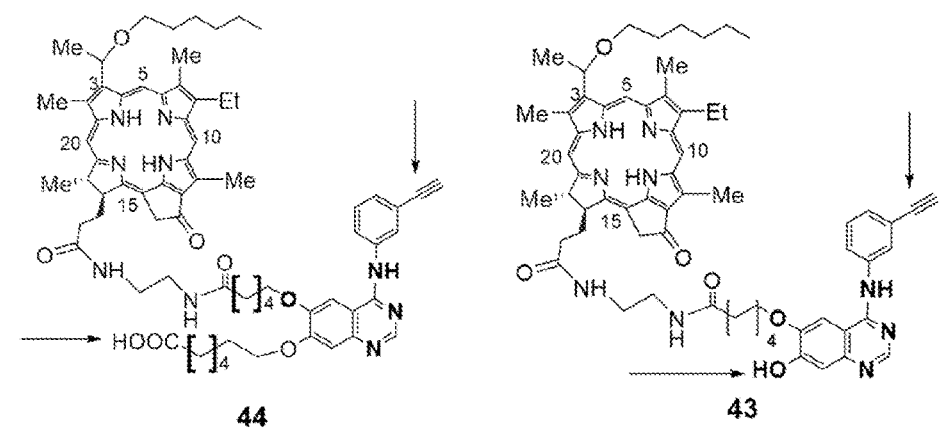

C1f. Among PS-erlotinib analogs, the presence of peripheral substituents in PS and the position of conjugation with erlotinib (or modified erlotinib) makes a difference in EGFR target-specificity. To show that the PS-erlotinib analogs are effective against activation of EGFR, we treat EGFR dependent UMUC3 bladder cancer cells with these compounds for 30 hours and analyze the levels of p-EGFR in whole cell lysate through western blotting using phospho specific antibody. Our results showed that except compound 30 and 6 all other PS-erlotinib analogs are able to inhibit the autophosphorylation of EGFR at Ty1068 residue (FIG. 5) albeit with different efficacy. It's worth mentioning here that some compounds namely 34, 39, A, 43 and 44 are equally effective in inhibiting EGFR activation as erlotinib. We do not see much change in total EGFR levels, which indicate that the decrease in phospho EGFR levels is not due to downregulation in protein level per se but the inhibition of autophosphorylation at its intercellular kinase domain of EGFR by these analogs.

Figure 6:
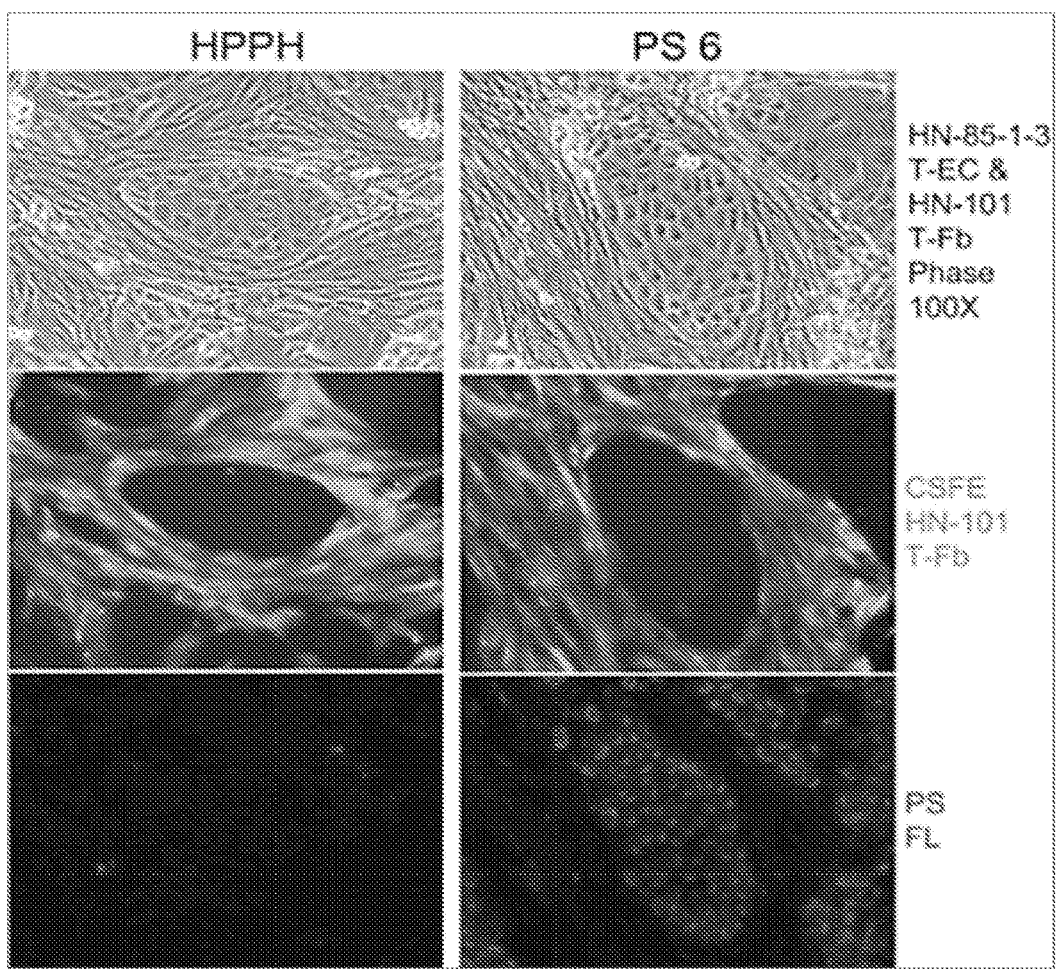
FIG. 6 shows co-culture of EGFR positive tumor and CSFE-stained tumor stromal cells were incubated for 24 h with 1600 nM HPPH 1 and erlotinib-PS conjugate 3 in RPMI+10% FBS. The cells were washed free of PS and incubated for additional 48 h in medium. The fluorescence for CSFE stromal cells and PS fluorescence was recorded in an inverted fluorescent microscope.

C1g PS-erlotinib conjugate enhances its specificity to EFGR positive tumor. It was shown that cell type specific retention of certain PS using a novel three dimensional (3D) co-culture system of primary tumor cells and associated stroma. This approach could be extremely helpful in developing a personalized choice of the PS for a particular type of cancer. Previous reports from have also shown a direct correlation between photo-induced STAT3 dimerization and PDT efficacy which allows us to use STAT3 dimerization as a biomarker for optimizing the treatment parameters For a proof-of-principle study, we initially investigated the utility of PSs: HPPH 1 and the erlotinib conjugate 6 in tumors with high expression of EGFR, and the results summarized in FIG. 6 show the remarkable selectivity of PS 6 over HPPH in EGFR positive tumor [59].

C1h. $^{124}$-PS 2a shows PET imaging ability of UMUC3 tumor (bladder): In contrast to $^{18}$F-FDG, the $^{124}$I-analog of pyropheophorbide-a 30 (30-I$^{124}$)) at a dose of 30 □Ci (not optimized) showed excellent ability to image UMUC3 tumors implanted in SCID mice at 24 h postinjection (FIG. 7). Due to a long half-life (4 days) of $^{124}$I-radionuclide, the $^{124}$I-labeled PS in a single dose can be used for monitoring the tumor response. In contrast to $^{18}$F-FDG (a current clinical standard, half-life 110 min), the $^{124}$I-analog can be shipped at long-distances. This compound is highly fluorescent (Abs: 665 nm, Em: 715 nm) and provide an opportunity for its use in fluorescence-guide PDT. Finally, compound 30 (1-124) in combination with the respective non-radioactive analog 30 provides a unique opportunity for imaging tumors by two different modalities (PET and fluorescence) with an option of PDT.

Figure 8:
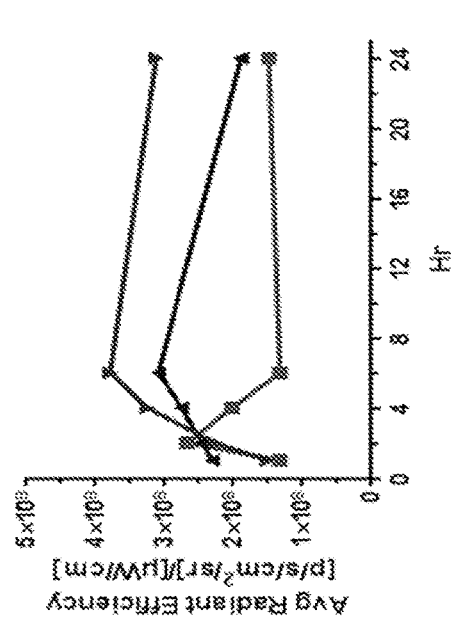
FIG. 8 shows Comparative uptake of PS 2, 3, 5 and 10 in tumor, liver and skin (SCID mice bearing UMUC3 and T24 tumors) at a dose of 0.47 µmol/kg)) at variable time points ($\lambda_{ex}$: 675 nm, $\lambda_{em}$: 720), using the IVIS system.
Figure 8:
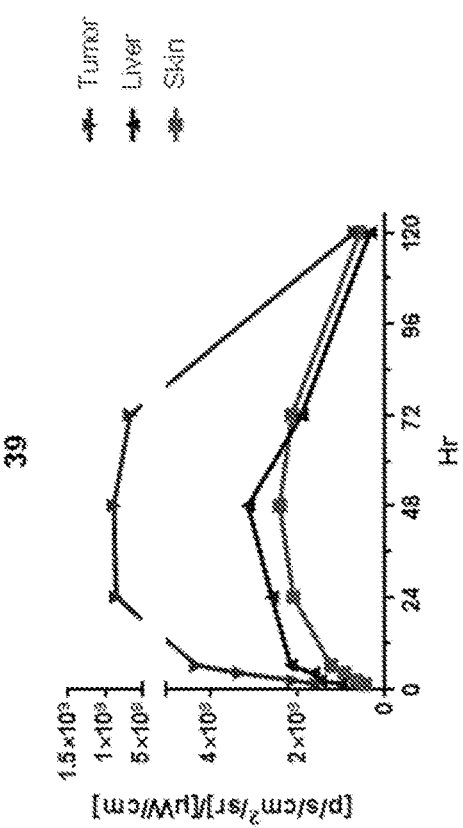
Figure 8:
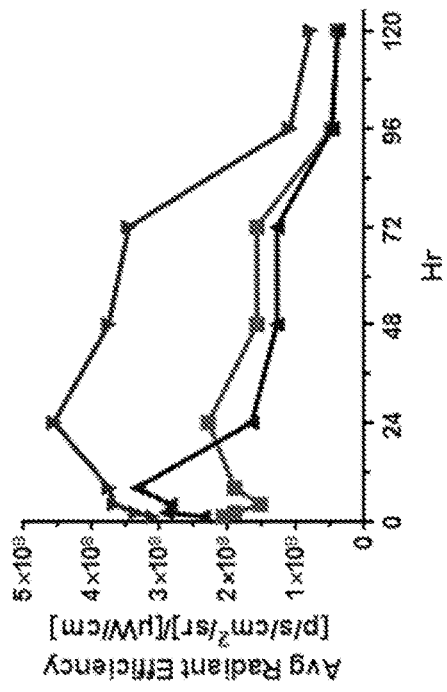
Figure 8:
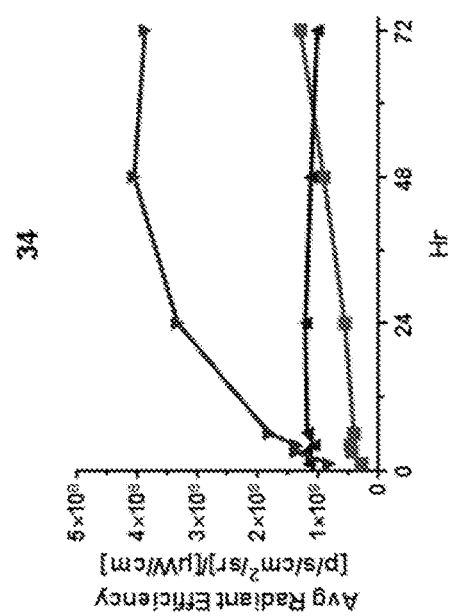
Figure 8:
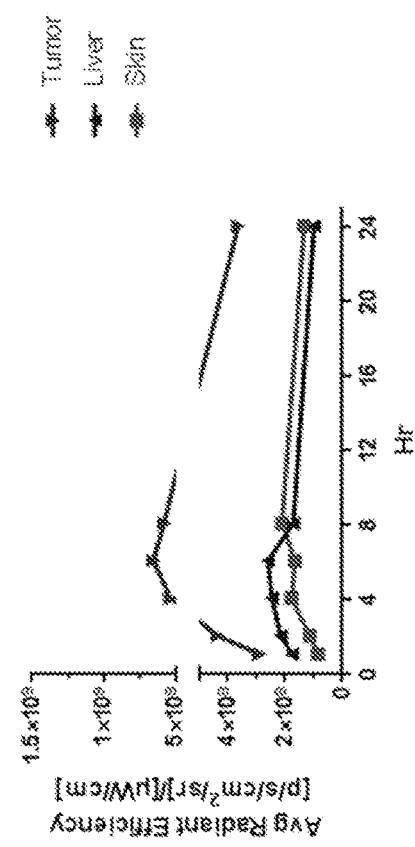
Figure 8:
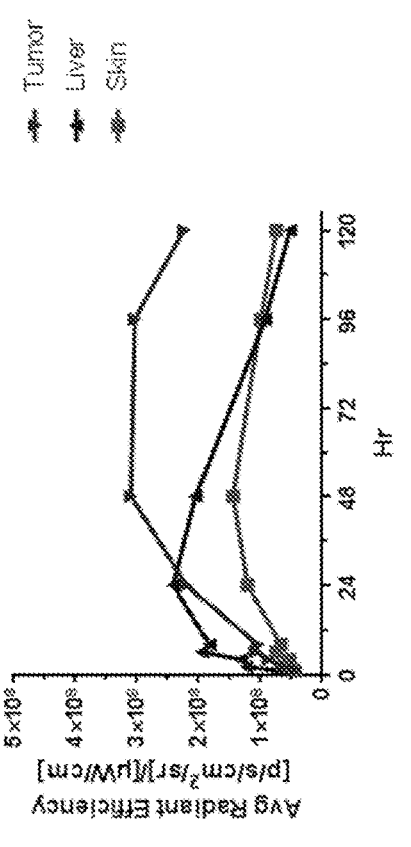
Figure 8:
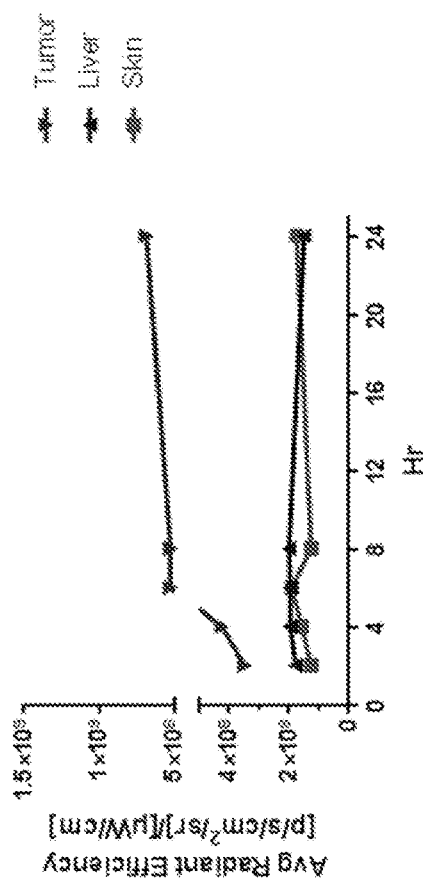
Figure 8:
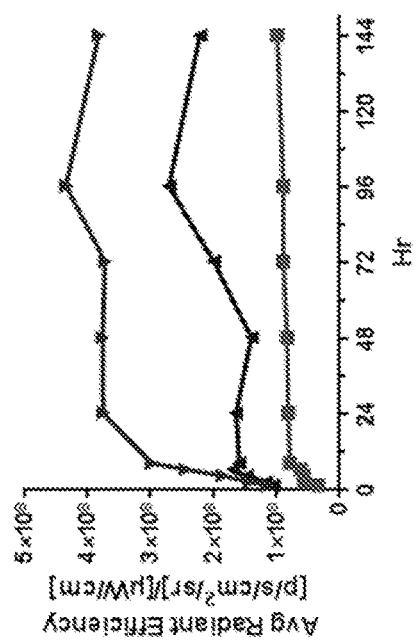

C1i. PS with and without erlotinib show high tumor-uptake and significant difference in their pharmacokinetic profiles in UMUC3 and T24 tumors implanted in SCID mice: The SCID mice bearing either UMUC3 or T24 tumors (4-5 mm size) were injected with the PS 30, and the corresponding erlotinib conjugates 6, 34 & 39 with and without iodine functionality. Among the iodinated analogs, the iodobenzyl group was introduced either at the bottom half of 5 or top half of the molecule 39, and were converted into the corresponding radioactive ($^{124}$I-) analogs for PET imaging. The non-radioactive analogs were injected in tumored mice (3 mice/group) at a dose of 0.47 µmol/kg), and the mice were imaged at regular time intervals. The dose was selected on the basis of the therapeutic dose of HPPH. The uptake of tumor, liver and skin was measured by IVIS system (3 mice group), and interesting pharmacokinetic profiles of the PS were observed (FIG. 8). For example PS 30, showed high uptake in UMUC3 tumor at 24 h post-inj, whereas in T24 it showed optimal uptake from 8-24 h with limited uptake in liver and skin. Conjugate 3 in both UMUC3 and T24 showed high uptake at 6 h postinjection, but it declined more rapidly in T24 tumors to UMUC3. PS 34 in both UMUC3 and T24 tumors retained for longer period, but the liver uptake was significantly higher in T24 tumors, Finally, PS 39 also showed tumor-avidity in both tumors, but the pharmacokinetic profiles were significantly different. All conjugate showed significantly lower uptake in skin, and should not produce any significant skin phototoxicity.

Figure 9:
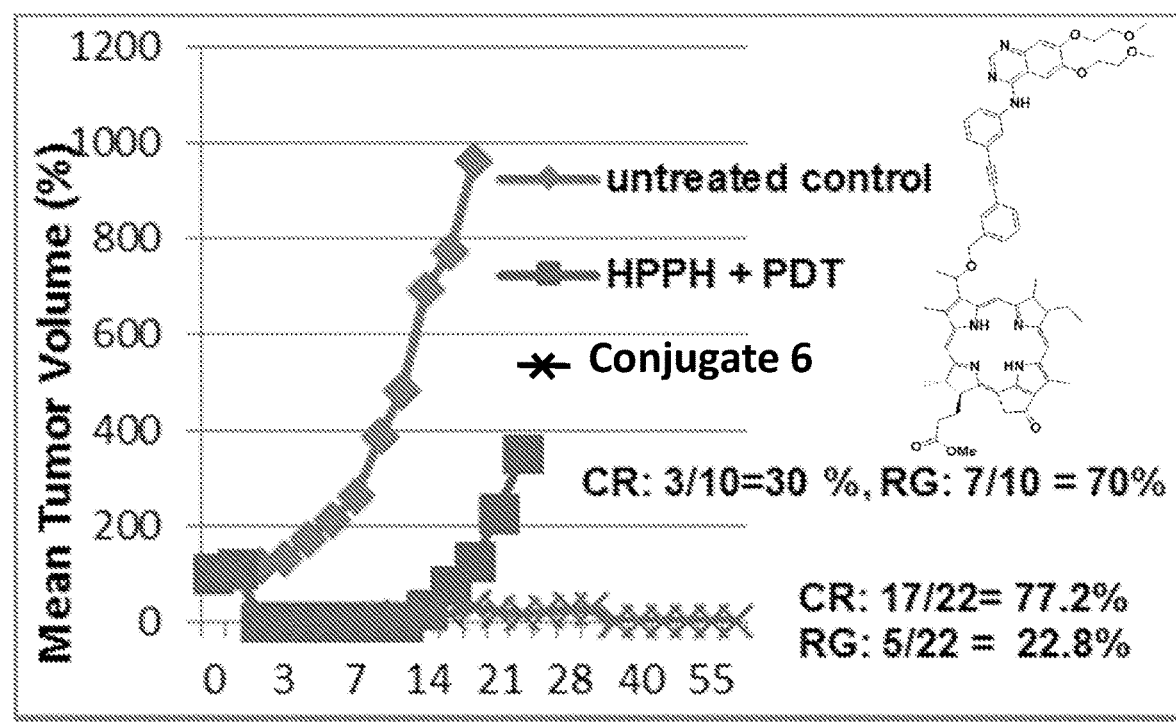
FIG. 9 shows long-term (60 day) in vivo PDT efficacy of HPPH and the PS-erlotinib conjugate 6 in SCID mice bearing UMUC3 tumors under the same treatment parameter (dose 0.47 µmol/kg, light dose: 135 J/cm$^2$, 75 mW/cm$^2$). CR: Complete Response (Cure), RG: Re-Growth of tumors.

C1j. Compared to HPPH, PS- erlotinib conjugate 6 shows enhanced PDT efficacy: For a proof of principle study, the PDT efficacy of HPPH and the conjugate 6 was compared UMUC3 implanted in SCID mice under same drug dose (0.47 µmol/kg) and light dose (135 J/cm², 75 mW/Cm²). In UMUC3 tumor model, compared to HPPH, which showed optimal uptake at 24 h, the HPPH-erlotinib gave maximum uptake at 8 h post-injection. Therefore, the tumors were exposed to light at their optimal uptake time points respectively. The tumors were monitored daily for 60 days, and from the results summarized in FIG. 9, it can be seen that compared to HPPH, the PS-erlotinib conjugate showed enhanced PDT efficacy.

Figure 10:
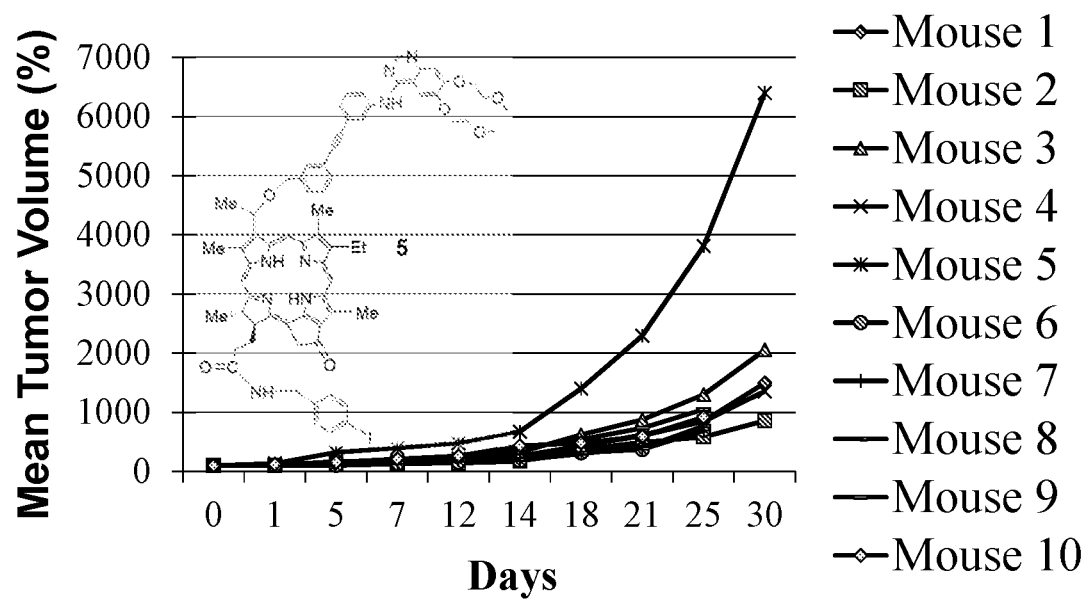
FIG. 10 shows comparative in vivo PDT efficacy of PS-erlotinib conjugates 34 and 39 in SCID mice bearing FaDu tumor xenografts (over express EGFR). Tumors were irradiated with light (665 nm, 135 J/cm$^2$, 75 mW/cm$^2$) at 24 h post-injection of the PS (0.47 µmol/kg).
Figure 10:
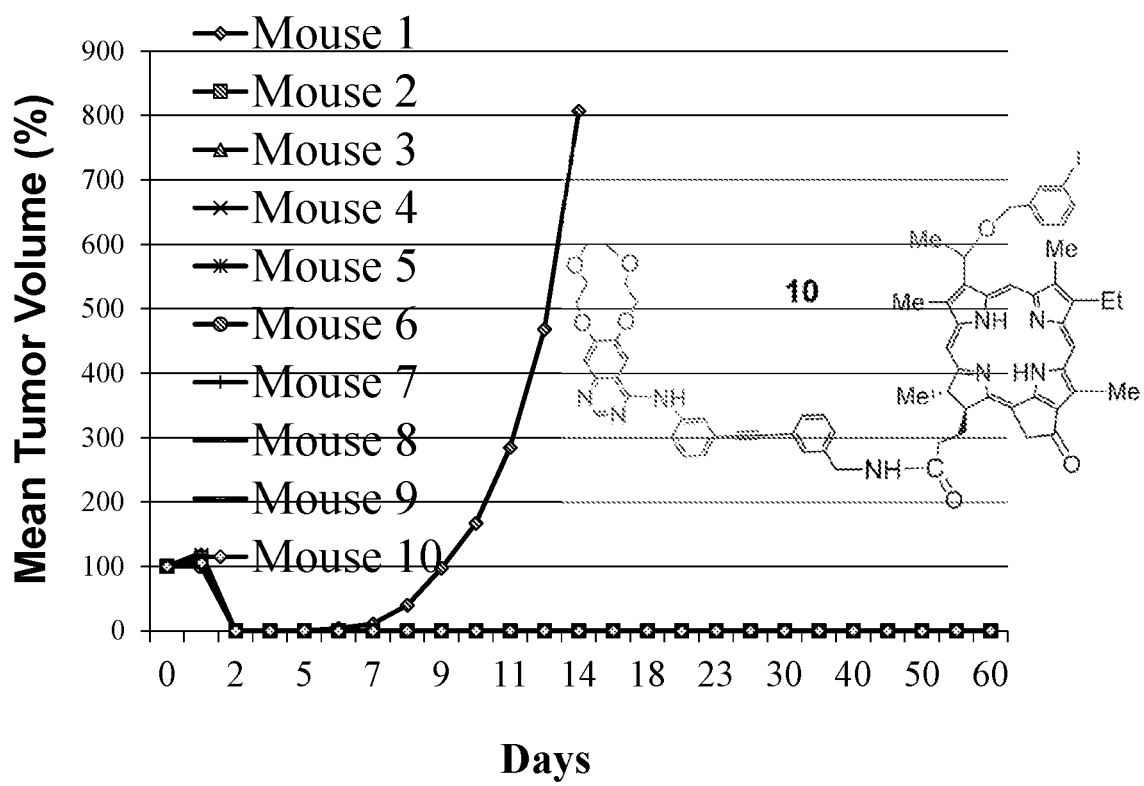

C1k. Position of erlotinib in the PS moiety shows similar uptake, but a significant difference in in vivo efficacy: To investigate a correlation between in vivo tumor-uptake and PDT efficacy of multifunctional agent (PET/fluorescence+ PDT) efficacy of compounds 34 and 39, these compounds were evaluated in SCID mice bearing FaDu tumors, (due to the availability of tumored mice) known for high expression of EGFR. Both compounds showed optimal and similar-uptake (determined by fluorescence) in tumor at 24 h tumors post injection (dose: 0.47 µmol/kg) Interestingly, compared to compound 34 the conjugate 39 showed significantly improved long-term (day 60) tumor cure (FIG. 10). This is possibly due to special arrangement between the erlotinib and PS moieties caused by the orientation of the molecules.

Figure 11:
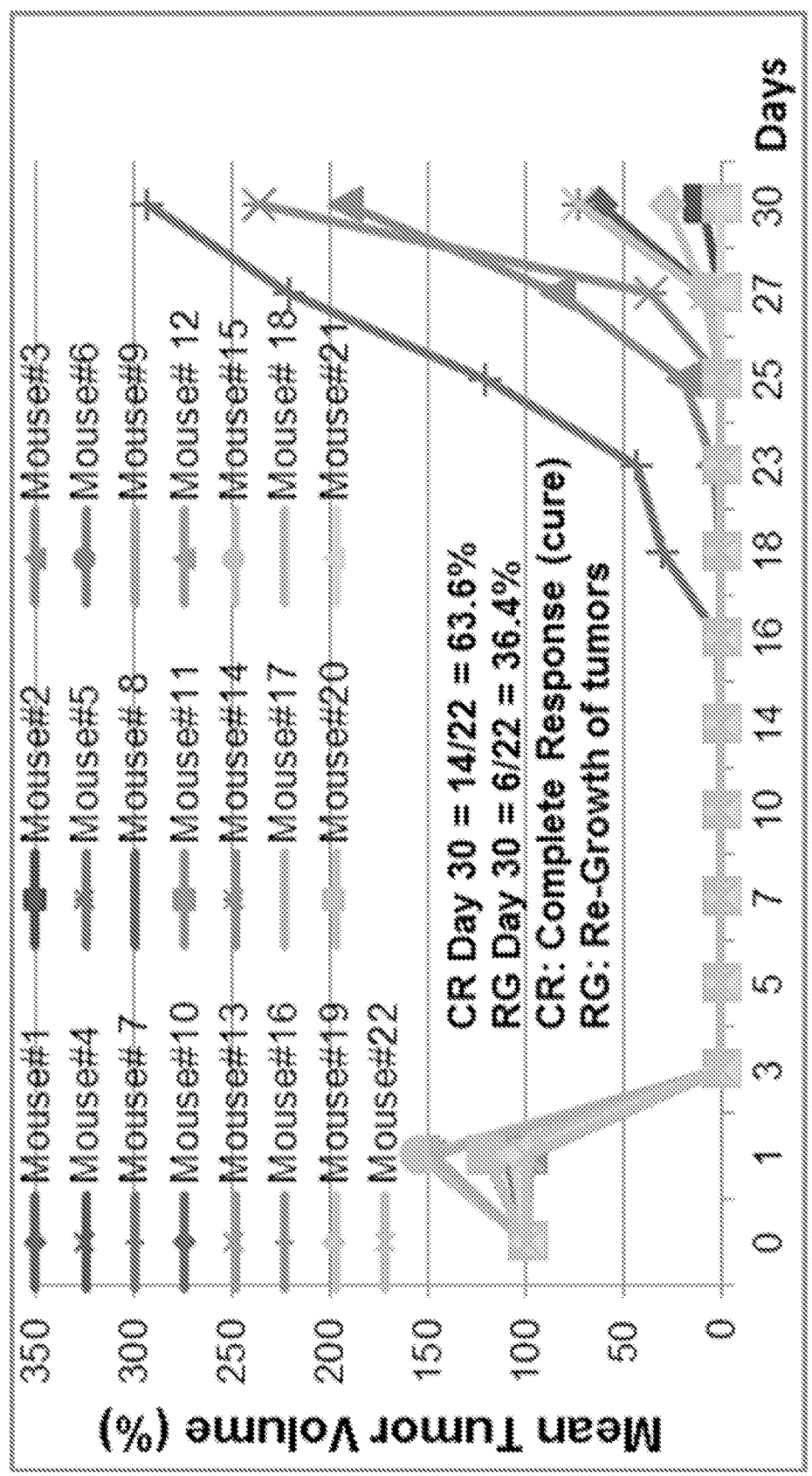
FIG. 11 shows combined data of several experiments (total mice: 22 bearing UMUC3 tumors). HPPH-PDT in combination with BCG (dose not optimized) showed improved long-term cure than HPPH-PDT alone. For details see the text.

C1j.Photosensitizer (e.g., HPPH) in combination with BCG shows enhanced PDT efficacy in bladder tumors (UMUC3) "A Proof of Principle Study": To investigate the utility of combination treatment approach for treating bladder cancer, mice bearing UMUC3 tumors were injected intravenously with HPPH (0.47 µmol/kg) and the tumors were exposed to a laser light (135 J/cm², 75 mW/cm²) at 6 h post-injection. One hour after the PDT treatment, BCG was injected (1-1.5×10⁶ CFU), SQ weekly×3 doses, and the day 30 data summarized in FIG. 11, are very encouraging.

The biological analysis of the HPPH-erlotinib compounds had to address the dual function of the molecules: (1) the interaction with target cells, including uptake, intracellular deposition, retention and photoreaction, and (2) inhibition of EGFR kinase activity leading to loss of autophosphorylation of the EGFR protein. Unconjugated erlotinib served as reference.

(b) Head and Neck Cancer

Figure 12:
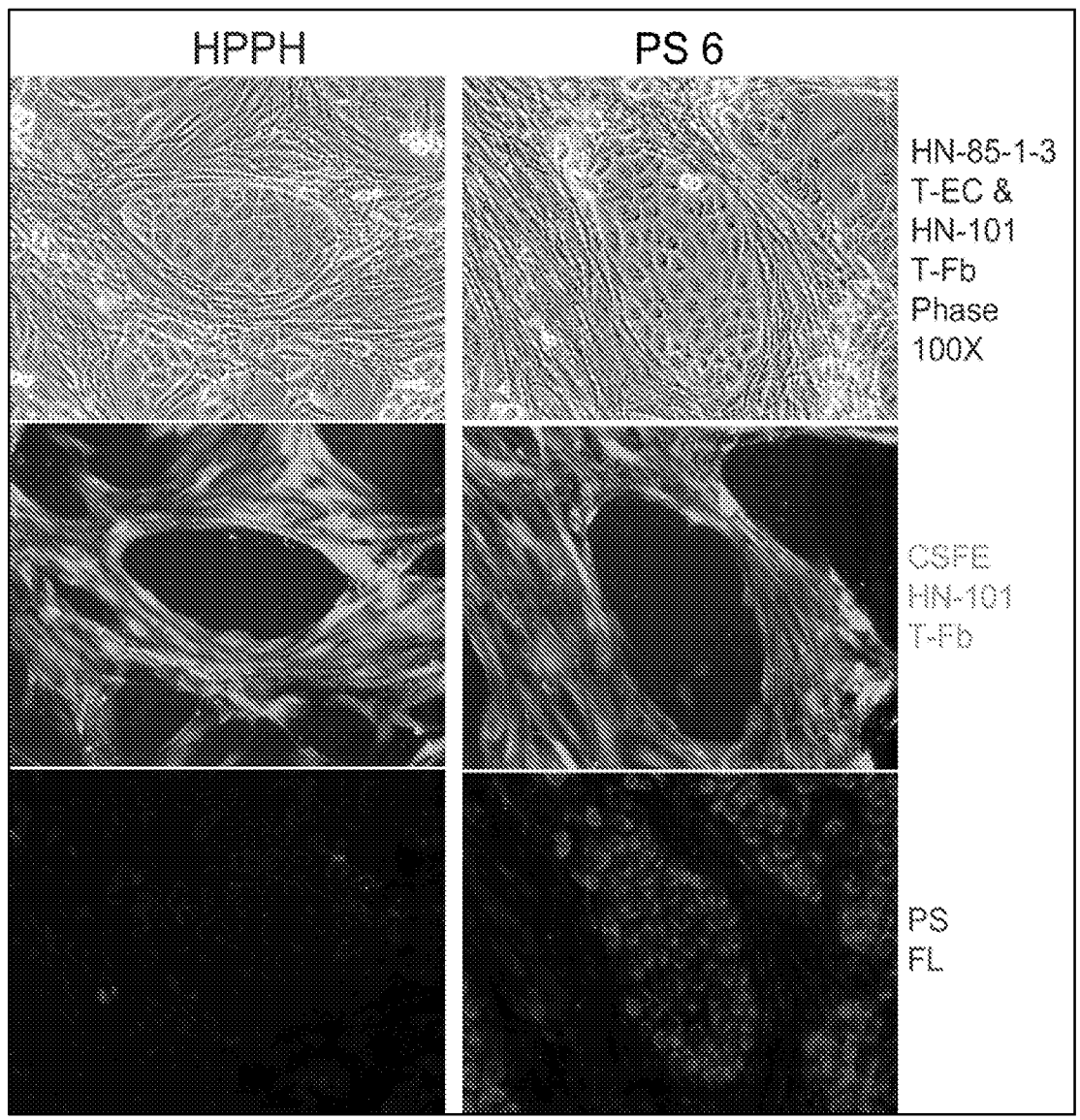
FIG. 12 shows co-culture of HN-85-1-3 and CSFE-stained tumor stromal cells were incubated for 24 h with 1600 nM HPPH or PS-6 in RPMI+10% FBS. The cells were washed free of PS and incubated for additional 48 h in medium. The fluorescence for CSFE stromal cells and PS fluorescence was recorded in an inverted fluorescent microscope.

The tumor specificity of the compounds was also confirmed in head & neck cancer using 3D culture system. For example, the specificity of PS 6, the specific retention by HNSCC cells could be confirmed in 3-D co-culture system by the prominent presence within the HNSCC cells, which have otherwise low retention of HPPH (FIG. 12).

Figure 13:
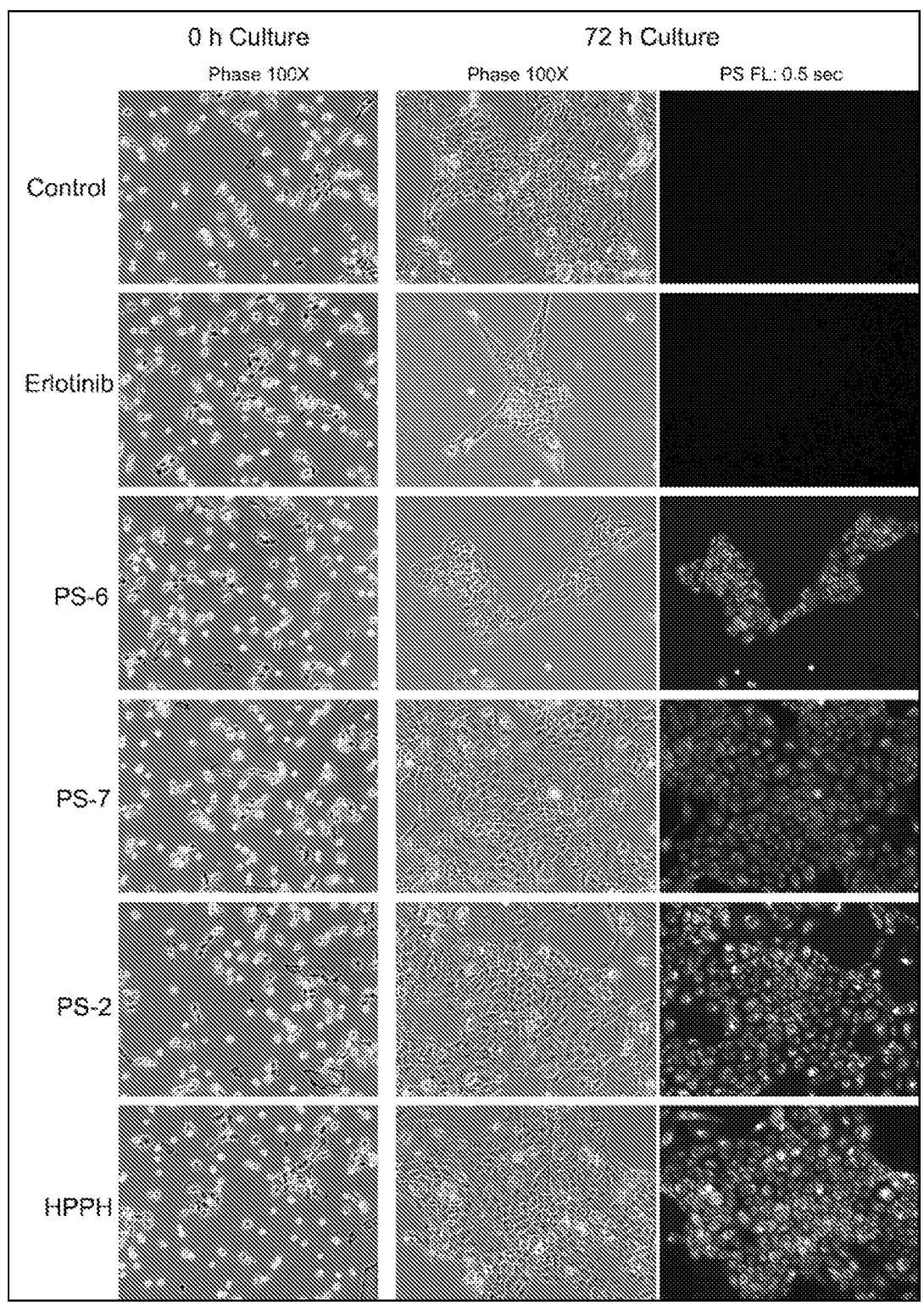
FIG. 13 shows growth inhibition by erlotinib and PS-6. HN-85-1-3 cells were cultured of 72 h in regular growth medium (RPMI+10% FBS) and containing 3.2 µM erlotinib or the indicated PSs. The cell density was photographically recorded at the beginning and end of the culture period. The cell-associated PSs were determined by fluorescence imaging.

Finally, preliminary experiments using EGF-dependent HNSCC cell cultures indicated that PS-6 (FIG. 13) exerted a cytostatic action as noted for erlotinib. These results supports the notion that HPPH-erlotinib has a potentially beneficial dual function: as chemotherapeutic agent to attenuate HNSCC cell proliferation and as PS to kill those cells which had it preferentially taken up.

Figure 14:
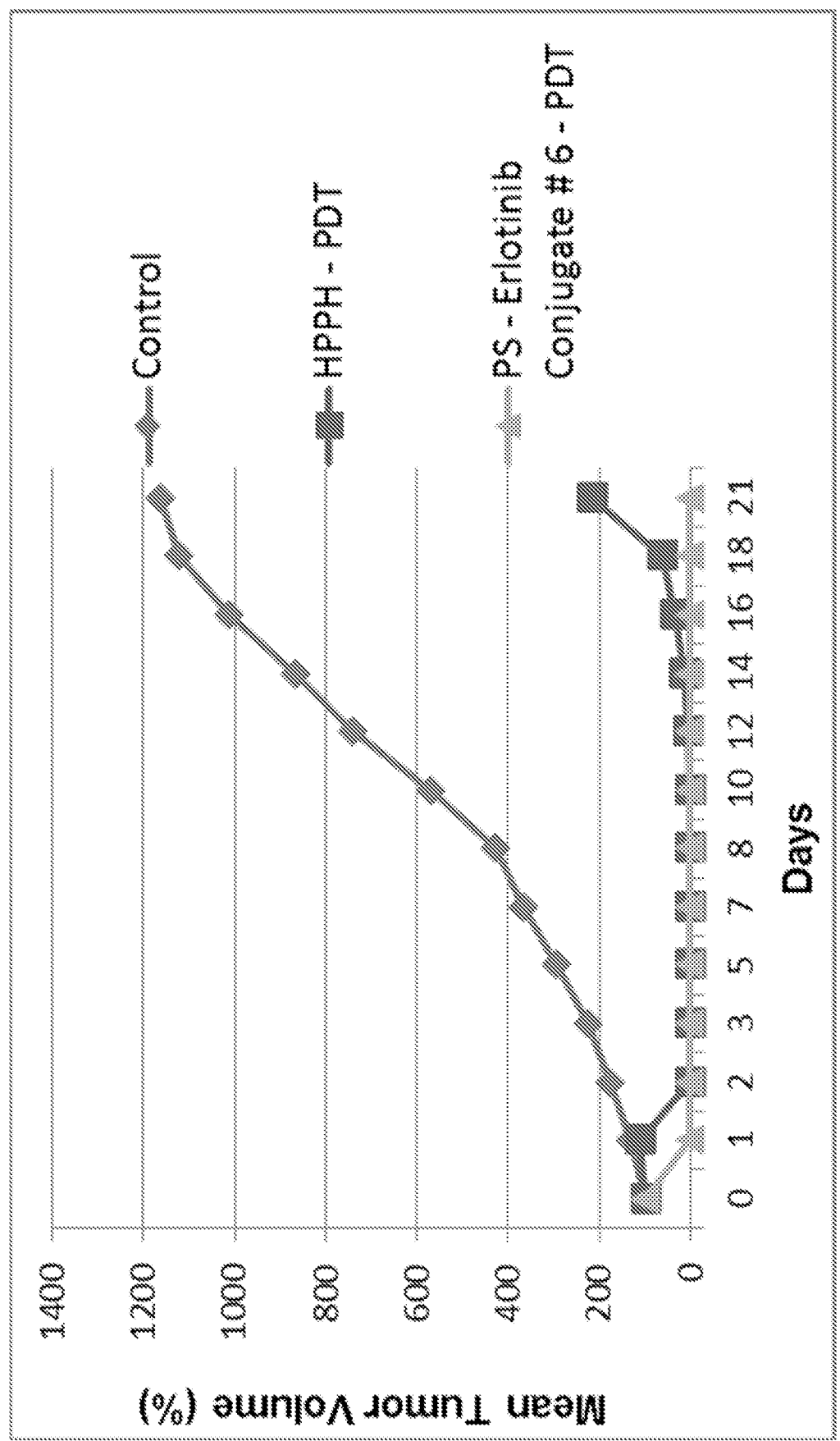
FIG. 14 shows the in vivo photosensitizing efficacy of PS-erlotinib conjugate 6 compared with HPPH in SCID mice bearing head and neck cancer tumor xenografts, known for high expression of EGFR. The results show improved efficacy of PS-erlotinib conjugate 6 over HPPH alone.

PS-erlotinib conjugate 6 showed improved efficacy than HPPH—The in vivo photosensitizing efficacy of PS-erlotinib conjugate 6 was compared with HPPH in SCID mice bearing head & neck cancer tumor xenografts, known for high expression of EGFR. When the tumors were 4-5 mm, the mice were injected (i. v.) with conjugate 6 (0.47 µmol/kg). At 24 h post-injection, the tumors were exposed to laser light (665 nm, 135 J/cm², 75 mW/cm²). Similar treatment parameters were used for HPPH (pyropheophorbide-a analog)—PDT also. The mice as a control group were not treated with light. For each experiment 5 SCID mice/group were used. The tumor growth was monitored daily. The results are summarized in FIG. 14 certainly show improved efficacy of PS-erlotinib conjugate 6 over the HPPH alone.

A novel approach for introducing EGFR inhibitor(s) at various peripheral positions of the unsymmetrical photosensitizers is established.

Depending upon the available functionalities in photosensitizing moieties, the nature of linker(s) joining the PS and erlotinib or its analog(s) was selected. Some of the conjugates investigated so far showed a remarkable difference in EGFR inhibition and biological efficacy. The results suggest that the position of the erlotinib group and the linker joining it to the PS make a significant difference in EGFR target-specificity.

The overall lipophilicity of the molecule can be altered by introducing a variety of hydrophilic or hydrophobic functionalities in tetrapyrrolic systems.

Tumor specificity can be achieved by both active and passive transport of the conjugates, and could vary from tumor to tumor type, and the stage of the cancer patient(s).

This disclosure for the first time provides an opportunity to make the selection of the PS (with and without Erlotinib-EGFR targeting moiety) for personalized PDT treatment of cancer patient(s) depending upon the expression of EGFR in tumors.

Although the present disclosure has been described with respect to one or more particular embodiments and/or examples, it will be understood that other embodiments and/or examples of the present disclosure may be made without departing from the scope of the present disclosure.

The invention claimed is:

1. A compound having the following structure:

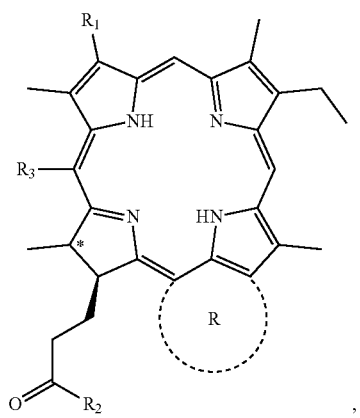

,

87
-continued
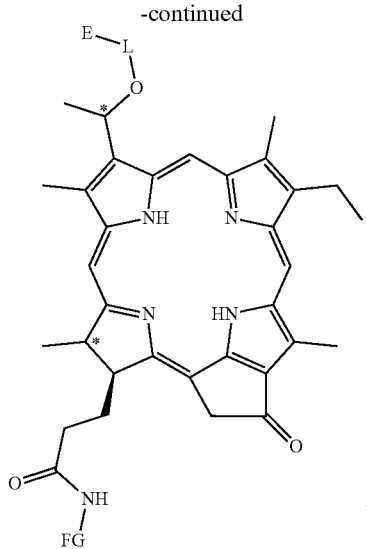
,
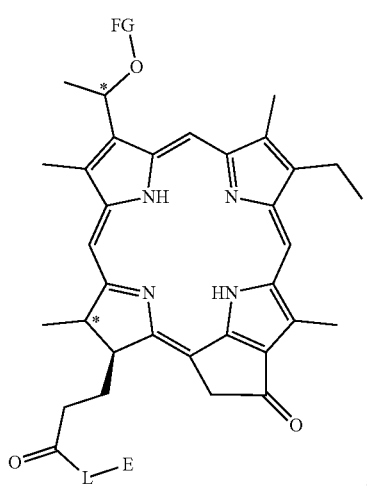
, or
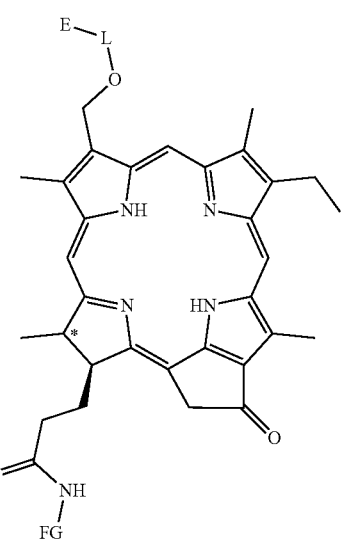
, or
88
-continued
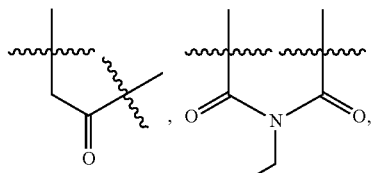
,
wherein R is
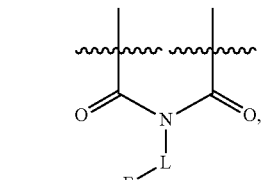 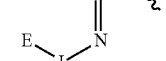
;
$R_1$ is
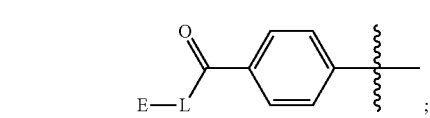
$R_2$ is —OH, —OCH$_3$, or L—E,
$R_3$ is H or
;

FG is
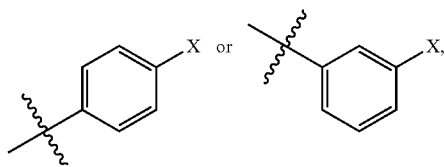
wherein X is —I, —Sn(CH$_3$)$_3$, or -$^{124}$I;
L is a linker moiety selected from the group consisting of:
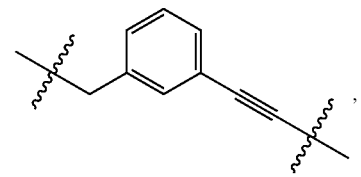
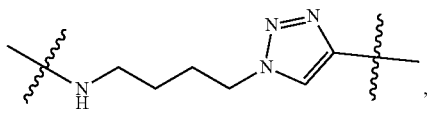
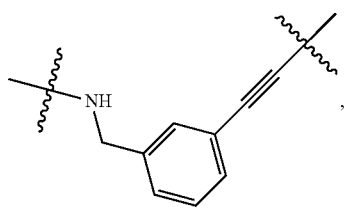
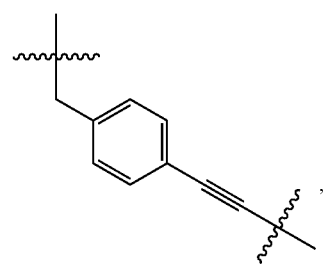
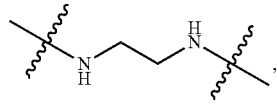
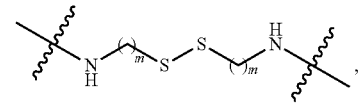
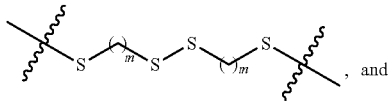, and
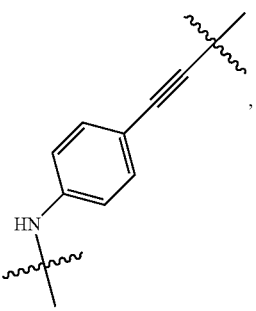
wherein m is 1, 2, 3, 4, 5, 6, 7, 8, 9, or 10; and
E is an erlotinib group or a group derived from an erlotinib analog selected from the group consisting of:
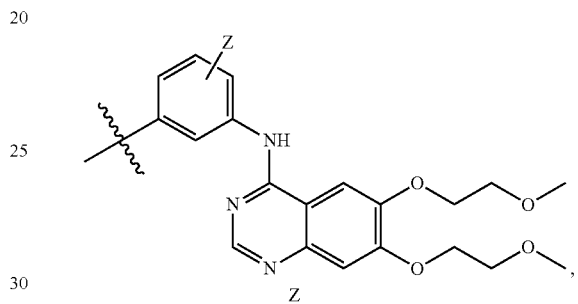
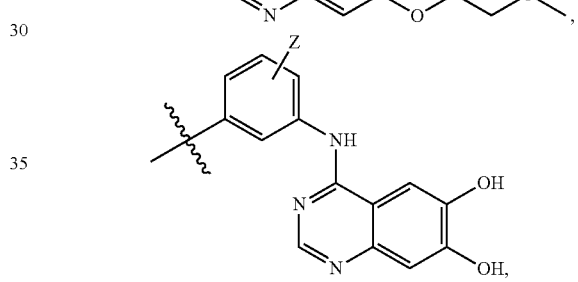
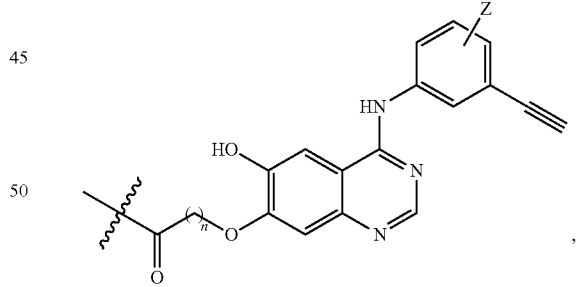
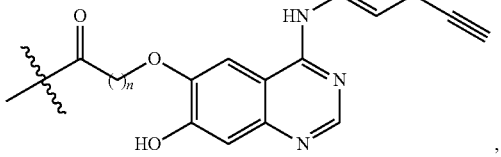

91
-continued
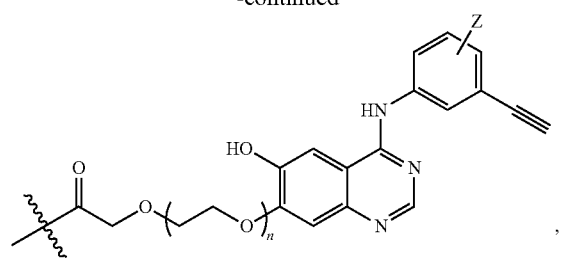
,
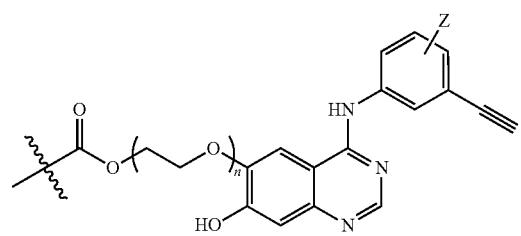
,
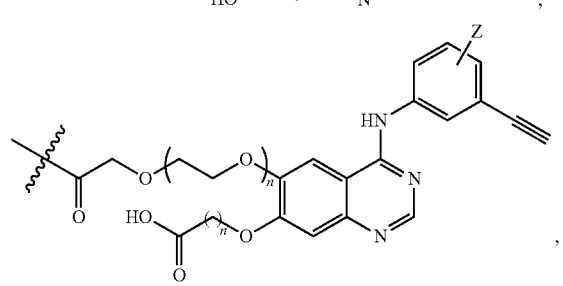
,
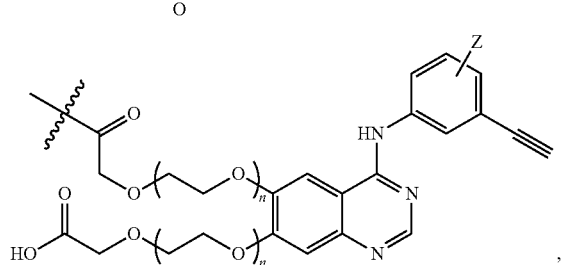
,
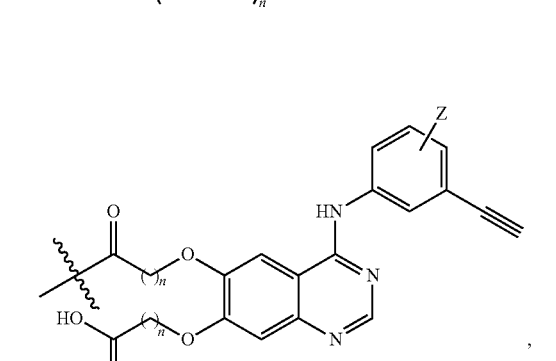
,
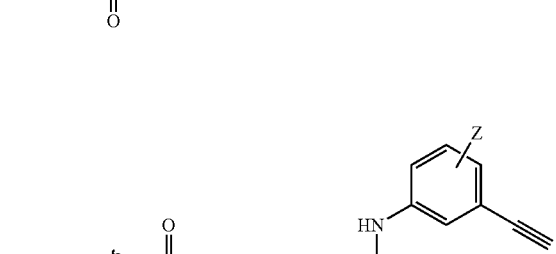
,
92
-continued
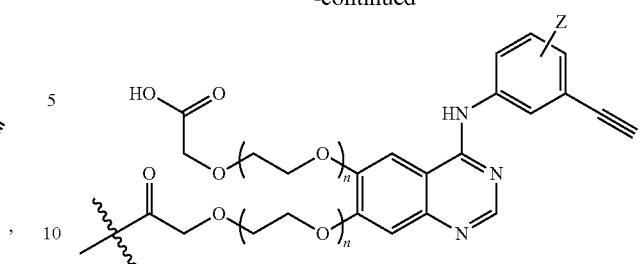
,
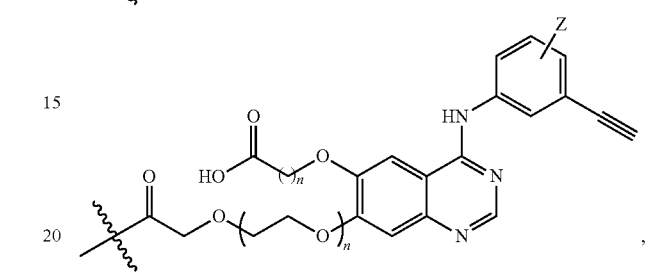
,
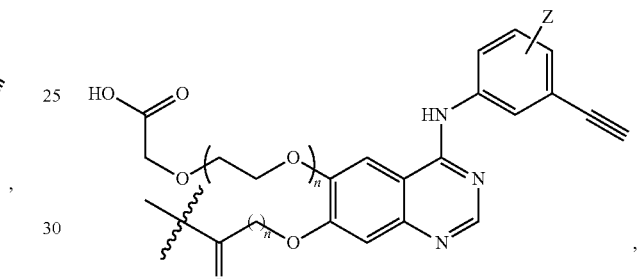
,
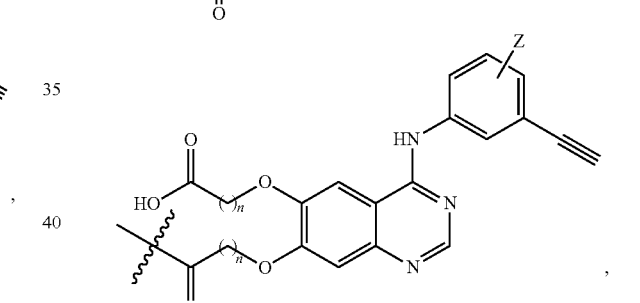
,
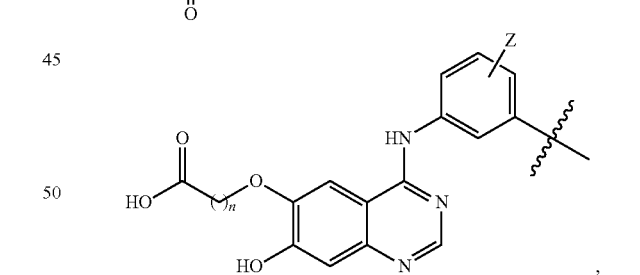
,
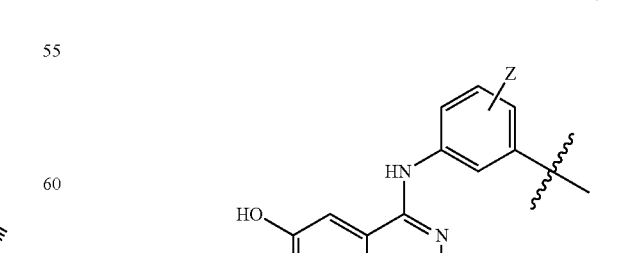
, 93
-continued
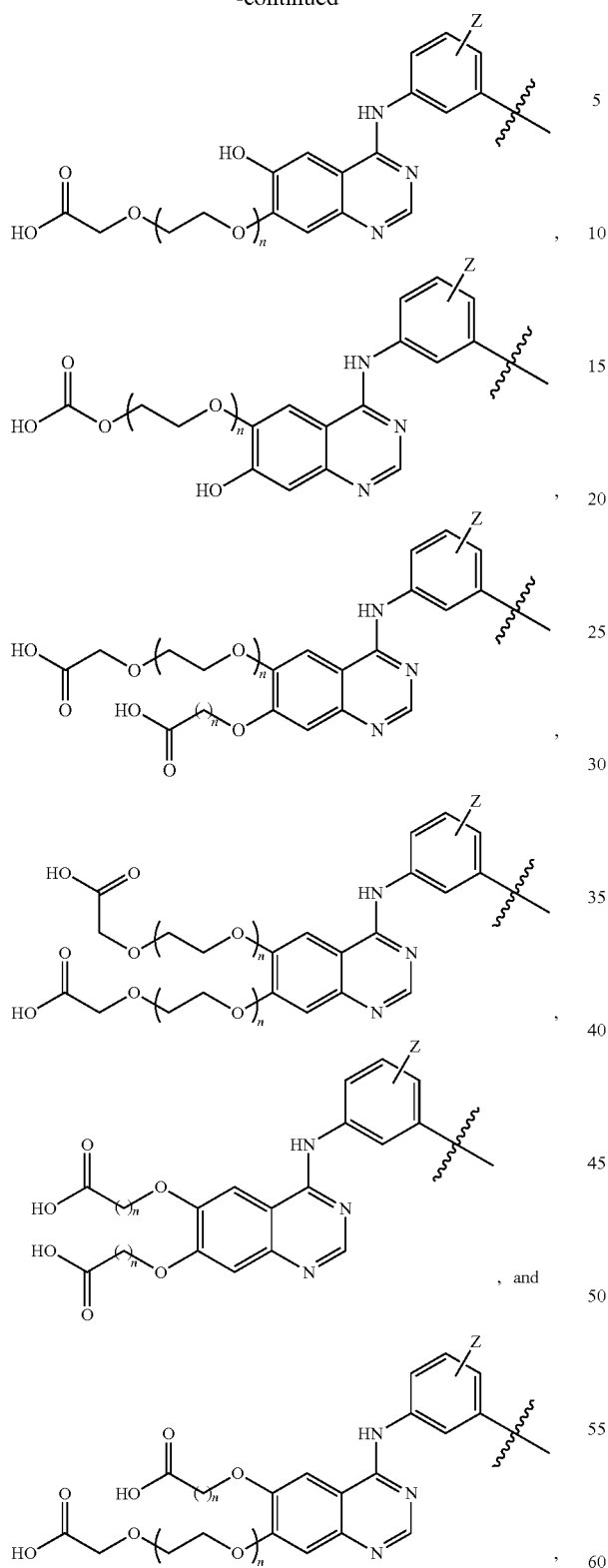
wherein n is 1, 2, 3, 4, 5, 6, Z is hydrogen, an electron withdrawing group, a deactivating group, or a combination thereof, and wherein each instance of the asterisk represents a chiral center.
94
2. The compound of claim 1, wherein the compound has the following structure:
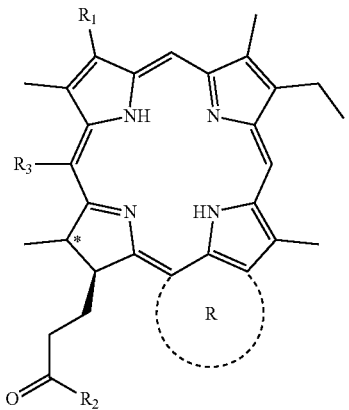
wherein R is
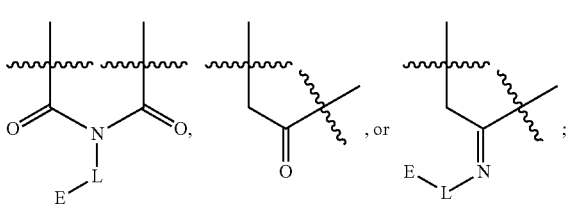
$R_1$ is
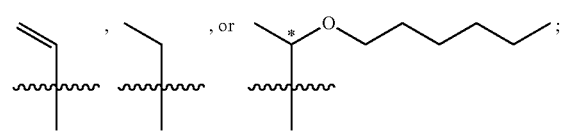
$R_2$ is —OH, —OCH$_3$, or L—E,
L is selected from the group consisting of:
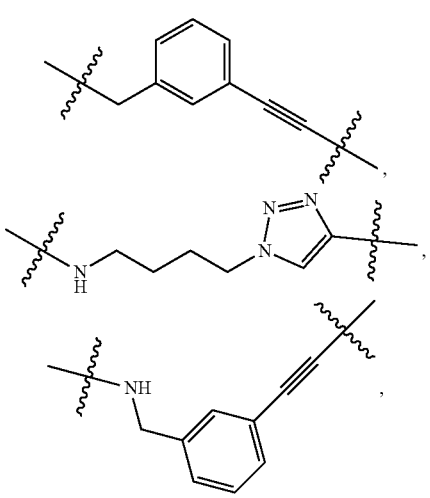

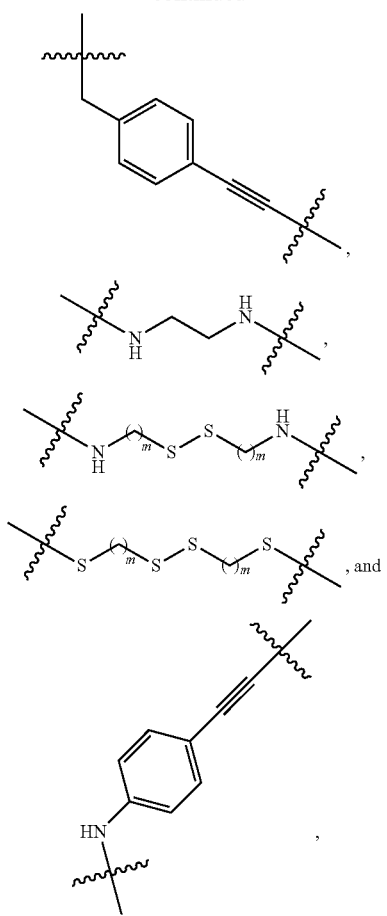
wherein m is 1, 2, 3, 4, 5, 6, 7, 8, 9, or 10; and E is selected from the group consisting of:
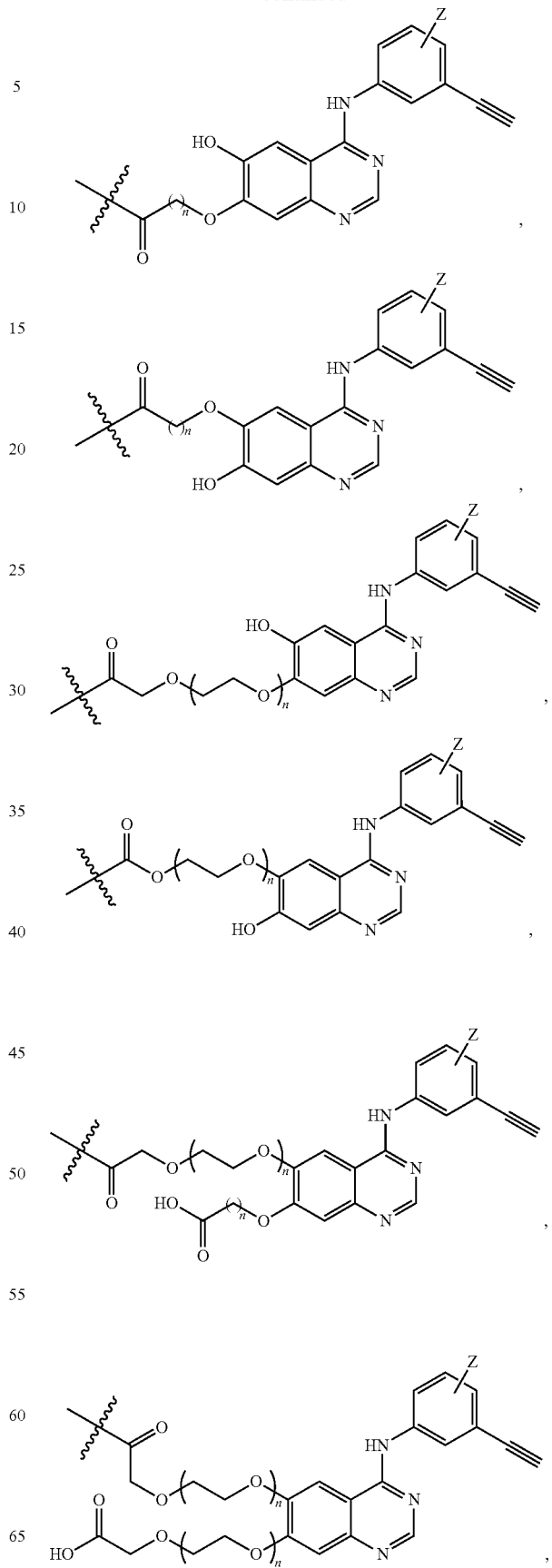

97
-continued
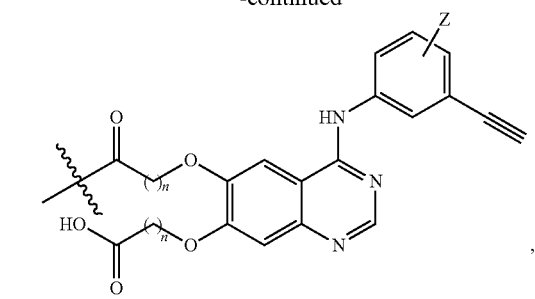
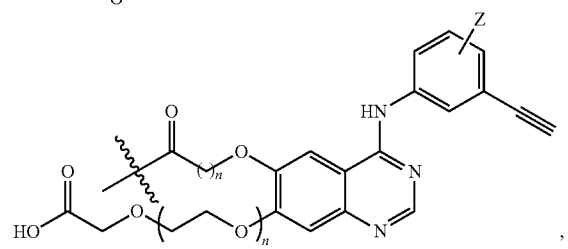
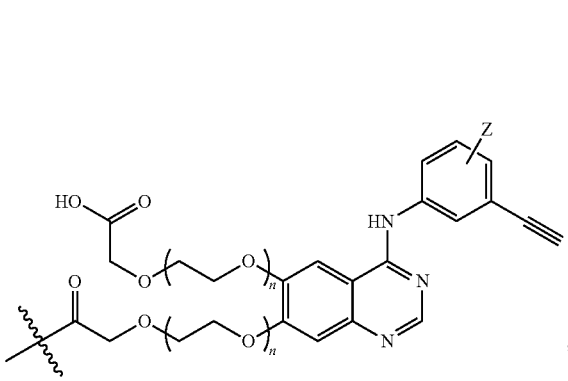
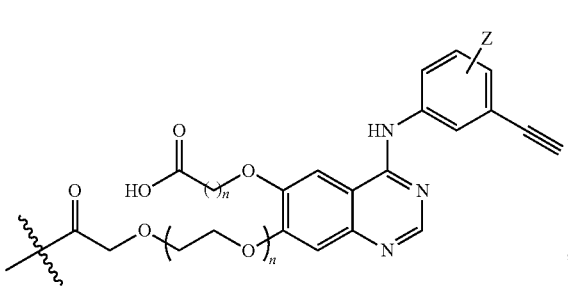
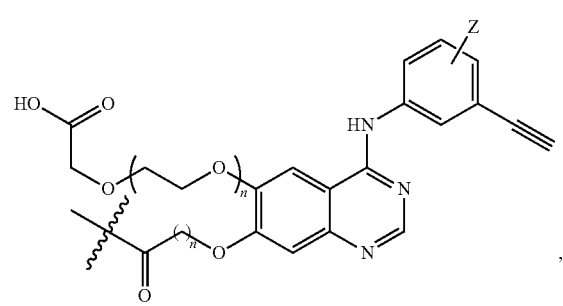
98
-continued
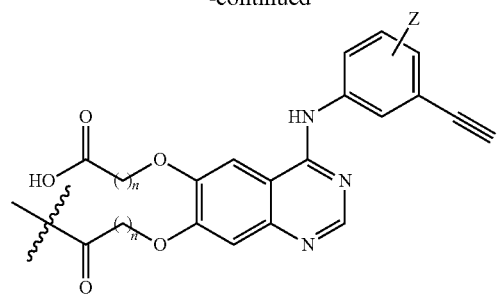
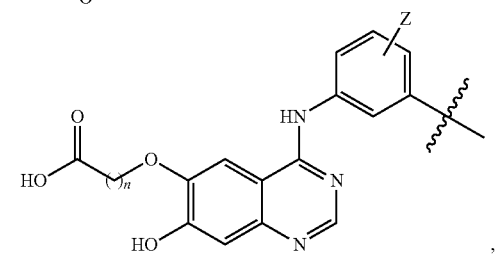
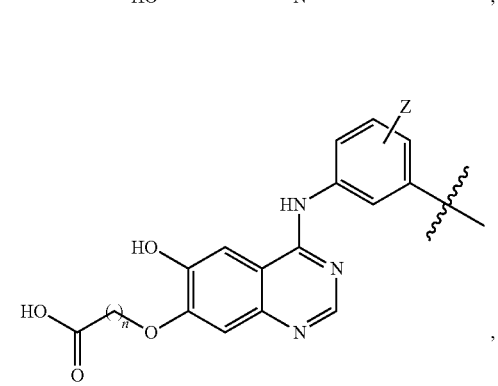
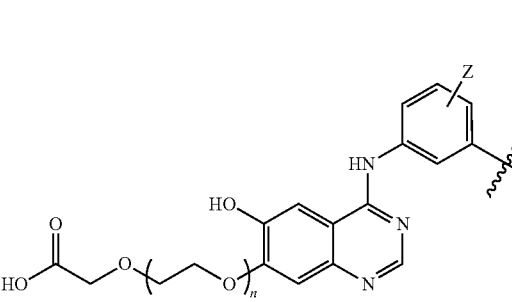
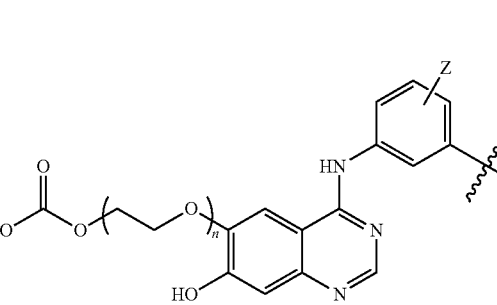

99
-continued
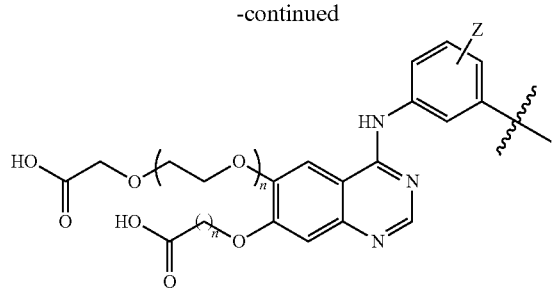
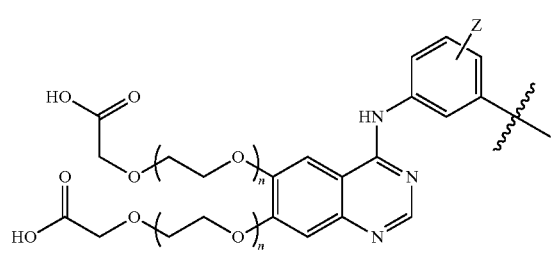
100
-continued
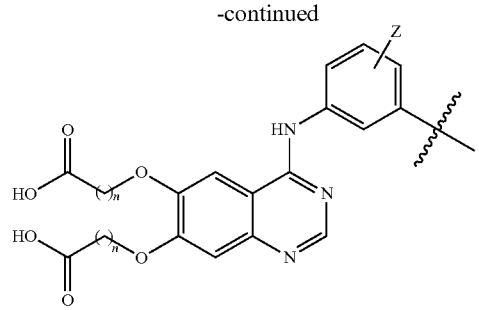
, and
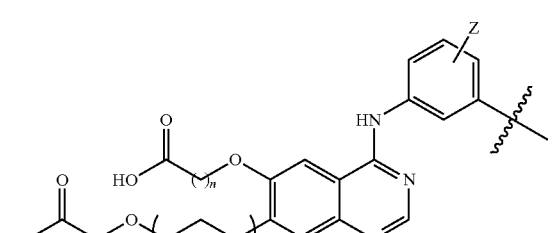
,
wherein n is 1, 2, 3, 4, 5, 6, Z is hydrogen, an electron withdrawing group, a deactivating group, or a combination thereof, and wherein each instance of the asterisk represents a chiral center.
3. The compound of claim 2, wherein the compound is selected from the group consisting of:
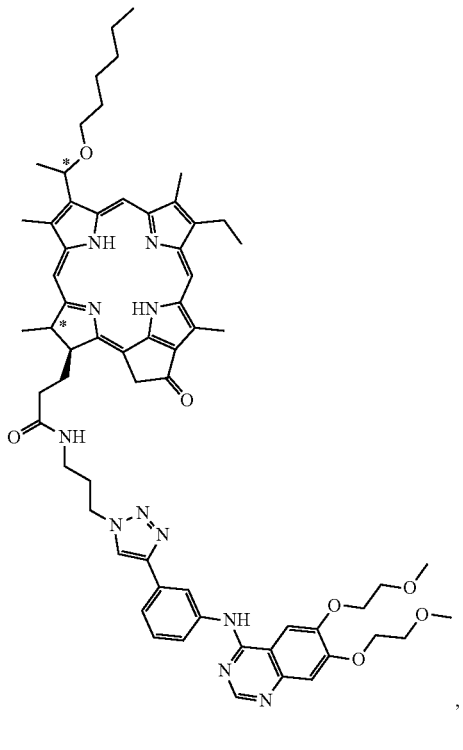
,
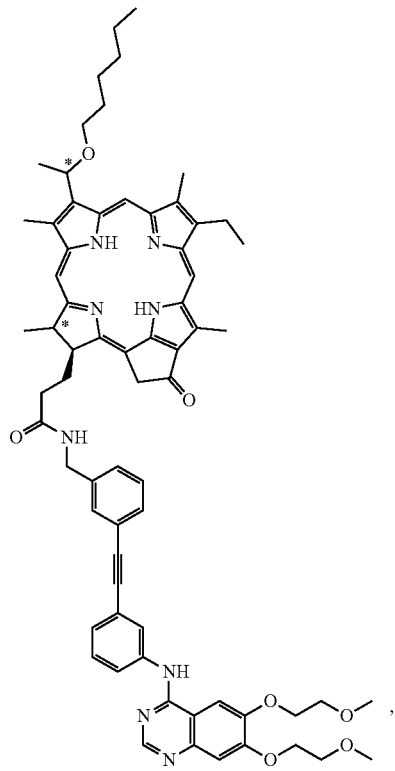
, -continued
101
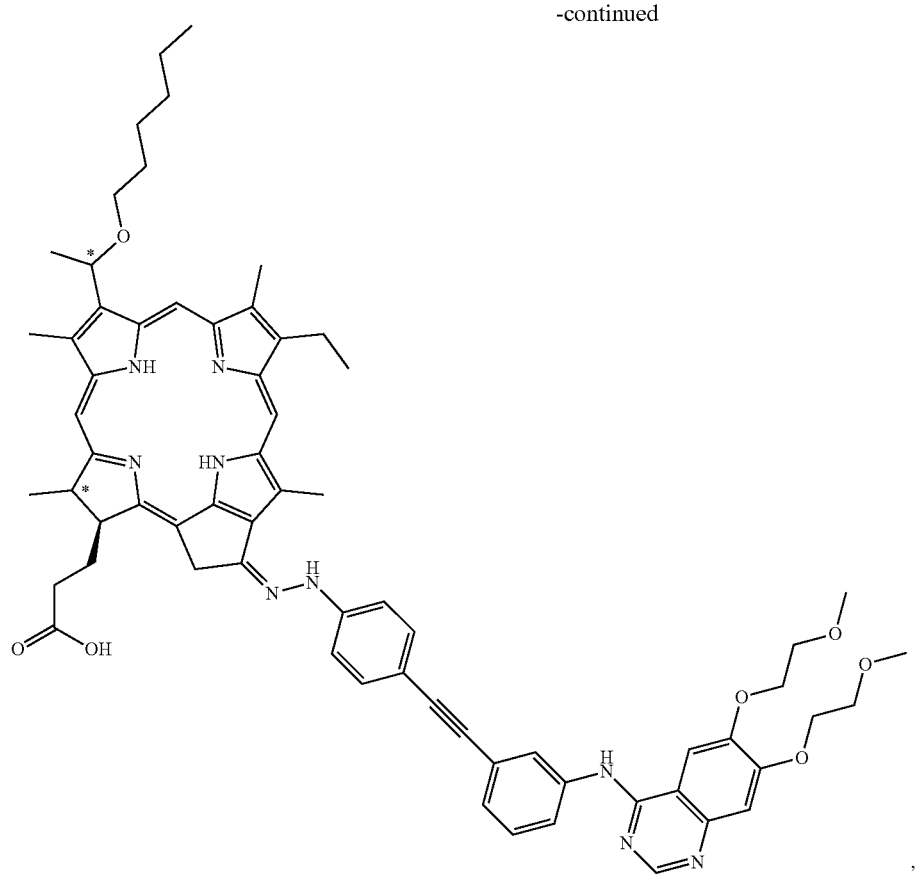
102
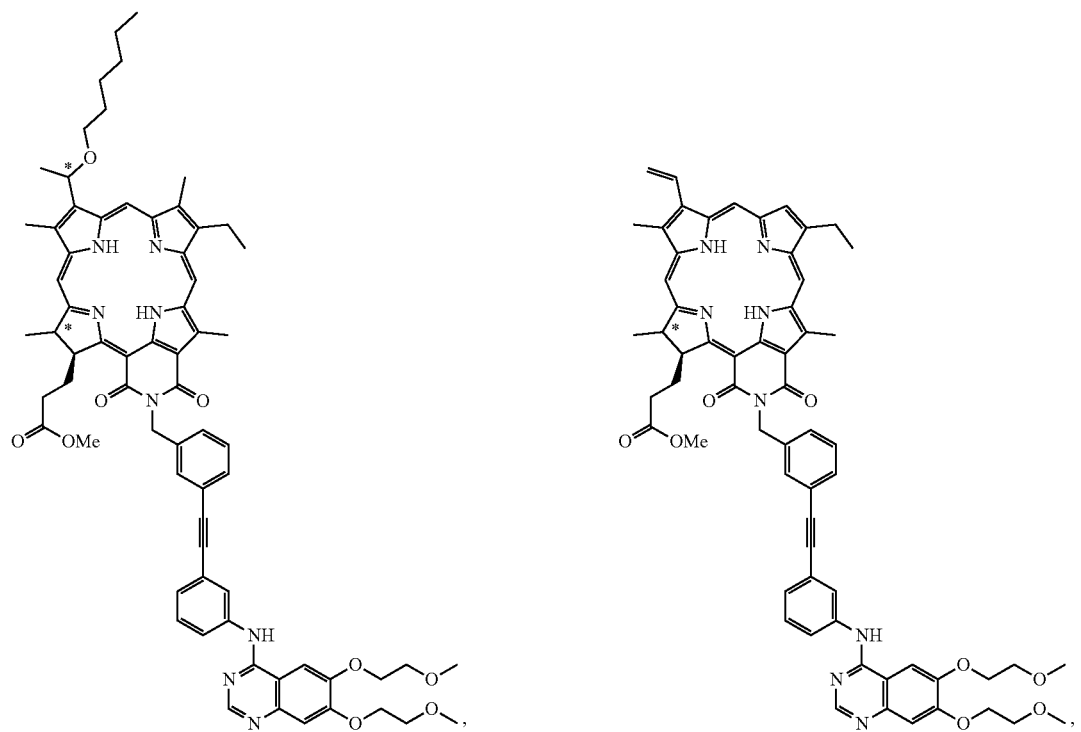

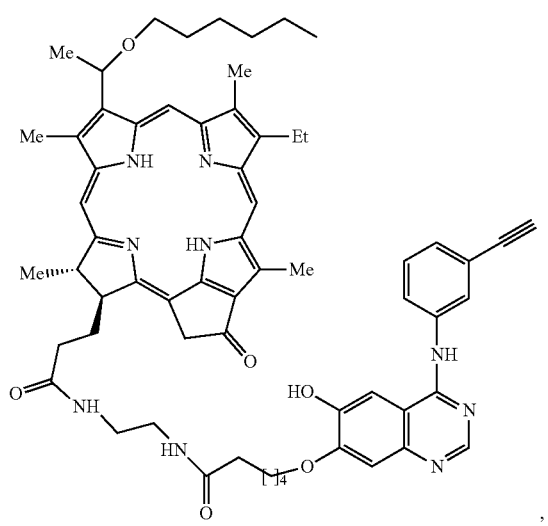
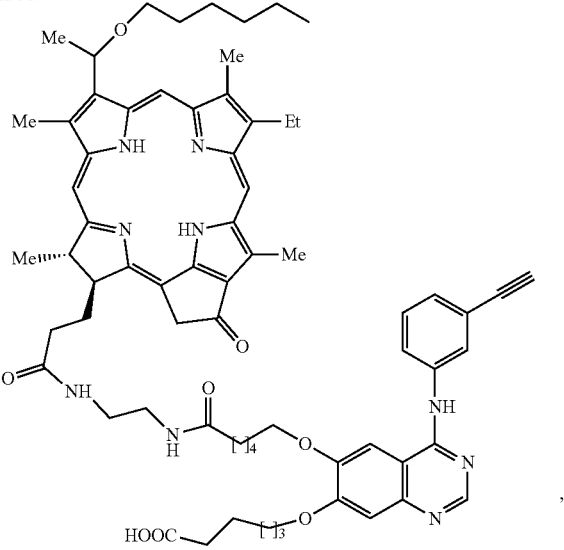
, or
wherein each occurrence of the asterisk is a chiral center.
4. The compound of claim 1, wherein the compound has the following structure:
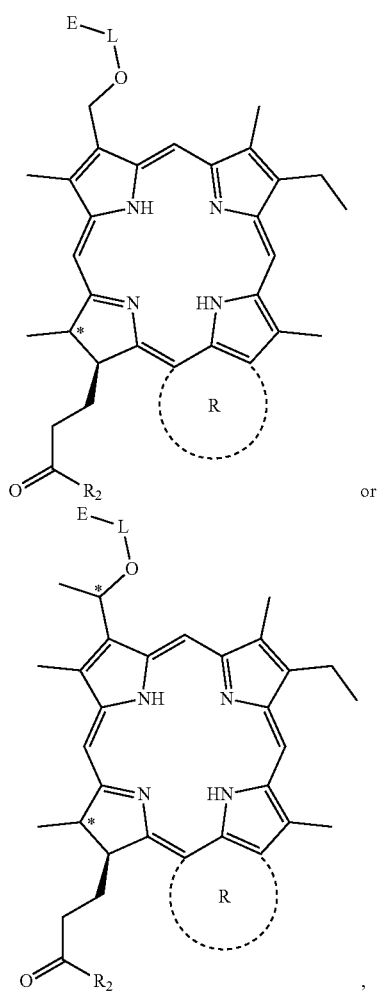
,
wherein R is
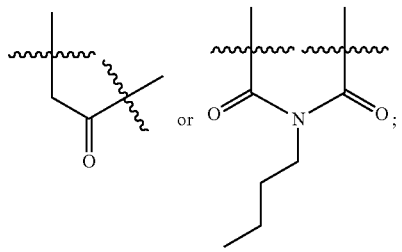 [SMILES: *CC(*)=O ; *C(=O)N(CCCC)C(*)=O]
;
$R_2$ is —OH or —OCH$_3$;
L is selected from the group consisting of:
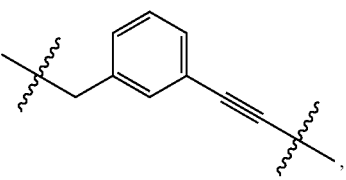
,
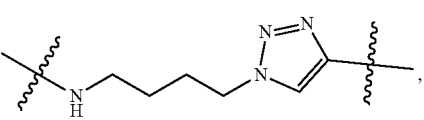
,
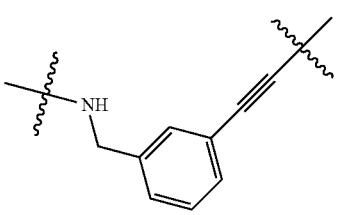
, 105
-continued
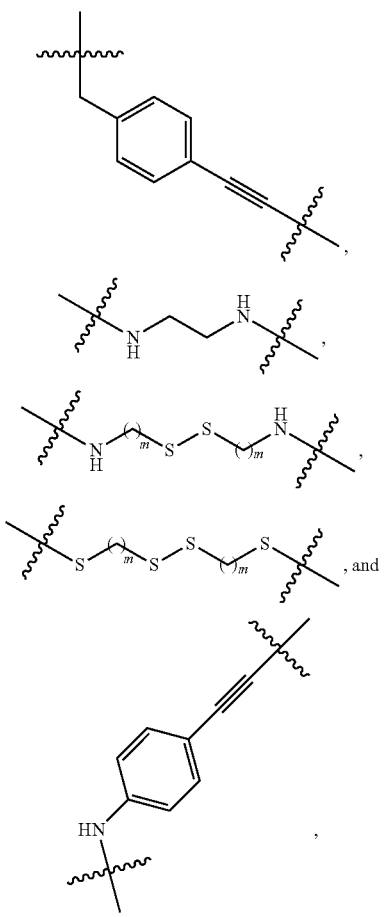
wherein m is 1, 2, 3, 4, 5, 6, 7, 8, 9, or 10; and
E is selected from the group consisting of:
106
-continued
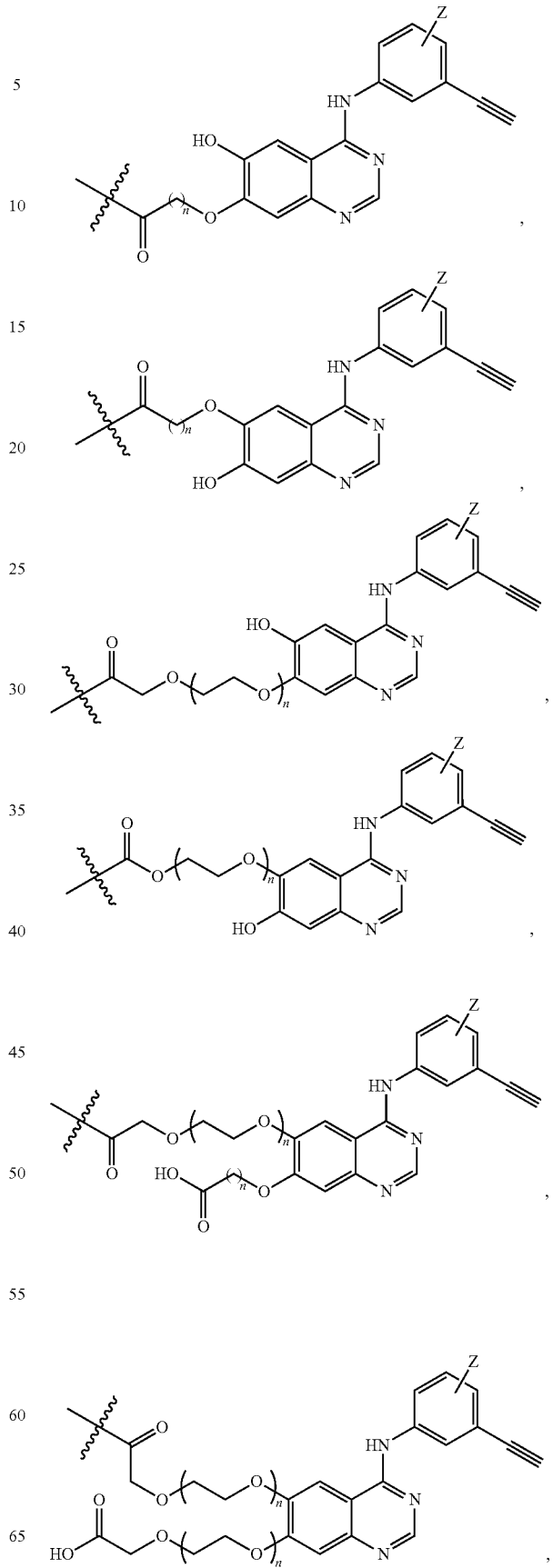

107
-continued
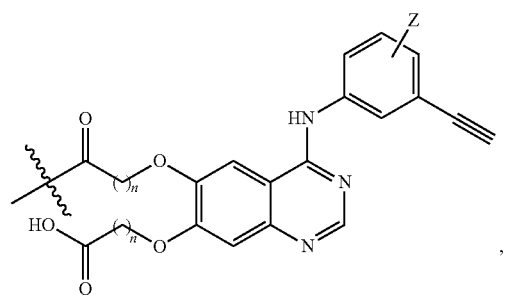
,
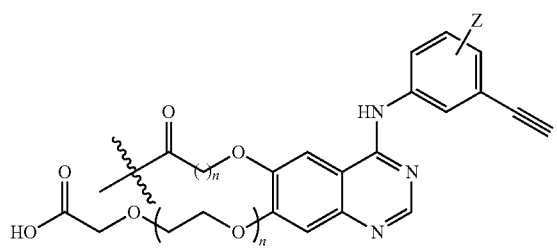
,
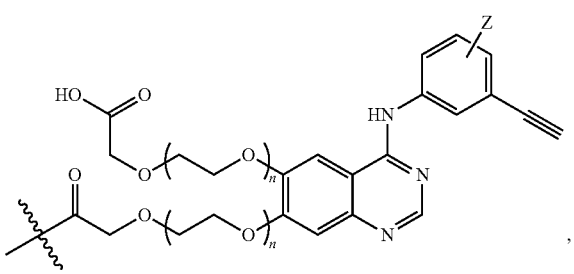
,
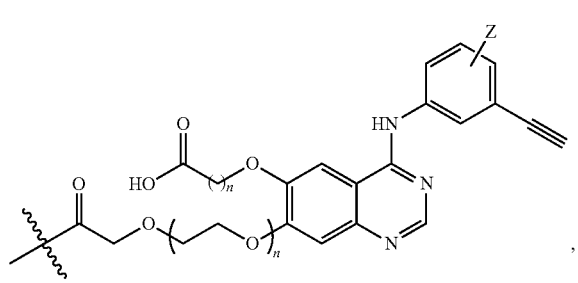
,
108
-continued
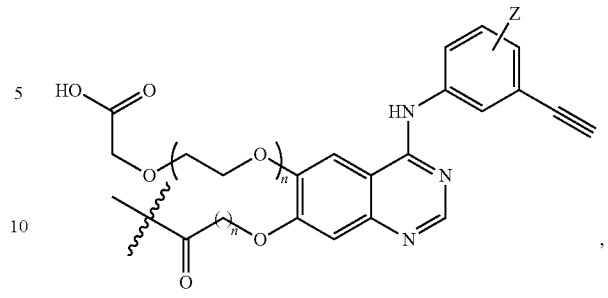
,
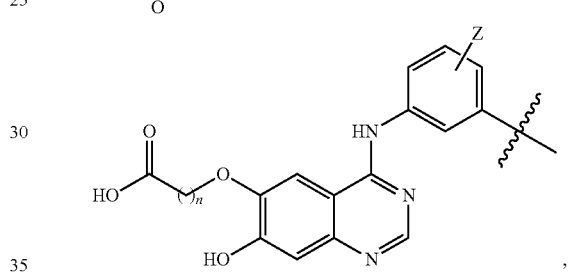
,
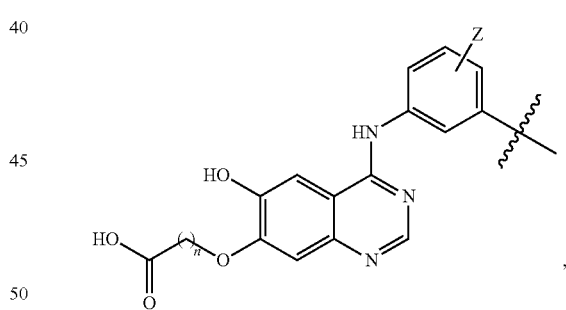
,
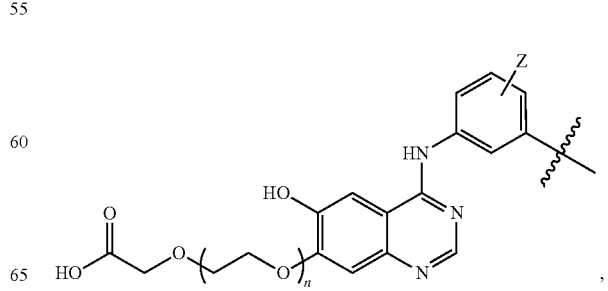
, -continued
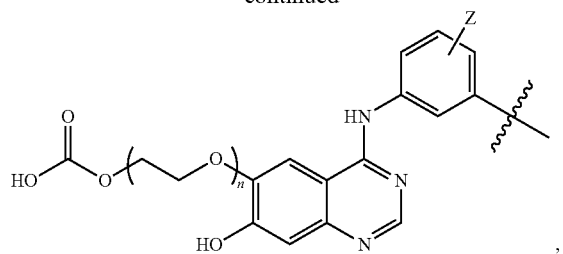
,
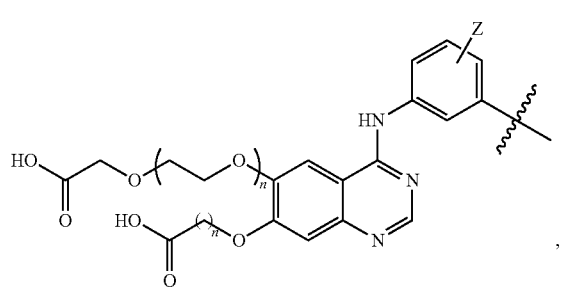
,
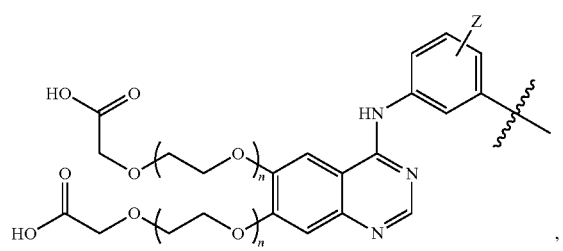
,
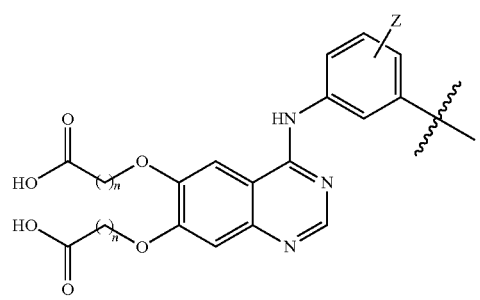
, and
-continued
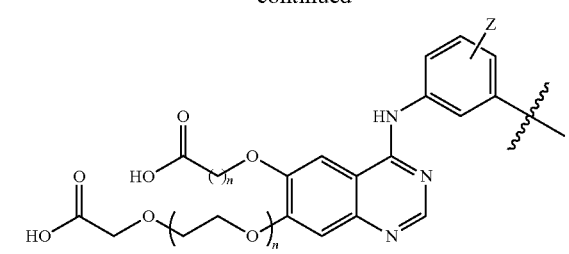
,
wherein n is 1, 2, 3, 4, 5, or 6, Z is hydrogen, an electron withdrawing group, a deactivating group, or a combination thereof, and wherein each instance of the asterisk represents a chiral center.
5. The compound of claim 4, wherein the compound is selected from the group consisting of:
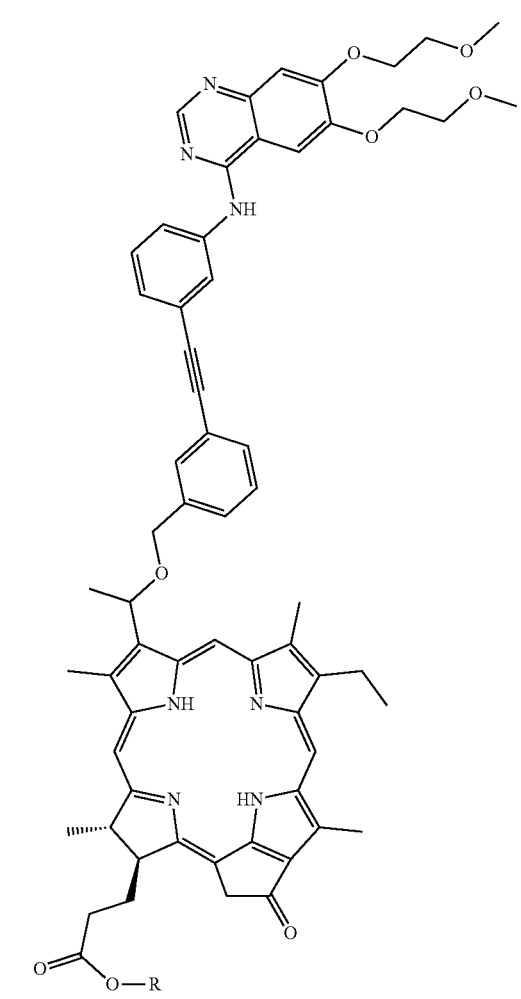
,

111
-continued
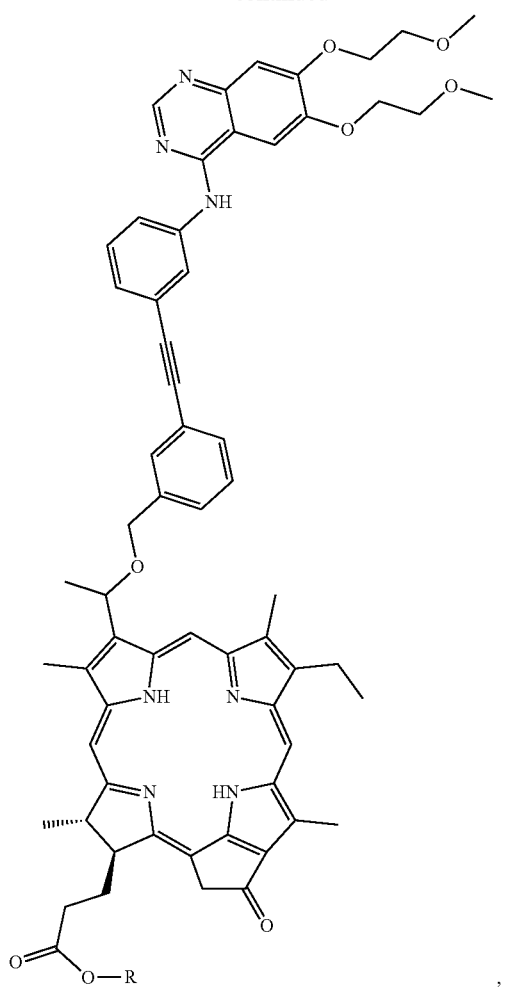
112
-continued
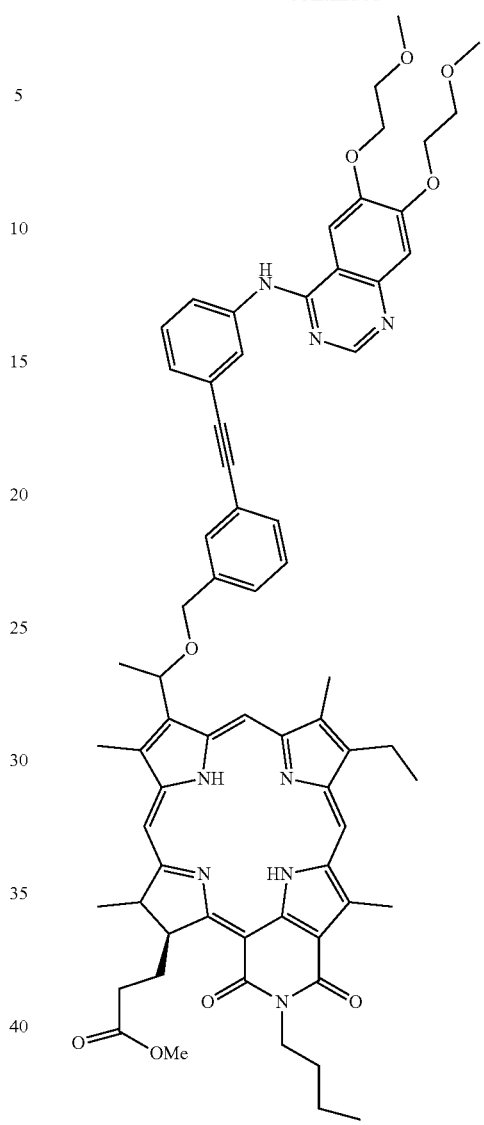
, or

-continued
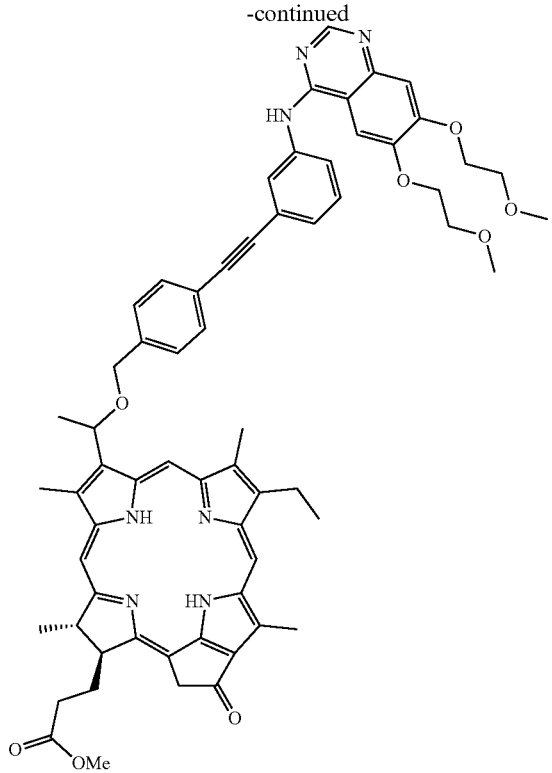
wherein R is hydrogen or methyl.
6. The compound of claim 1, wherein the compound has the following structuree:
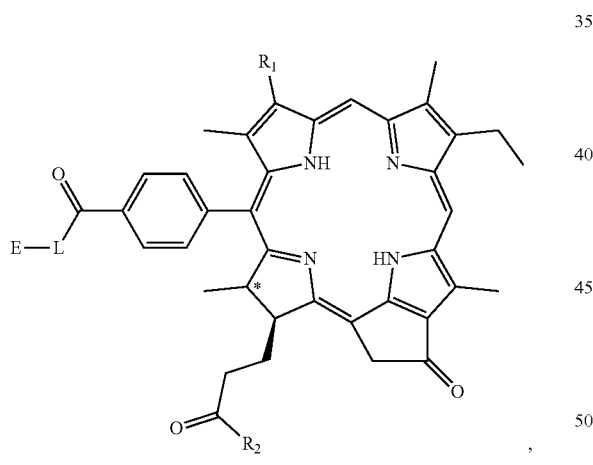
wherein $R_1$ is
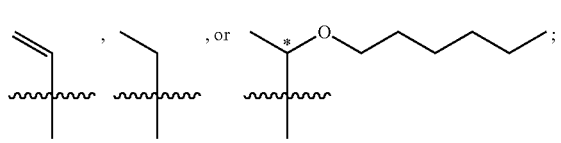
$R_2$ is —OH or —OCH$_3$;
L is selected from the group consisting of:
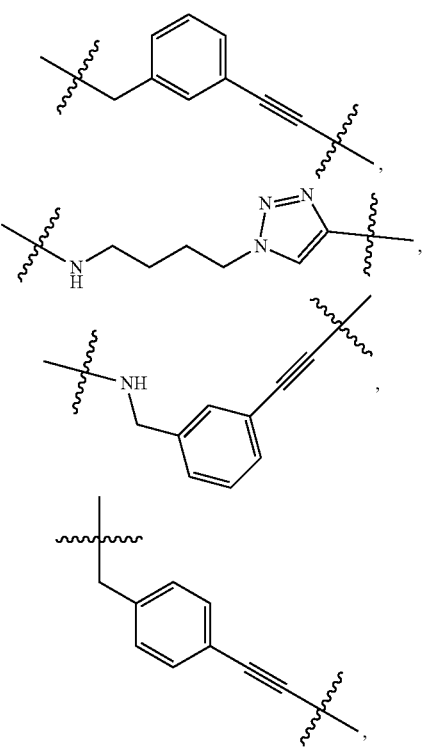
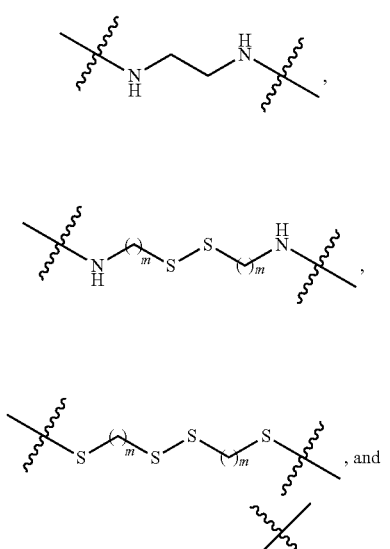
, and
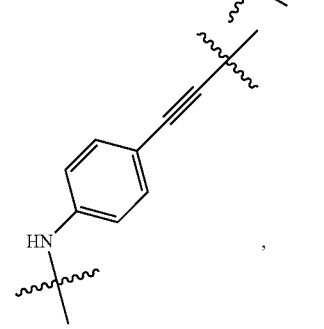

wherein m is 1, 2, 3, 4, 5, 6, 7, 8, 9, or 10; and
E is selected from the group consisting of:
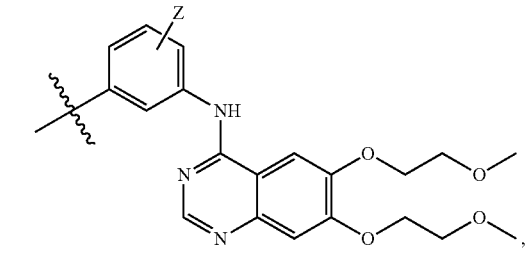
,
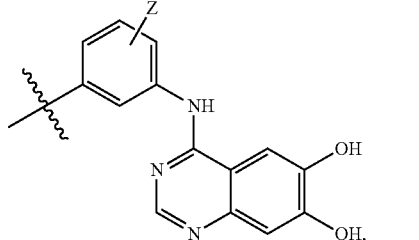
,
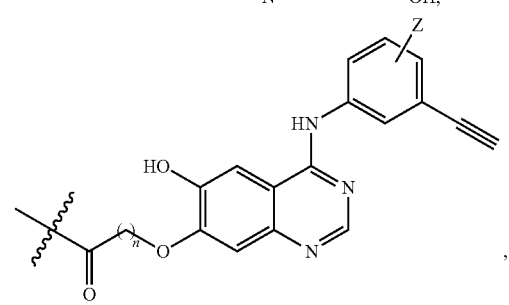
,
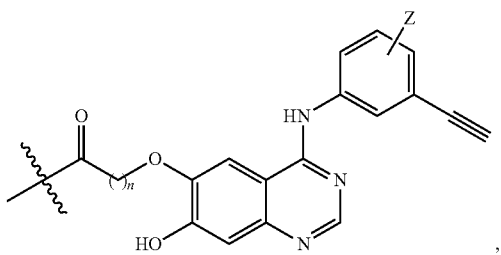
,
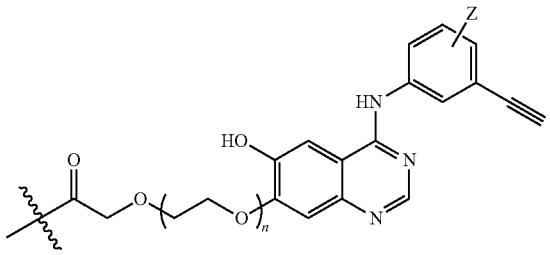
,
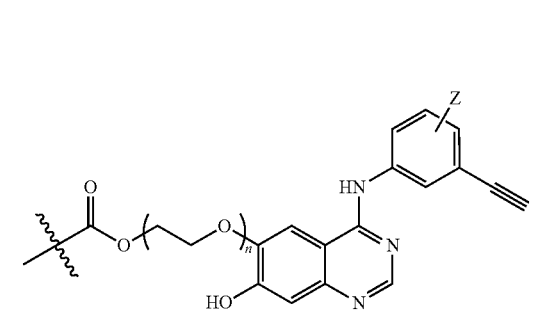
,
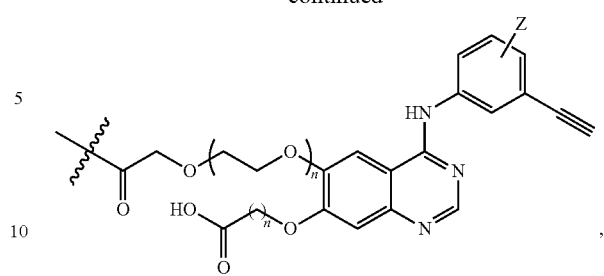
,
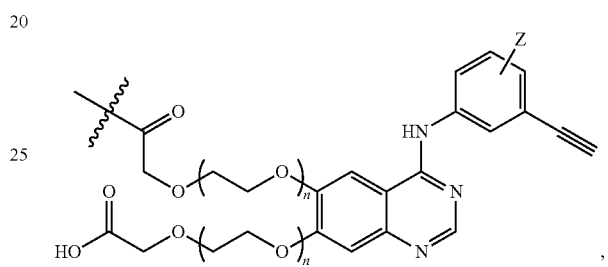
,
,
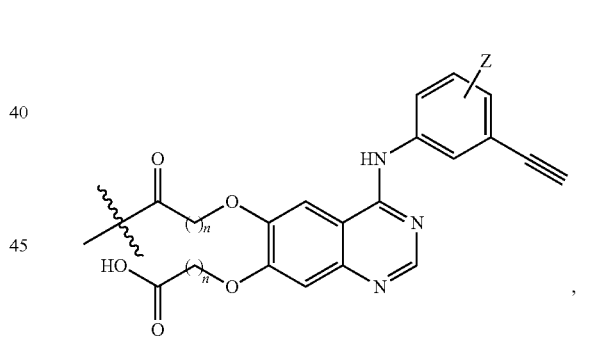
,
,
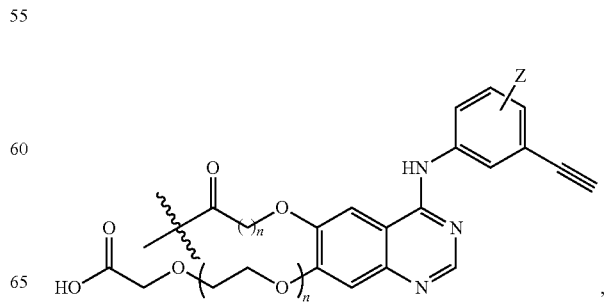
, 117
-continued
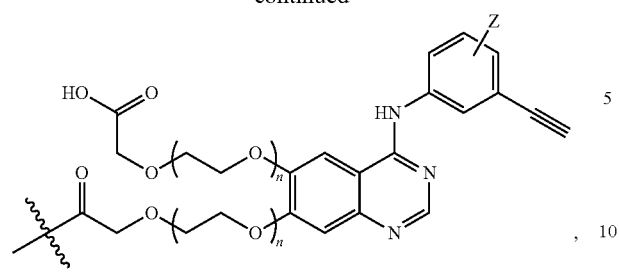,
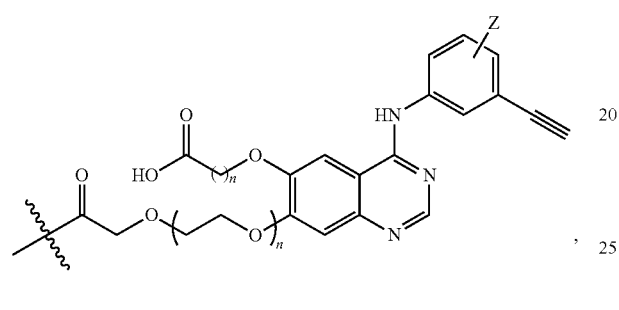,
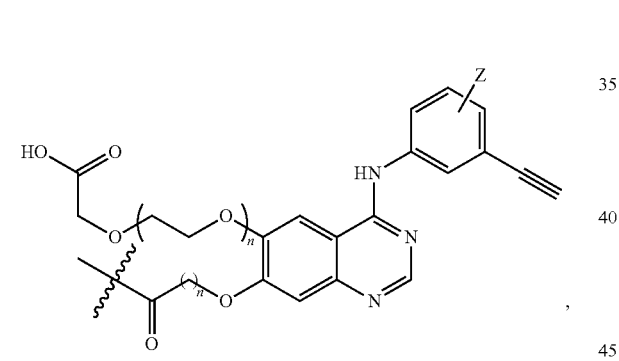,
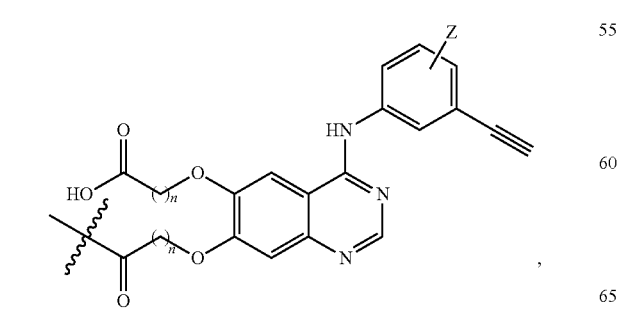,
118
-continued
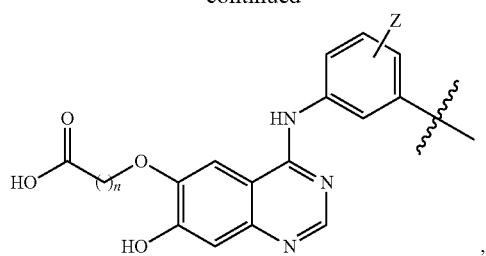,
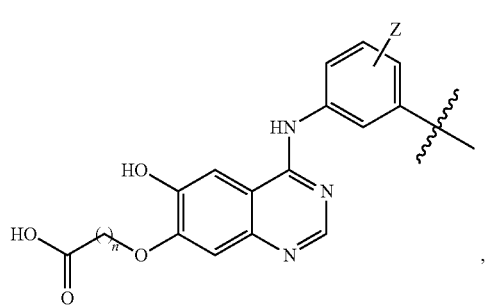,
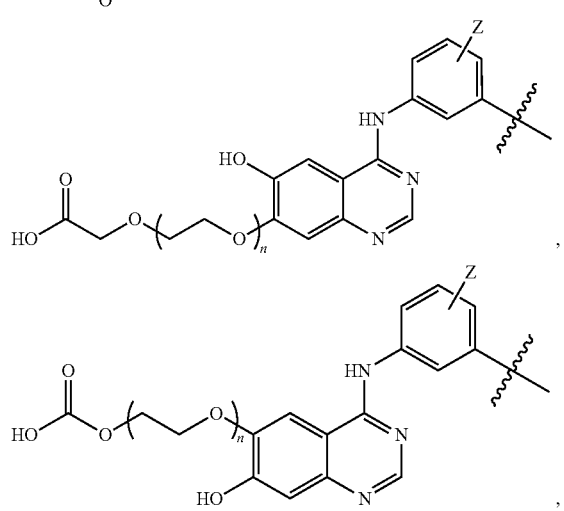,
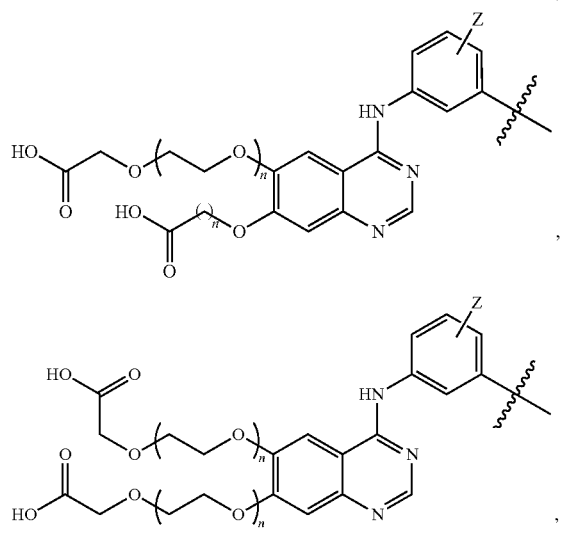, -continued

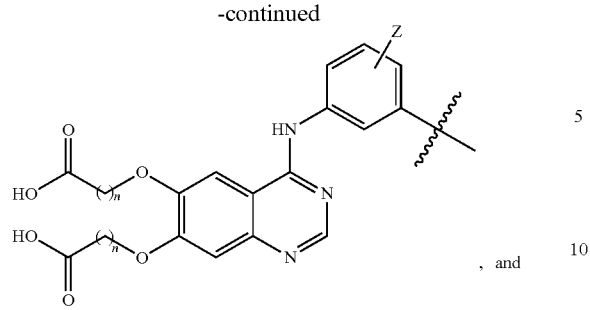

, and

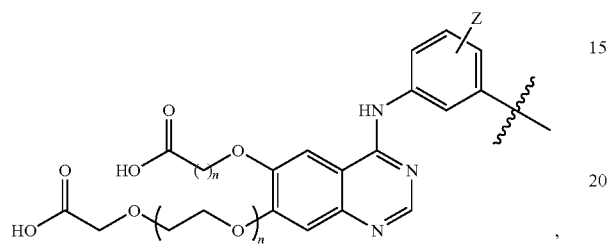

wherein n is 1, 2, 3, 4, 5, or 6, Z is hydrogen, an electron withdrawing group, a deactivating group, or a combination thereof, and wherein each instance of the asterisk represents a chiral center.

7. The compound of claim 6, wherein the compound has the following structure:

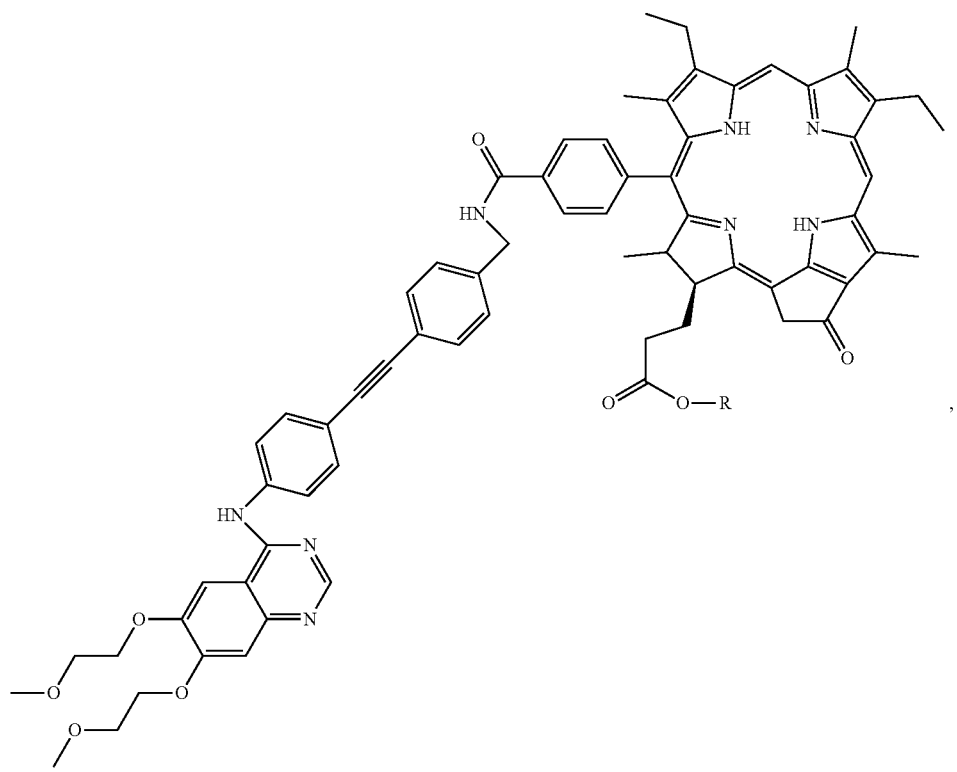

wherein R is —OH or —OCH$_3$.

8. The compound of claim 1, wherein the compound is PET active.

9. The compound of claim 1, wherein the compound has the following structure:

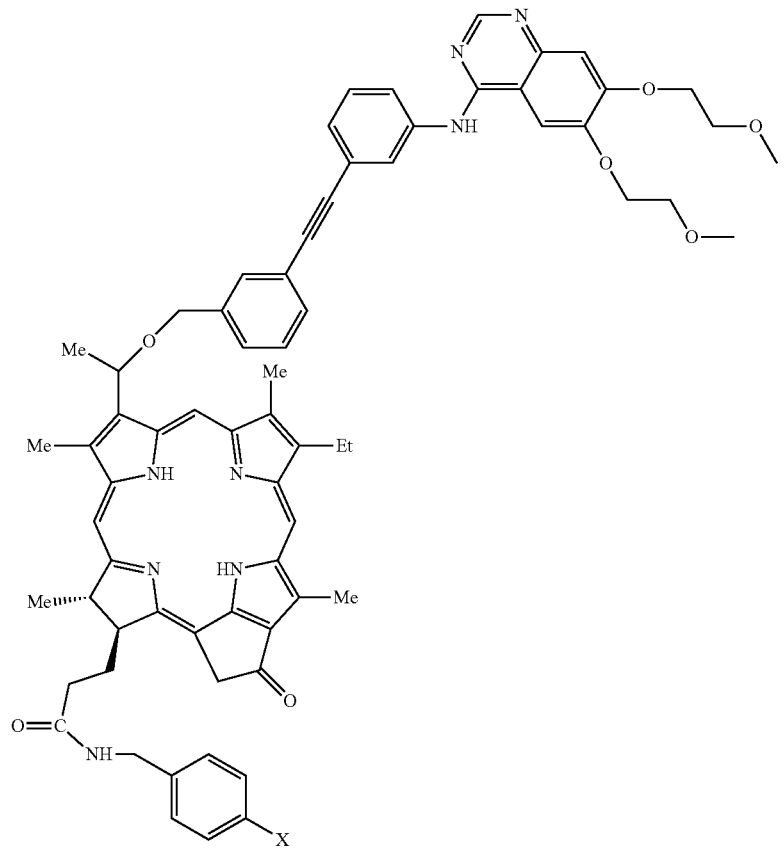

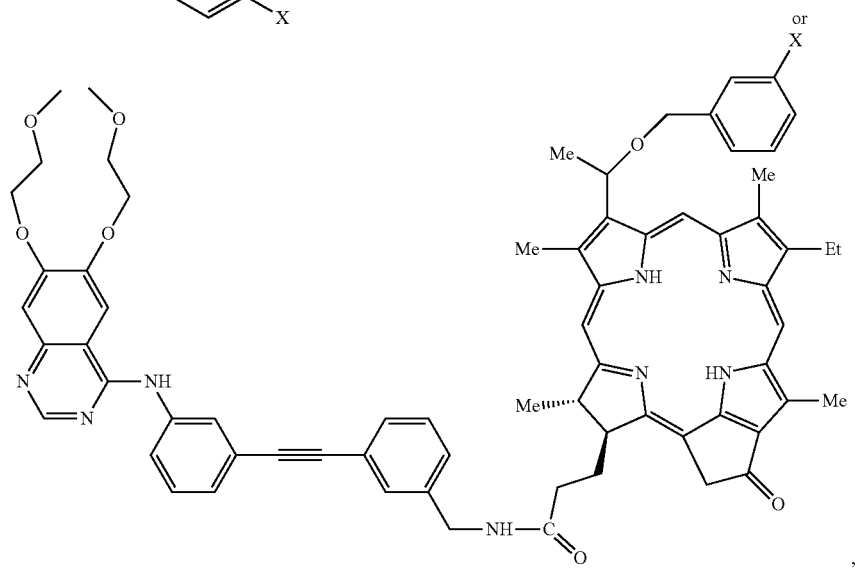

wherein X is iodine, —Sn(CH$_3$)$_3$, -$^{124}$I, or combinations thereof.

10. A composition comprising one or more compound of claim 1.

11. The composition of claim 10, wherein the composition further comprises a pharmaceutically acceptable carrier.

12. A method for detecting the presence of a hyperproliferative tissue in an individual comprising:
 administering to the individual an effective quantity of one or more compound of claim 1; and
 imaging the individual or a portion thereof to detect the presence or absence of a hyperproliferative tissue in an ididvidual.

13. The method of claim 12, wherein the imaging is fluorescence imaging and/or PET imaging.

14. The method of claim 12, wherein the method further comprises:
 exposing the individual with light of a wavelength to kill or impair the hyperproliferative tissue.

15. A method of photodynamic therapy for treating hyperproliferative tissue in an individual, comprising:

(i) administering to the individual the compound of claim 1, and
(ii) irradiating the individual with light of a wavelength to activate the compound, whereby the hyperproliferative tissue is treated.

16. The method of claim 15, wherein the hyperproliferative tissue is a vascular endothelial tissue, a neovasculature tissue, a neovasculature tissue present in the eye, an abnormal vascular wall of a tumor, a solid tumor, a tumor of a head, a tumor of a neck, a tumor of an eye, a tumor of a gastrointestinal tract, a tumor of a liver, a tumor of a breast, a tumor of a prostate, a tumor of a lung, a tumor of an ovary, a tumor of the bladder, a tumor of the thyroid, a nonsolid tumor, and malignant cells of one of a hematopoietic tissue and a lymphoid tissue.

17. The method of claim 15, wherein the individual has cancer.

18. The method of claim 17, wherein the cancer is selected from the group consisting of: head and neck cancer, bladder cancer, ovarian cancer, thyroid cancer, and lung cancer.

19. A kit comprising:
one or more compound of claim 1; and
instructions for use of the one or more compound.

20. The kit of claim 19, wherein the one or more compound is present in a pharmaceutical composition.

\* \* \* \* \*